(12) United States Patent
Pawlowski et al.

(10) Patent No.: US 7,834,149 B2
(45) Date of Patent: Nov. 16, 2010

(54) CARD-DOMAIN CONTAINING POLYPEPTIDES, ENCODING NUCLEIC ACIDS, AND METHODS OF USE

(75) Inventors: Krzysztof Pawlowski, Malmo (SE); John C. Reed, Rancho Santa Fe, CA (US); Adam Godzik, San Diego, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 11/876,595

(22) Filed: Oct. 22, 2007

(65) Prior Publication Data

US 2008/0109917 A1 May 8, 2008

Related U.S. Application Data

(60) Continuation of application No. 10/961,569, filed on Oct. 8, 2004, which is a division of application No. 10/032,159, filed on Dec. 19, 2001, now abandoned.

(60) Provisional application No. 60/257,457, filed on Dec. 21, 2000.

(51) Int. Cl.
*C07K 14/00* (2006.01)
(52) U.S. Cl. ...................... 530/350; 530/300
(58) Field of Classification Search ................. 530/350, 530/300
See application file for complete search history.

(56) References Cited

U.S. PATENT DOCUMENTS

| 5,840,708 A | 11/1998 | Weiss |
| 6,599,697 B1 | 7/2003 | Sodoyer et al. |
| 6,936,690 B2 | 8/2005 | Bertin |

FOREIGN PATENT DOCUMENTS

WO     WO 0159065 A2     8/2001

OTHER PUBLICATIONS

MPSRCH search result, 2009, us 11-876-595.15.rni. result 1, pp. 1-2, and MPSRCH search result, 2009,us-11-876-595. 16.rni.result 1, pp. 1-2.*
MPSRCH search result, 2009, us 11-876-595.16.rag, result 10, pp. 1-4.*
Ofran Y et al, 2005 (Drug Discovery Today, 10 (21): 1475-1482).*
Skolnick et al, 2000 (Trends in Biotech. 18:34-39).*
Bork, 2000 (Genome Research 10:398-400).*
Barlett et al, 2003 (In: Structural Bioinformatics, Bourne et al, eds, Wiley-Liss, Inc., pp. 387-407).*
Rost et al, 2003 (Cell Mol Life Sciences, 60: 2637-2650).*
Ahmad et al., "CRADD, a novel human apoptotic adaptor molecule for Caspase-2, and FasL/tumor Necrosis factor receptor-interacting protein RIP," *Cancer Res.* 57:615-619 (1997).
Bateman et al., "Pfam 3.1: 1313 multiple alignments and profile HMMs match the majority of proteins," *Nucleic Acids Res.* 27:260-262 (1999).
Bowie et al., "Deciphering the Message in Protein Sequences: Tolerance to Amino Acid Substitutions," *Science*, 247:1306-1310 (1990).
Branch, AD, "A good antisense molecule is hard to find," *Trends Biochem. Sci.*, 23: 45-50 (1998).
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol.* 11:2129-2138 (1990).
Crystal, R., "Transfer of Genes to Humans: Early Lessons and Obstacles to Success," *Science* 270:404-410 (1995).
Deonarain, M., "Ligand-targeted receptor-mediated vectors for gene delivery," *Exp. Opin. Ther. Patents* 8(1):53-69 (1998).
DiDonato et al., "A cytokine-responsive KB kinase that activates the transcription factor NF-KB," *Nature* 388:548-554 (1997).
Hofmann and Bucher, "The CARD domain: a new apoptotic signalling motif," *Trends Biochem. Sci.* 22:155-156 (1997).
Lazar et al., "Transforming Growth Factor α: Mutation of Aspartic Acid 47 and Leucine 48 Results in Different Biological Activities," *Moll. Cell. Biol.* 8:1247-1252 (1988).
Lee et al., "COP, a Caspase Recruitment Domain-containing Protein and Inhibitor of Caspase-1 Activation Processing," *J. Biol. Chem.* 276:34495-34500 (2001).
Li et al., "Saturated Blast: An automated multiple intermediate sequence search used to detect distant homology," *Bioinformatics* 16:1105-1110(2000).
Miller and Vile, "Targeted vectors for gene therapy," *FASEB J.* 9:190-199 (1995).
Rothe et al., "The TNFR2-TRAF signaling complex contains two novel proteins related to baculoviral inhibitor of apoptosis proteins," *Cell* 83:1243-1252 (1995).
Rychlewski et al., "Comparison of sequence profiles. Strategies for structural predictions using sequence information," *Protein Science* 9:232-241 (2000).
Sambrook et al., eds, *Molecular Cloning, A laboratory manual*, Second edition, Cold Spring Harbor Laboratory Press, Cold Spring Harbor, p. 11.31-11.32 (1989).

(Continued)

*Primary Examiner*—Larry R. Helms
*Assistant Examiner*—Minh-Tam Davis
(74) *Attorney, Agent, or Firm*—McDermott Will & Emery LLP

(57) ABSTRACT

The invention provides caspase recruitment domain (CARD)-containing polypeptides and functional fragments thereof, encoding nucleic acid molecules, and specific antibodies. Also provided are screening methods for identifying CARD-associated polypeptides (CAPs), and for identifying agents that alter the association of a CARD-containing polypeptide with itself or with a CAP. Further provided are methods of altering a biochemical process modulated by a CARD-containing polypeptide, and methods of diagnosing a pathology characterized by an increased or decreased level of a CARD-containing polypeptide.

2 Claims, 11 Drawing Sheets

OTHER PUBLICATIONS

Shaerwin-Whyatt et al., "Subcellular localization and CARD-dependent oligomerization of the death adaptor RAIDD," *Cell Death Differ.* 7:155-165 (2000).

Shiozaki et al., "Oligomerization and activation of caspase-9, induced by Apaf-1 CARD," *Proc Natl Acad Sci.* 99:4197-4202 (2002).

Thome et al., "Identification of CARDIAK, a RIP-like kinase that associates with caspase-1," *Curr. Biol.* 8:885-888 (1998).

van der Biezen and Jones, "The NB-ARC domain: a novel signalling motif shared by plant resistance gene products and regulators of cell death in animals," *Curr. Biol.* 8:R226-R227.

Verma and Somia, "Gene therapy—promises, problems and prospects," *Nature* 389:239-242 (1997).

Willis et al., "Bcl10 is involved in t(1;14)(p22;q32) of Malt B cell lymphoma and mutated in multiple tumor types," *Cell* 96:35-45 (1999).

MPSRCH search report, 2004, us-10-032-159a-18, rag, p. 3.
MPSRCH search report, 2007, SEQ 15 oligo, p. 1.
MPSRCH search result, 2007, us 10.961.569.15.rni.result 1, pp. 1-2.
MPSRCH search result, 2007, us-10.961.569.16.rni.result 1, pp. 1-2.
MPSRCH search report, 2004, us-10-032-159a-15.oligo100.rni, p. 1.
MPSRCH search report, 2004, us-10-032-159a-17.rnpb, p. 2-3 and us-10-032-159a-17.rng, p. 2-3.

* cited by examiner

```
147 atgtcggactacgagaacgatgacgagtgctggaacgtcctggag     CARD domain
    M  S  D  Y  E  N  D  D  E  C  W  N  V  L  E
192 ggcttccgggtgacgctcacctcggtcatcgaccctcacgcatc
    G  F  R  V  T  L  T  S  V  I  D  P  S  R  I
237 acaccttacctgcggcagtgcaaggtcctgaaccctgatgatgag
    T  P  Y  L  R  Q  C  K  V  L  N  P  D  D  E
282 gagcaggtgctcagcgaccccaacctggtcatccgaaacggaaa
    E  Q  V  L  S  D  P  N  L  V  I  R  K  R  K
327 gtgggtgtgctcctggacatcctgcagcggaccggccacaagggc
    V  G  V  L  L  D  I  L  Q  R  T  G  H  K  G
372 tacgtggccttcctcgagagcctggagctctactacccgcagctg
    Y  V  A  F  L  E  S  L  E  L  Y  Y  P  Q  L
417 tacaagaaggtcacaggcaaggagccggcccgcgtcttctccatg
    Y  K  K  V  T  G  K  E  P  A  R  V  F  S  M
462 atcatcgacgcgtccggggagtcaggcctgactcagctgctgatg
    I  I  D  A  S  G  E  S  G  L  T  Q  L  L  M
507 actgaggtcatgaagctgcagaagaaggtgcaggacctgaccgcg
    T  E  V  M  K  L  Q  K  K  V  Q  D  L  T  A
552 ctgctgagctccaaagatgacttcatcaaggagctgcgggtgaag
    L  L  S  S  K  D  D  F  I  K  E  L  R  V  K
597 gacagcctgctgcgcaagcaccaggagcgtgtgcagaggctcaag    FILAMENT domain
    D  S  L  L  R  K  H  Q  E  R  V  Q  R  L  K
642 gaggagtgcgaggccggcagccgcgagctcaagcgctgcaaggag
    E  E  C  E  A  G  S  R  E  L  K  R  C  K  E
687 gagaactacgacctggccatgcgcctggcgcaccagagtgaggag
    E  N  Y  D  L  A  M  R  L  A  H  Q  S  E  E
732 aagggcgccgcgctcatgcggaaccgtgacctgcagctggagatt
    K  G  A  A  L  M  R  N  R  D  L  Q  L  E  I
777 gaccagctcaagcacagcctcatgaaggccgaggacgactgcaag
    D  Q  L  K  H  S  L  M  K  A  E  D  D  C  K
822 gtggagcgcaagcacacgctgaagctcaggcacgccatggagcag
    V  E  R  K  H  T  L  K  L  R  H  A  M  E  Q
867 cggcccagccaggagctgctgtgggagctgcagcaggagaaggcc
    R  P  S  Q  E  L  L  W  E  L  Q  Q  E  K  A
912 ctgctccaggcccgggtgcaggagctggaggcctccgtccaggag
    L  L  Q  A  R  V  Q  E  L  E  A  S  V  Q  E
957 gggaagctggacaggagcagcccctacatccaggtactggaggag
    G  K  L  D  R  S  S  P  Y  I  Q  V  L  E  E
1002 gactggcggcaggcgctgcgggaccaccaggagcaggccaacacc
    D  W  R  Q  A  L  R  D  H  Q  E  Q  A  N  T
1047 atcttctccctgcgcaaggacctccgccagggcgaggcccgacgc
    I  F  S  L  R  K  D  L  R  Q  G  E  A  R  R
1092 ctccggtgcatggaggagaaggagatgttcgagctgcagtgcctg
    L  R  C  M  E  E  K  E  M  F  E  L  Q  C  L
1137 gcactacgtaaggactccaagatgtacaaggaccgcatcgaggcc
    A  L  R  K  D  S  K  M  Y  K  D  R  I  E  A
1182 atcctgctgcagatggaggaggtcgccattgagcgggaccagagc
    I  L  L  Q  M  E  E  V  A  I  E  R  D  Q  S
1227 acacaaatggaggggctgtga 1247
    T  Q  M  E  G  L  *
```

FIGURE 1

```
  1 atggatgactacatggagacgctgaaggatgaagaggacgccttg          CARD domain
    M  D  D  Y  M  E  T  L  K  D  E  E  D  A  L
 46 tgggagaatgtggagtgtaaccggcacatgctcagccgctatatc
    W  E  N  V  E  C  N  R  H  M  L  S  R  Y  I
 91 aaccctgccaagctcacgccctacctgcgtcagtgtaaggtcatt
    N  P  A  K  L  T  P  Y  L  R  Q  C  K  V  I
136 gatgagcaggatgaagatgaagtggttaatgccctatgctgcca
    D  E  Q  D  E  D  E  V  L  N  A  P  M  L  P
181 tccaagatcaaccgagcaggccggctgttggacattctacatacc
    S  K  I  N  R  A  G  R  L  L  D  I  L  H  T
226 aagggcaaaggggctatgtggtcttcttggagagcctagaattt
    K  G  Q  R  G  Y  V  V  F  L  E  S  L  E  F
271 tattacccagaactgtacaaactggtgactgggaaagagcccact
    Y  Y  P  E  L  Y  K  L  V  T  G  K  E  P  T
316 cggagattctccaccattgtggtggaggaaggccacgagggcctc
    R  R  F  S  T  I  V  V  E  E  G  H  E  G  L
361 acgcacttcctgatgaacgaggtcatcaagctgcagcagcagatg
    T  H  F  L  M  N  E  V  I  K  L  Q  Q  Q  M          ERM (ezrin) domain
406 aaggccaaggacctgcaacgctgcgagctgctggccaggttgcgg
    K  A  K  D  L  Q  R  C  E  L  L  A  R  L  R
451 cagctggaggatgagaagaagcagatgacgctgacgcgcgtggag
    Q  L  E  D  E  K  K  Q  M  T  L  T  R  V  E
496 ctgctaaccttccaggagcggtactacaagatgaaggaagagcgg
    L  L  T  F  Q  E  R  Y  Y  K  M  K  E  E  R
541 gacagctacaatgacgagctggtcaaggtgaaggacgacaactac
    D  S  Y  N  D  E  L  V  K  V  K  D  D  N  Y
586 aacttagccatgcgctacgcacagctcagtgaggagaagaacatg
    N  L  A  M  R  Y  A  Q  L  S  E  E  K  N  M
631 gcggtcatgaggagccgagacctccaactcgagatcgatcagcta
    A  V  M  R  S  R  D  L  Q  L  E  I  D  Q  L
676 aagcaccggttgaataagatggaggaggaatgtaagctggagaga
    K  H  R  L  N  K  M  E  E  E  C  K  L  E  R
721 aatcagtctctaaaactgaagaatgacattgaaaatcggcccaag
    N  Q  S  L  K  L  K  N  D  I  E  N  R  P  K
766 aaggagcaggttctggaactggagcgggagaatgaaatgctgaag
    K  E  Q  V  L  E  L  E  R  E  N  E  M  L  K
811 accaaaaaccaggagctgcagtccatcatccaggccgggaagcgc
    T  K  N  Q  E  L  Q  S  I  I  Q  A  G  K  R
856 agcctgccagactcagacaaggccatcctggacatcttggaacac
    S  L  P  D  S  D  K  A  I  L  D  I  L  E  H
901 gaccgcaaggaggccctggaggacaggcaggagctggtcaacagg
    D  R  K  E  A  L  E  D  R  Q  E  L  V  N  R
946 atctacaacctgcaggaggaggcccgccaggcagaggagctgcga
    I  Y  N  L  Q  E  E  A  R  Q  A  E  E  L  R
991 gacaagtacctggaggagaaggaggacctggagctcaagtgctcg
    D  K  Y  L  E  E  K  E  D  L  E  L  K  C  S
1036 accctggggaaggactgtgaaatgtacaagcaccgcatgaacacg
    T  L  G  K  D  C  E  M  Y  K  H  R  M  N  T
1081 gtcatgctgcagctggaggaggtggagcgggagcgggaccaggga
    V  M  L  Q  L  E  E  V  E  R  E  R  D  Q  G
```

FIGURE 2A 1126 caggctgtggccttccagggacactgcatcaaagctctcaacaca
     Q  A  V  A  F  Q  G  H  C  I  K  A  L  N  T
1171 gagcctgccactagcaagggtcggaccatcggctctgtgatcgcg
     E  P  A  T  S  K  G  R  T  I  G  S  V  I  A
1216 ttaatgaagaaggccttccactcccagatgaagctcagacacag
     L  M  K  K  A  F  H  S  R  D  E  A  Q  T  Q
1261 tactcgcagtgcttaatcgaaaaggacaagtacaggaagcagatc
     Y  S  Q  C  L  I  E  K  D  K  Y  R  K  Q  I
1306 cgcgagctggaggagaagaacgacgagatgaggatcgagatggtg
     R  E  L  E  E  K  N  D  E  M  R  I  E  M  V
1351 cggcgggaggcctgcatcgtcaacctggagagcaagctgcggcgc
     R  R  E  A  C  I  V  N  L  E  S  K  L  R  R
1396 ctctccaaggacagcaacaacctggaccagagtctgcccaggaac
     L  S  K  D  S  N  N  L  D  Q  S  L  P  R  N
1441 ctgccagtaaccatcatctctcaggactttggggatgccagcccc
     L  P  V  T  I  I  S  Q  D  F  G  D  A  S  P
1486 aggaccaatggtcaagaagctgacgattcttccacctcggaggag
     R  T  N  G  Q  E  A  D  D  S  S  T  S  E  E
1531 tcacctgaagacagcaagtacttcctgccctaccatccgccccag
     S  P  E  D  S  K  Y  F  L  P  Y  H  P  P  Q
1576 cgcaggatgaacctgaagggcatccagctgcagagagccaaatcc
     R  R  M  N  L  K  G  I  Q  L  Q  R  A  K  S
1621 cccatcagcctgaagcgaacatcagatttcaagccaaggggcac
     P  I  S  L  K  R  T  S  D  F  Q  A  K  G  H
1666 gaggaagaaggcacggacgccagccctagctcctgcggatctctg
     E  E  G  T  D  A  S  P  S  S  C  G  S  L
1711 cccatcaccaactccttcaccaagatgccccccggagccgcagc
     P  I  T  N  S  F  T  K  M  P  P  R  S  R  S
1756 agcatcatgtcaatcaccgccgagcccccgggaaacgactccatc
     S  I  M  S  I  T  A  E  P  P  G  N  D  S  I
1801 gtcagacgctacaaggaggacgcgcccatcgcagcacagtcgaa
     V  R  R  Y  K  E  D  A  P  H  R  S  T  V  E
1846 gaagacaatgacagcggcgggtttgacgccttagatctggatgag
     E  D  N  D  S  G  G  F  D  A  L  D  L  D  E
1891 ctggcagcaggggagactgtggctcagagtcctccaggtgtgccc
     L  A  A  G  E  T  V  A  Q  S  P  P  G  V  P
1936 tgccagcccctctcttccagggctcccccagcctttgccagcta
     C  Q  P  P  L  F  Q  G  S  P  S  L  C  Q  L
1981 aggctgccaaccgatgaaacgaaagatgagtggtcctccttaatg
     R  L  P  T  D  E  T  K  D  E  W  S  S  L  M
2026 gggaagcatcagcgctaccaagtgttaaagagagatgacagtcac
     G  K  H  Q  R  Y  Q  V  L  K  R  D  D  S  H
2071 gaacgctactccttcggacccctcctccatccactcctcctcctcc
     E  R  Y  S  F  G  P  S  S  I  H  S  S  S  S
2116 tcccaccaatccgagggcctggatgcctacgacctggagcaggtc
     S  H  Q  S  E  G  L  D  A  Y  D  L  E  Q  V
2161 aacctcatgttcaggaagttctctctggaaagaccttccggcct    PDZ domain
     N  L  M  F  R  K  F  S  L  E  R  P  F  R  P
2206 tcggtcacctctgtggggcacgtgcggggcccagggccctcggtg
     S  V  T  S  V  G  H  V  R  G  P  G  P  S  V
2251 cagcacacgacgctgaatggcgacagcctcacctcccagctcacc
     Q  H  T  T  L  N  G  D  S  L  T  S  Q  L  T
2296 ctgctgggggcaacgcgcgaggagcttcgtgcactcggtcaag
     L  L  G  G  N  A  R  G  S  F  V  H  S  V  K
2341 cctggctctctggccgagaaagccggcctccgtgagggccaccag
     P  G  S  L  A  E  K  A  G  L  R  E  G  H  Q
2386 ctgctgctgctagaaggctgcatccgaggcgagaggcagagtgtc
     L  L  L  L  E  G  C  I  R  G  E  R  Q  S  V
2431 ccgttggacacatgcaccaaagaggaagcccactggaccatccag
     P  L  D  T  C  T  K  E  E  A  H  W  T  I  Q
2476 agggtgcagcggccccgtcacgctgcactacaaggtcaaccacgaa
     R  C  S  G  P  V  T  L  H  Y  K  V  N  H  E
2521 gcccagcagaaaatccgtgggcctgcagaatatgatgtgggcagc

FIGURE 2B

```
             A  Q  Q  K  I  R  G  P  A  E  Y  D  V  G  S
      2566 acctccaaagcccggagctgcgcagcagcacagccctgcaagtct
             T  S  K  A  R  S  C  A  A  A  Q  P  C  K  S
      2611 ggaattccagggaaagaaagttcattccggcagggg taccggaag
             G  I  P  G  K  E  S  S  F  R  Q  G  Y  R  K
      2656 ctggtgaaggacatggaggacggcctgatcacatcggggg actcg
             L  V  K  D  M  E  D  G  L  I  T  S  G  D  S
      2701 ttctacatccggctgaacctgaacatctccagccagctggacgcc
             F  Y  I  R  L  N  L  N  I  S  S  Q  L  D  A
      2746 tgcaccatgtccctgaagtgtgacgatgttgtgcacgtccgtgac
             C  T  M  S  L  K  C  D  D  V  V  H  V  R  D
      2791 accatgtaccaggacaggcacgagtggctgtgcgcgcgggtcgac
             T  M  Y  Q  D  R  H  E  W  L  C  A  R  V  D
      2836 cctttcacagaccatgacctggatatgggcaccatacccagctac
             P  F  T  D  H  D  L  D  M  G  T  I  P  S  Y
      2881 agccgagcccagcagctcctcctggtgaaactgcagcgcctgatg
             S  R  A  Q  Q  L  L  L  V  K  L  Q  R  L  M
      2926 caccgaggcagccgggaggaggtagacggcacccaccacaccctg
             H  R  G  S  R  E  E  V  D  G  T  H  H  T  L
      2971 cgggcactccggttcgtcagcaggtccgagaacaagtataagcgg
             R  A  L  R  F  V  S  R  S  E  N  K  Y  K  R
      3016 atgaacagcaacgagcgggtccgcatcatctcggggagtccgcta
             M  N  S  N  E  R  V  R  I  I  S  G  S  P  L
      3061 gggagcctggcccggtcctcgctggacgccaccaagctcttgact
             G  S  L  A  R  S  S  L  D  A  T  K  L  L  T
      3106 gagaagcaggaagagctggaccctgagagcgagctgggcaagaac
             E  K  Q  E  E  L  D  P  E  S  E  L  G  K  N
      3151 ctcagcctcatcccctacagcctggtacgcgccttctactgcgag
             L  S  L  I  P  Y  S  L  V  R  A  F  Y  C  E
      3196 cgccgccggcccgtgctcttcacacccaccgtgctggccaagacg
             R  R  R  P  V  L  F  T  P  T  V  L  A  K  T
      3241 ctggtgcagaggctgctcaactcgggaggtgccatggagttcacc
             L  V  Q  R  L  L  N  S  G  G  A  M  E  F  T
      3286 atctgcaagtcagatatcgtcacaagagatgagttcctcagaagg
             I  C  K  S  D  I  V  T  R  D  E  F  L  R  R
      3331 cagaagacggagaccatcatctactcccgagagaagaaccccaac
             Q  K  T  E  T  I  I  Y  S  R  E  K  N  P  N
      3376 gcgttcgaatgcatcgcccctgccaacattgaagctgtggccgcc
             A  F  E  C  I  A  P  A  N  I  E  A  V  A  A
      3421 aagaacaagcactgcctgctggaggctgggatcggctgcacaaga
             K  N  K  H  C  L  L  E  A  G  I  G  C  T  R
      3466 gacctgatcaagtccaacatctaccccatcgtgctcttcatccgg
             D  L  I  K  S  N  I  Y  P  I  V  L  F  I  R
      3511 gtgtgtgagaagaacatcaagaggttcagaaagctgctgccccga
             V  C  E  K  N  I  K  R  F  R  K  L  L  P  R
      3556 cctgagacggaggaggagttcctgcgcgtgtgccggctgaaggag
             P  E  T  E  E  E  F  L  R  V  C  R  L  K  E
      3601 aaggagctggaggccctgccgtgcctgtacgccacggtggaacct
             K  E  L  E  A  L  P  C  L  Y  A  T  V  E  P
      3646 gacatgtggggcagcgtagaggagctgctccgcgttgtcaaggac
             D  M  W  G  S  V  E  E  L  L  R  V  V  K  D
      3691 aagatcggcgaggagcagcgcaagaccatctgggtggacgaggac
             K  I  G  E  E  Q  R  K  T  I  W  V  D  E  D
      3736 cagctgtga 3744
             Q  L  *
```

FIGURE 2C

```
  1 atgggggaactgtgccgcagggactccgcactcacggcactggac
    M  G  E  L  C  R  R  D  S  A  L  T  A  L  D
 46 gaggagacactgtgggagatgatggagagccaccgccacaggatc
    E  E  T  L  W  E  M  M  E  S  H  R  H  R  I      CARD domain
 91 gtacgctgcatctgccccagccgcctcaccccctacctgcgccag
    V  R  C  I  C  P  S  R  L  T  P  Y  L  R  Q
136 gccaaggtgctgtgccagctggacgaggaggaggtgctgcacagc
    A  K  V  L  C  Q  L  D  E  E  E  V  L  H  S
181 ccccggctcaccaacagcgccatgcgggccggcacttgctggat
    P  R  L  T  N  S  A  M  R  A  G  H  L  L  D
226 ttgctgaagactcgagggaagaacggggccatcgccttcctggag
    L  L  K  T  R  G  K  N  G  A  I  A  F  L  E
271 agcctgaagttccacaaccctgacgtctacaccctggtcaccggg
    S  L  K  F  H  N  P  D  V  Y  T  L  V  T  G
316 ctgcagcctgatgttgacttcagtaactttagcggtgagagctcc
    L  Q  P  D  V  D  F  S  N  F  S  G  E  S  S
361 gactttgacggtttggcaggcacttctaggaacctcaggctcctg
    D  F  D  G  L  A  G  T  S  R  N  L  R  L  L
406 gtaaccccagnn 417
    V  T  P  X
```

```
  1 msdyenddec wnvlegfrvt ltsvidpsri tpylrqckvl npddeeqvls dpnlvirkrk
 61 vgvlldilqr tghkgyvafl eslelyypql ykkvtgkepa rvfsmiidas gesgltqllm
121 tevmklqkkv qdltallssk ddfikelrvk dsllrkhqer vqrlkeecea gsrelkrcke
181 enydlamrla hqseekgaal mrnrdlqlei dqlkhslmka eddckverkh tlklrhameq
241 rpsqellwel qqekallqar vqeleasvqe gkldrsspyi qvleedwrqa lrdhqeqant
301 ifslrkdlrq gearrlrcme ekemfelqcl alrkdskmyk drieaillqm eevaierdqs
361 tqmegl
```

GI "10436237"

```
   1 atcatcagga agtgcacagg cgtccggcgt gctcctccct ccctgcagcc ccgggcagca
  61 tctcccagag gctccgcggc ccaggctcct ggtgtgtctg cagtgcaggt ggctcctgga
 121 agaccctcag cctgcctgct gaggccatgt cggactacga gaacgatgac gagtgctgga
 181 acgtcctgga gggcttccgg gtgacgctca cctcggtcat cgacccctca cgcatcacac
 241 cttacctgcg gcagtgcaag gtcctgaacc ctgatgatga ggagcaggtg ctcagcgacc
 301 ccaacctggt catccgcaaa cggaaagtgg gtgtgctcct ggacatcctg cagcggaccg
 361 gccacaaggg ctacgtggcc ttcctcgaga gcctggagct ctactacccg cagctgtaca
 421 agaaggtcac aggcaaggag ccggcccgcg tcttctccat gatcatcgac gcgtccgggg
 481 agtcaggcct gactcagctg ctgatgactg aggtcatgaa gctgcagaag aaggtgcagg
 541 acctgaccgc gctgctgagc tccaaagatg acttcatcaa ggagctgcgg gtgaaggaca
 601 gcctgctgcg caagcaccag gagcgtgtgc agaggctcaa ggaggagtgc gaggccggca
 661 gccgcgagct caagcgctgc aaggaggaga actacgacct ggccatgcgc ctggcgcacc
 721 agagtgagga aaagggcgcc gcgctcatgc ggaaccgtga cctgcagctg gagattgacc
 781 agctcaagca cagcctcatg aaggccgagg acgactgcaa ggtggagcgc aagcacacgc
 841 tgaagctcag gcacgccatg gagcagccgc ccagccagga gctgctgtcg gagctgcagc
 901 aggagaaggc cctgctccag gcccgggtgc aggagctgga ggcctccgtc caggagggga
 961 agctggacag gagcagcccc tacatccagg tactggagga ggactggcgg caggcgctgc
1021 gggaccacca ggagcaggcc aacaccatct tctccctgcg caaggacctc cgccagggcg
1081 aggcccgacg cctccggtgc atggaggaga aggagatgtt cgagctgcag tgcctggcac
1141 tacgtaagga ctccaagatg tacaaggacc gcatcgaggc catcctgctg cagatggagg
1201 aggtcgccat tgagcgggac cagagcacac aaatggaggg gctgtgacca gcctccgcgc
1261 ccagcggctt gacgtcctcc ggagcctctg cttggagttg ggcggccggg ccgagggccc
1321 agggcaagct tggggccctc actgagggtc ggccttgtgc tgtccgtca ggccatagcc
1381 acgcgggagg agctgcacgc acagcacgcc cggggcctgc aggagaagga cgcgctgcgc
1441 aagcacgtgc gggagctggg cgagaaggcg gatgagctgc agctgcaggt gttccagtgt
1501 gaggcgcagc tactggccgt ggagggcagg ctcaggcggc agcagctgga cgctcgtc
1561 ctgagctccg acctggaaga tggctcaccc aggaggtccc aggagctctc actccccag
1621 gacctggagg cacccagct ctcagacaaa ggctgccttg ccggcggggg gagcccgaaa
1681 cagccctttg cagctctgca ccaggagcag gttttgcgga accccatga cgcaggcctg
1741 agcagcgggg agccgcccga aaggagcgg ccgcgcctca agagagttt tgagaactac
1801 cgcaggaagc gcgccctcag gaagatgcag aaaggatggc ggcaggggga ggaggaccgg
1861 gagaacacca cgggcagcga caacaccgac actgagggct cctagccgca gcagacttcc
1921 ccgagccgtc gctgacttgg cctggaacga ggaatctggt gccctgaaag gcccagccgg
1981 actgccgggc attggggccg tttgttaagc ggcactcatt ttgcggaggc catgcgggtg
2041 ctcaccaccc ccatgcacac gccatctgtg taacttcagg atctgttctg tttcaccatg
2101 taacacacaa tacatgcatg cattctatta gtgttagaaa acacagctgc gtaaataaac
2161 agcacgggtg acccgc
```

FIGURE 4

CARD1OX ESTs

GI"9094656"

GAGAGGCTCCGCGGCCCAGGCTCCTGGTGTGTCTGCAGTGCAGGTGGCTCCTGGAAGACC
CTCAGCCTGCCTGCTGAGGCCATGTTTGACTACGAGAACGATGACGAGTGCTGGAGCGTC
CTGGAGGGCTTCCGGGTGACGCTCACCTCGGTCATCGACCCCTCACGCATCACACCTTAC
CTGCGGCAGTGCAAGGTCCTGAACCCCGATGATGAGGAGCAGGTGCTCAGCGACCCCAAC
CTGGTCATCCGCAAACGGAAAGTGGGTGTGCTCCTGGACAT

GI"7132200"

GGGACAGCCTGCTCCGCAAGCACCAAGAGCGGGTGCAGAAGATGAGGGAGGAGAGGGACA
GTCTAAGCAAGGAGCTGCGGAAGTGCAAGGATGAGAACTACAACCTGGCAATGAGCTATG
CCAGACAGAGCGAGGAGAAGAGCAGTGCCCTCATGAAGAACAGGGACCTGCTCCTAGAGA
TTGATAGCTTGAAGCATAGCCTCATGAAGGCTGAGGACGACTGCAAACTAGAGCGTAAGC
ACTCGATGAAACTGAAGCATGCCATAGAACAACGTCCGAGCCATGAAGTGATGTGGGAGA
TCCAGCAGGAGAAGGAGCTGCTTTTGGCCAAGAATCAGGAGCTGGAGAACACTCTTCAGG
TTGCCAGGGAACAGAATTTGGAGACGAGTCTCTCCCATGAGACTGTGCAGAATGACTGCA
GCCAGGTGCTGGAGCGCCAGGACCTGCTGAACACCCTGTACCACCTTCGCAAGGAGCTGC
GCCAAGCCGAGGTGCTTCGAGACAAGTTCGAGGAGTGCAGCTCAGCCCACGAGGAGCTGT
CCGAGAAGGAGCGGAGGAGGATGAAGGACTGCTTTGAGCGTTACCGCAGGAAGCGCGCCC
TGCGCAGAGCGCCCGCGGGCCCGCCGCCCCGAGGCCGACTGGGAGCCGAGCACGGGCAGC
GACAACACGGACACCGAGGGCAGCTAGGGGCCGGCCGAGCTTTCGAGTTTGCAGCTGGAT
CCGTCAATAAACAG

GI"5884878"

TGAACACCCTGTACCACCTTCGCAAGGAGCTGCGCCAAGCCGAGGTGCTCCGAGACAAGT
ATGCAGAGGAAAAAGAAATACTTGAACTACAGTGCACATCTCTGAGGAAGGACTCCCAGA
TGTATAAAAAACGGATGGAAGCTGTCTTAGAGCAGATGGAGGAAGTGGCTTCGGAAAGAG
ACCAGGCACTGCTGACCAGAGAACAGTTCTACCCACAGTACTCCAAGAACCTTGTTGAGA
GGGACACTTATCGGAAGCAGATTCGGGAGCTGGGGGAGCGATGCGATGAGCTGCAGCTGC
AGCTCTTCCAAAAGGAGGGTCAGCTACTGGCTACTGAAGCCAAGCTGAAAAGACTGCAAC
TGGAGCTGCCTGCACTGACTTCTGACCTGGATGACACTCCTCCAGAGATCCCAGGTCTTA
CTCTCATGGTCATCTAGACGAAGATCGCACCTGACTAAAAAAGACGCTGTTAAGGAAAAC
CAGCAATCAGCATGCAAGAAACATCTGACGCAGATCACCACTTCGAGGATGCACTAACCA
CAAGACTTCGAGAAGACGGAGAGATAAGGATGCTTGAGCGTACGAGTCGGCCGATCCGCG
CCCCCCCTCCGCGCTCCTTCCGTGGCTCGT

FIGURE 5

CARD11X ESTs

GI"6926669"

CACGAGGGAAATGTACAAGCACCGCATGAACACGGTCATGCTGCACCTGGAGGAGGTGGA
GCGGGAGCGGGACCAGGCCTTCCACTCCCGAGATGAAGCTCAGACACAGTACTCGCAGTG
CTTAATCGAAAAGGACAAGTACAGGAAGCAGATCCGCGAGCTGGAGGAGAAGAACGACGA
GATGAGGATCGAGATGGTGCGGCGGGAGGCCTGCATCGTCAACCTGGAGAGCAAGCTGCG
GCGCCTCTCCAAGGACAGCAACAACCTGGACCAGAGTCTGCCCAGGAACCTGCCAGTAAC
CATCATCTCTCAGGACTTTGGGGATGCCAGC

GI"6143407"

TTTTTTTTTTTTTTTCTCTCCTGCCTCCTCTGGCCTTCGGACTCCTGCCCGCGCCGCCCG
CAGCCCCCTCCCGGCCCTGCAGCCCCTGGGCGGGCGGCGCCCCTCGGAGGACGGCTCCGG
GCCCGGGGGGACGGAGGGCCTGGTCGCCTGGAGGAAGCCGGAGGCCTGCGTGGAGGAGGC
GCCCCGCGCAGCTGGCTGGCGGAGCATGAGCGCCCCAGATCCCAAGCACTGCAAGTCCAG
ATGCAACGGGAGCCTGGCTCAAGGGACGACAAGATCCAGCCGGAAAGTGTAGAAGTCACA
CCCCAATGGCGGGATAGCAGCCCCTGTGTGTGAGCACCCCTCCATGCCAGGAGGAGGGCC
AGAGATGGATGACTACATGGAGACCCTGAAGGATGAAGAGGACCCCTTGTGGGACAATGT
GGAGTGTAACCGGCACATGCTCAACCGCTATATCAACCCTGCCAAGCTCACGCCCTAC

GI"2785620"

GCAGCCCCCTCCCGGCCCTGCAGCCCCTGGCGTGCGGCGCCATCGGAGGACGGCTCCGGG
CCCGGGGGGACGGAGGGCCTGGTCGCCTGGAGGAAGCCGGACGCTGCGTGGAGGAGGCGC
CCCCGGTCTGGTCTGGCGGACGATGAGCGCCCCAGATCCCAAGCACTGCAAGTCCAGATG
CAACGGGAGCCTGGCTCAAGGGACGACAAGATCCAGCCGGAAAGTGTAGAAGTCACACCC
CAATGGCGGGATAGCAGCCCCTGTGTGTGATCACCCCTCCATGCCAGGAGGAGGGCCAGA
GATGGATGACTACATGGAGACGCTGAATGATGAAGAGGACGCCTTGTGGGAGAATGTGGA
GTGTAACCGGCACATGCTCAGCCGCTATATCAACCC

GI"1838222"

AAAAGGAGGAGGGCCAGAGATGGATGACTACATGGAGACGCTGAAGGATGAAGAGGACGC
CTTGTGGGTGAATGTGGAGTGTAACCGGCACATGCTCAGCCGGGTCTCACGAATTCCGCT
GAGTTCTCACGAATTCCGCTGAGGTCTCACGAATTCCGCTGA

GI"6927709"

CACGACGACGGACGCCAGCCCTAGCTCCTGCGGATCTCTGCCCATCACCAACTCCTTCAC
CAAGATGCAGCCCCCCGGAGCCGCAGCAGCATCATGTCAATCACCGCCGAGCCCCCGGG
AAACGACTCCATCGTCAGACGCTACAAGGAGGACGCGCCCCATCGCAGCACAGTCGAAGA
AGACAATGACAGCGGCGGGTTTGACGCCTTAGATCTGGATGATGACAGTCACGAACGCTA
CTCCTTCGGACCCTCCTCCATCCACTCCTCCTCCTCCTCCCACCAATCCGAGGGCCTGGA
TGCCTACGACCTGGAGCAGGTCAACCTCATGTTCAGGAAGTTCTCTCTGGAAAGACCCTT
CCGGCCTTCGGTCACCTCTGTGGGGCACGTTCGGGGCCCAAGGCCCTCGGTGCAGCAC

TCATCCCCTACAGCCTGGTACGCGCCTTCTACTGCGAGCGCCGCCGGCCCGTGCTCTTCA
CACCCACCGTGCTGGCCAAGACGCTGGTGCAGAGGCTGCTCAACTCGGGAGGTGCCATGG
AGTTCACCATCTGCAAGTCAGATATCGTCACAAGAGATGAGTTCCTCAGAAGGCAGAAGA
CGGAGACCATCATCTACTCCCGAGAGAAGAACCCCAACGCGTTCGAATGCATCGCCCCTG
CCAACATCGAAGCTGTGGCCGCCAAGAACAAGCACTGCCTGCTGGAGGCTGGGATCGGCT
GCACAAGAGACTTGATCAAGTCCAACATCTACCCCATCGTGCTCTTCATCCGGGTGTGTG
AGAAGAACATCAAGAGGTTCAGAAAGCTGCTGCCCCGACCTGAGACGGAGGAGGAGTTCC
TGCGCGTGTGCCGGCTGAAGGAGAAGGAGCTGGAGGCCCTGCCGTGCCTGTACGCCACGG
TGGAACCTGACATGTGGGGCAGCGTAGAGGAGCTGCTCCGCGTTGTCAAGGACAAGATCG
GCGAGGAGCAGCGCAAGACCATCTGGGTGGACGAGGACCAGCTGTGAGGCGGGCGCCCTG
GGCAGAGAGA

GI"9142863"

TCATCCCCTACAGCCTGGTACGCGCCTTCTACTGCGAGCGCCGCCGGCCCGTGCTCTTCA
CACCCACCGTGCTGGCCAAGACGCTGGTGCAGAGGCTGCTCAACTCGGGAGGTGCCATGG
AGTTCACCATCTGCAAGTCAGATATCGTCACAAGAGATGAGTTCCTCAGAAGGCAGAAGA
CGGAGACCATCATCTACTCCCGAGAGAAGAACCCCAACGCGTTCGAATGCATCGCCCCTG
CCAACATCGAAGCTGTGGCCGCCAAGAACAAGCACTGCCTGCTGGAGGCTGGGATCGGCT
GCACAAGAGACTTGATCAAGTCCAACATCTACCCCATCGTGCTCTTCATCCGGGTGTGTG
AGAAGAACATCAAGAGGTTCAGAAAGCTGCTGCCCCGACCTGAGACGGAGGAGGAGTTCC
TGCGCGTGTGCCGGCTGAAGGAGAAGGAGCTGGAGGCCCTGCCGTTGCCNTGGTACGCCA
CGGTGGAACCTGACATGTGGGGCAGCGTAGAGGAGCTGCTCCGCGTGTCAGGACAGACGG
CGAGAGCAGCGCAAGA

GI"1761194"

GCTCCTTCAGTTCGTCAGCAGGTCCGAGAACAAGTATAAGCGGATGAACAGCAACGAGCG
GGTCCGATCATCTCGGGGAGTCCGCTAGGAGCCTGGCCCGGTCCTCGCTGGACGCCACCA
AGCTCTTGACTGAGAAGCAGGAAGAGCTGGACCCTGAGAGCGAGCTGGGCAAGAACCTCA
GCCTCATCCCCTACAGCCTGGTACGCGCCTTCTACTGCGAGCGCCGCCGGCCTGTGCTCT
TCACACCCACCGTGCTGGCCAAGACGCTGGTGCAGAGGCTGCTCAACTCGGGAGGTGCCA
TGGAGTTCACCATCTGCAAGTCAGATATCGTCACAAGAGATGAGTTCCTCAGAAGGCAGA
AGACGGAGACCATCATCTACTCCCGAGAGA

GI"8151876"

AGAGACTTGATCAAGTCCAACATCTACCCCATCGTGCTCTTCATCCGGGTGTGTGAGAAG
AACATCAAGAGGTTCAGAAAGCTGCTGCCCCGGCCTGAGACGGAGGAGGAGTTCCTGCGC
GTGTGCCGGCTGAAGGAGAAGGAGCTGGAGGCCCTGCCGTGCCTGTACGCCACGGTGGAA
CCTGACATGTGGGGCAGCGTAGAGGAGCTGCTCCGCGTTGTCAAGGACAAGATCGGCGAG
GAGCAGCGCAAGACCATCTGGGTGGACGAGGACCAGCTGTGAGGCGGGCGCCCTGGGCAG
AGAGACTCTGTGGCGCGGGGCATCCTATGAGGCAGGCACCCTGGGCAGAGAGATGTAGTG
GGTGCGGGGGGATCCTGTGGCCCACAGAGCTGCCCCAGCAGACGCTCCGCCCCACCCGGT
GATGGAGCCCCGGGGGACAGTCGTGCCTGGGGAGGAGCAGGGTACAGCCCATTCCCCCA
GCCCTGGCTGACCTGGCCTAGCAGTTTTGGCCCTGCTGGCCTTAGCAGGGAGACAGGGGA
GCAAAGAACGCCAAGCCGGGAGGCCCAAGCCAGCCGGCTCTCGAGGGGGGCCCGGTCC
CCATTTTGCCCTTTATGAGC

AAGAGACTTGATCAAGTCCAACATCTACCCCATCGTGCTCTNTCATCCGGGTGTGTGAGA
AGAACATCAAGAGGTTCAGAAAGCNGCTGCCCCGGCCTGAGACGGAGGNGNAGTTCCTGC
GCGTGTGCCGGCTGAAGGNGAAGGAGCTGGAGGCCCTGCCGTGCCTGTACGCGACGGTGG
AACCTGACATGTGGGGCAGCGTAGAGGAGCTGCTCCGCGTTNTATAAGGACAAGATCGGT
GAGNAGCAGCGCAAGACCATCTNGGTAGACGAGGACCAGCTTT

GI"8042493"

GTGTACTGCCTTCTGAGGAACTCATCTCTGTGACGATATCTGACTTGCAGATGGTGAACT
CCATGGCACCTCCCGAGTTGAGCAGCCTCTGCACCAGCGTCTTGGCCAGCACGGTGGGTG
TGAAGAGCACGGGCCGGCGGCGCTCGCAGTAGAAGGCGCGTACCAGGCTGTAGGGGATGA
GGCTGAGGTTCTTGCCCAGCTCGCTCT

GI"2079290"

GACTTGATCAAGTCCAACATCTACCCCATCGTGCTCTTCATCCGGGTGTGTGAGAAGAAC
ATCAAGAGGTTCAGAAAGCTGCTGCCCCGGCCTGAGACTGGAGGAGGAGTTCCTGCGCGT
GTGCCGGCTGAAGGAGAAGGAGCTGGAGGCCCTGCGATGCCTGTACGCCACGGTGGAACC
TGACATGTGGGG

GI"7044777"

GAAATAATAATACATTTTAATGCAAGAGAAATCATAGCCTGGTACACACCCCTTCCCCGA
TCTGTCCTGCCTGGGGATGTGTTTATGGTGAGTGTGTCCCCAGGACTGGTAGTCACCTGG
CTGTCCGGGTCCCCGCCCTACTGGCGGCAGCATGCCTGTCCCCAGCATTACATTCAACTG
CTGCTCTGGCTCTCGAGAGGCCGGCTGGCCTCNGGCCTTCCGGCTTGGCGTTCTTTGCTC
CCCTGTCTCCCTGCTAAGGCCAGCAGGGCCAAACTGCTAGGCCAGGTCAGCCAGGGCTGG
GGGAATGGGCTGTACCCTGCTCCTCCCCAGGCACGACTGTCCCCCCGGGGCTCCATCACC
GGGTGGGGCGGAGCGTCTGCTGGGGCAGCTCTGTGGGCCACAGGATCCCCCCGCACCCAC
TGCATCTCTCTGCCCATGGTGCCTGCCTCATAGGATGCCCCGCGCCACAGAGTCTATATG
TCCAGGGCGCCCGCCTCACAGCTGGTCCTCGTCCACCCAGATGGTCTTGCGCTGCTCCTC
GCCGATCTTGTCCTTGACATCGCGGAGCAGCTCCTTTACGCTGCCCCACATGTCAGGTGC
CCCCG

FIGURE 6C

CARD 12X EST

GI"10316320"

```
TCATGCCCAGCTCCGTCCCACCCAGCAGCCCGCAGAGAAAGGAGGCAGCTGGCACCACAC
TGGGCTTTGGAGACACTGCGGGGACTGTGGACCCCACCCTGCTGCACGGAGCTCCTGCAA
AAGCAAACCTGAGAACCTTGGGTCCTCCCAGCGCCCAGCCATGGGGGAACTGTGCCGCAG
GGACTCCGCACTCACGGCACTGGACGAGGAGACACTGTGGGAGATGATGGAGAGCCACCG
CCACAGGATCGTACGCTGCATCTGCCCCAGACGACATTAACCCCTATACTGTGACGCACA
GCGCCAGAGGCTGGCTGCTGACCATGGATGGACCGAGGAGGGAGGTTGCTGCACCAGCGC
CCACGAGACATCAACAACAGACGCACACTGCGGGGCCGGGCACATAGCGTGGCCTCGCGC
TAGAAAGACATCAGAGGAGAAAGAAGCGGGGGCCCACTCGCACTCACCGTGAGTAGACGC
CATGCACAGTACCACCAAACCCATGAGCGCTACTACAACCCATGGGTCACCAGGGCATGA
CAGCCTGGATGCATAGACATAACAAGTAACTTCTACTAGCCAGGTCCTCATGCGAAGACC
ATCCCAAGCCTGACCCGACATGCCCTGGACATGGGCCCACTACGCGCAGACCATGCAGC
GAGAGACGCATGACACCAGGCAACAACGCGGGCCACGAACGCGAGCGTTGCCTGCATCGA
CGGGCACGGTTGGCCACAGACACGGAATTGCAGCGGAGCCACACGTGGCAGCCCCTGAGG
CCCGACGACACCCGGTGCACCGAAGGGGCCATGGCAACCACGACCTGGCAGGCTTGACAC
ACCAAGCGCCATACCACGCGCGTGAAAGGGTACAGAGGCACCAACTACCCAGTGCAAGCG
CAGTTCTTGCAAGGCGATGCCAAGGGAACGGCACGACATGACGACACCGCAGTACTCTGT
GAGGAAACCATCTTAGCAAGATGACAGCCTTGACAGGAAACAACGACACGAAGTGCCTGT
CTCGCAACGCATGACAGAAGACCTGTCGCATATAAAGTAAATGTGATACTAATAGAAAGC
AAGAAGGTTGACACTGAAAGACACACATATGAGTATAACTCGAGTATGCAACGTGAACAT
G
```

FIGURE 7

CARD-DOMAIN CONTAINING POLYPEPTIDES, ENCODING NUCLEIC ACIDS, AND METHODS OF USE

This application is a continuation of U.S. Ser. No. 10/961,569, filed Oct. 8, 2004, which is a divisional of U.S. Ser. No. 10/032,159, filed Dec. 19, 2001, now abandoned which claims the benefit of U.S. Provisional Application No. 60/257,457, filed Dec. 21, 2000, each of which is incorporated herein by reference in its entirety.

This invention was made with United States Government support under grant number DBI-0078731 awarded by the National Science Foundation. The U.S. Government has certain rights in this invention.

BACKGROUND OF THE INVENTION

1. Field of the Invention

This invention relates generally to the fields of molecular biology and molecular medicine and more specifically to the identification of proteins involved in programmed cell death, cytokine processing and receptor signal transduction, and associations of these proteins.

2. Background Information

Programmed cell death is a physiologic process that ensures homeostasis is maintained between cell production and cell turnover in essentially all self-renewing tissues. In many cases, characteristic morphological changes, termed "apoptosis," occur in a dying cell. Since similar changes occur in different types of dying cells, cell death appears to proceed through a common pathway in different cell types.

In addition to maintaining tissue homeostasis, apoptosis also occurs in response to a variety of external stimuli, including growth factor deprivation, alterations in calcium levels, free-radicals, cytotoxic lymphokines, infection by some viruses, radiation and most chemotherapeutic agents. Thus, apoptosis is an inducible event that likely is subject to similar mechanisms of regulation as occur, for example, in a metabolic pathway. In this regard, dysregulation of apoptosis also can occur and is observed, for example, in some types of cancer cells, which survive for a longer time than corresponding normal cells, and in neurodegenerative diseases where neurons die prematurely. In viral infections, induction of apoptosis can figure prominently in the pathophysiology of the disease process, because immune-based for eradication of viral infections depend on elimination of virus-producing host cells by immune cell attack resulting in apoptosis.

Some of the proteins involved in programmed cell death have been identified and associations among some of these proteins have been described. However, additional apoptosis regulating proteins remain to be found and the mechanisms by which these proteins mediate their activity remains to be elucidated. The identification of the proteins involved in cell death and an understanding of the associations between these proteins can provide a means for manipulating the process of apoptosis in a cell and, therefore, selectively regulating the relative lifespan of a cell or its relative resistance to cell death stimuli.

The principal effectors of apoptosis are a family of intracellular proteases known as Caspases, representing an abbreviation for Cysteine Aspartyl Proteases. Caspases are found as inactive zymogens in essentially all animal cells. During apoptosis, the caspases are activated by proteolytic processing at specific aspartic acid residues, resulting in the production of subunits that assemble into an active protease typically consisting of a heterotetramer containing two large and two small subunits. The phenomenon of apoptosis is produced directly or indirectly by the activation of caspases in cells, resulting in the proteolytic cleavage of specific substrate proteins. Moreover, in many cases, caspases can cleave and activate themselves and each other, creating cascades of protease activation and mechanisms for "auto"-activation. Thus, knowledge about the proteins that interact with and regulate caspases is important for devising strategies for manipulating cell life and death in therapeutically useful ways. In addition, because caspases can also participate in cytokine activation and other processes, knowledge about the proteins that interact with caspases can be important for manipulating immune responses and other biochemical processes in useful ways.

One of the mechanisms for regulating caspase activation involves protein-protein interactions mediated by a family of protein domains known as caspase recruitment domains (CARDs). The identification of proteins that contain CARD domains and the elucidation of the proteins with which they interact, therefore, can form the basis for strategies designed to alter apoptosis, cytokine production, cytokine receptor signaling, and other cellular processes.

Thus, a need exists to identify proteins that contain CARD domains. The present invention satisfies this need and provides additional advantages as well.

SUMMARY OF THE INVENTION

In accordance with the present invention, there are provided CARD-containing polypeptides, and functional fragments thereof. The invention also provides nucleic acid molecules encoding CARD-containing polypeptides and active fragments thereof, vectors containing these nucleic acid molecules and host cells containing the vectors. The invention also provides antibodies that can specifically bind to CARD-containing polypeptides, and active fragments thereof.

The present invention also provides a screening assay useful for identifying CARD-associated polypeptides (CAPs), and for identifying agents that can effectively alter the association of a CARD-containing polypeptide with itself or with other proteins. By altering the self-association of a CARD-containing polypeptide or by altering its interaction with other proteins, an effective agent may increase or decrease the level of caspase proteolytic activity or apoptosis in a cell.

The invention also provides methods of altering a biochemical process modulated by a CARD-containing polypeptide, by introducing into the cell and expressing a nucleic acid sequence encoding the polypeptide, or an antisense nucleotide sequence that is complementary to a portion of a nucleic acid molecule encoding the CARD-containing polypeptide. Such biochemical processes include apoptosis, anoikis, cytoskeletal integrity, NF-κB induction, cytokine processing, cytokine receptor signaling, and caspase-mediated proteolysis.

The invention also provides methods for diagnosing or prognosing a pathology characterized by an increased or decreased level of a CARD-containing polypeptide in a cell, by contacting the test sample with an agent that can specifically bind a CARD-containing polypeptide or a nucleotide sequence, and determining the amount of specific binding in the test sample compared to a reference sample.

BRIEF DESCRIPTION OF THE DRAWINGS

FIG. 1 shows the nucleotide sequence (SEQ ID NO:1) and predicted amino acid sequence (SEQ ID NO:2) of CARD-10X. The CARD domain nucleotide sequence (SEQ ID NO:3) and amino acid sequence (SEQ ID NO:4), and the Filament domain nucleotide sequence (SEQ ID NO:5) and amino acid sequence (SEQ ID NO:6), are indicated and underlined.

FIG. 2 shows the nucleotide sequence (SEQ ID NO:7) and predicted amino acid sequence (SEQ ID NO:8) of CARD-11X. The CARD domain nucleotide sequence (SEQ ID NO:9) and amino acid sequence (SEQ ID NO:10), the ERM (ezrin) domain nucleotide sequence (SEQ ID NO:11) and amino acid sequence (SEQ ID NO:12), and the PDZ domain nucleotide sequence (SEQ ID NO:13) and amino acid sequence (SEQ ID NO:14), are indicated and underlined.

FIG. 3 shows the nucleotide sequence (SEQ ID NO:15) and predicted amino acid sequence (SEQ ID NO:16) of CARD-12X. The CARD domain nucleotide sequence (SEQ ID NO:17) and amino acid sequence (SEQ ID NO:18) is indicated and underlined.

FIG. 4 shows the nucleotide sequence (SEQ ID:19) and predicted amino acid sequence (SEQ ID NO:20) of GI 10436238.

FIG. 5 shows the nucleotide sequences of CARD-10X ESTs: GI 9094656 (SEQ ID NO:21), GI 7132200 (SEQ ID NO:22) and GI 5884878 (SEQ ID NO:23).

FIG. 6 shows the nucleotide sequences of CARD-11X ESTs: GI 6926669 (SEQ ID NO:24), GI 6143407 (SEQ ID NO:25), GI 2785620 (SEQ ID NO:26), GI 1838222 (SEQ ID NO:27), GI 6927709 (SEQ ID NO:28), GI 9720543 (SEQ ID NO:29), GI 9142863 (SEQ ID NO:30), GI 1761194 (SEQ ID NO:31), GI 8151878 (SEQ ID NO:32), GI 2007639 (SEQ ID NO:33), GI 8042493 (SEQ ID NO:34), GI 2079290 (SEQ ID NO:35), and GI 7044777 (SEQ ID NO:36).

FIG. 7 shows the nucleotide sequence of a CARD-12X EST: GI 10316320 (SEQ ID NO:37).

DETAILED DESCRIPTION OF THE INVENTION

The present invention provides novel polypeptides involved in programmed cell death, or apoptosis. The principal effectors of apoptosis are a family of intracellular cysteine aspartyl proteases, known as caspases. Caspase activity in the cell is regulated by protein-protein interactions. Similarly, protein-protein interactions influence the activity of other proteins involved in apoptosis. Several protein interaction domains have been implicated in interactions among some apoptosis-regulating proteins. Among these is the caspase recruitment domain, or CARD-containing polypeptide which are so named for the ability of the CARD-containing polypeptides to bind caspases. In addition to their ability to bind caspases, numerous CARD-containing polypeptides bind other proteins, including other CARD-containing polypeptides. Further, CARD-containing polypeptides influence a variety of cellular and biochemical processes beyond apoptosis, including cell adhesion, inflammation and cytokine receptor signaling.

In accordance with the present invention, there are provided isolated CARD-containing polypeptides or functional fragments thereof.

The term "CARD-containing polypeptide" as used herein refers to a protein or polypeptide containing a CARD domain. As used herein, the term "CARD domain" refers to a Caspase Recruitment Domain. A CARD domain is a well known protein domain of approximately 80 amino acids with characteristic sequence conservation as described, for example, in Hofmann et al., *Trends Biochem. Sci.* 22:155-156 (1997). CARD domains have been found in some members of the Caspase family of cell death proteases. Caspases-1, 2, 4, 5, 9, and 11 contain CARD domains near their NH2-termini. These CARD domains mediate interactions of the zymogen inactive forms of caspases with other proteins which can either activate or inhibit the activation of these enzymes.

For example, the CARD domain of pro-caspase-9 binds to the CARD domain of a caspase-activating protein called Apaf-1 (Apoptosis Protease Activating Factor-1). Similarly, the CARD domain of pro-caspase-1 permits interactions with another CARD protein known as Cardiac (also referred to as RIP2 and RICK), which results in activation of the caspase-1 protease (Thome et al., *Curr. Biol.* 16:885-888 (1998)). Furthermore, pro-caspase-2 binds to the CARD protein Raidd (also know as Cradd), which permits recruitment of pro-caspase-2 to Tumor Necrosis Factor (TNF) Receptor complexes and which results in activation of the caspase-2 protease (Ahmad et al., *Cancer Res.* 57:615-619 (1997)). CARD domains can also participate in homotypic interactions with themselves, resulting in self-association of polypeptides that contain these protein-interaction domains and producing dimeric or possibly even oligomeric complexes.

CARD domains can be found in association with other types of functional domains within a single polypeptide, thus providing a mechanism for bringing a functional domain into close proximity or contact with a target protein via CARD:CARD associations involving two CARD-containing polypeptides. For example, the *Caenorhabiditis elegans* cell death gene ced-4 encodes a protein that contains a CARD domain and a ATP-binding oligomerization domain called an NB-ARC domain (van der Biezen and Jones, *Curr. Biol.* 8:R226-R227). The CARD domain of the CED-4 protein interacts with the CARD domain of a pro-caspase called CED-3. The NB-ARC domain allows CED-4 to self-associate, thereby forming an oligomeric complex which brings associated pro-CED-3 molecules into close proximity to each other. Because most pro-caspases possess at least a small amount of protease activity even in their unprocessed form, the assembly of a complex that brings the proforms of caspase into juxtaposition can result in trans-processing of zymogens, producing the proteolytically processed and active caspase. Thus, CED-4 employs a CARD domain for binding a pro-caspase and an NB-ARC domain for self-oligomerization, resulting in caspase clustering, proteolytic processing and activation.

In addition to their role in caspase activation, CARD domains have been implicated in other cellular processes. Some CARD-containing polypeptides, for example, induce activation of the transcription factor NF-κB. NF-κB activation is induced by many cytokines and plays an important role in cytokine receptor signal transduction mechanisms (DiDonato et al., *Nature* 388:548-554 (1997)). Moreover, CARD domains are found in some proteins that inhibit rather than activate caspases, such as the IAP (Inhibitor of Apoptosis Protein) family members, cIAP1 and cIAP2 (Rothe et al., *Cell* 83:1243-1252 (1995)) and oncogenic mutants of the Bcl-10 protein (Willis et al., *Cell* 96:35-45 (1999)). Also, though caspase activation resulting from CARD domain interactions is often involved in inducing apoptosis, other caspases are primarily involved in proteolytic processing and activation of inflammatory cytokines (such as pro-IL-1β and pro-IL-18). Thus, CARD-containing polypeptides can also be involved in cytokine receptor signaling and cytokine production, and, therefore, can be involved in regulation of immune and inflammatory responses.

In view of the function of the CARD domain within the invention CARD-containing polypeptides or functional fragments thereof, polypeptides of the invention are contemplated herein for use in methods to alter biochemical processes such as apoptosis, NF-κB induction, cytokine processing, cytokine receptor signaling, and caspase-mediated proteolysis, thus having modulating effects on cell life and death (i.e., apoptosis), inflammation, cell adhesion, and other cellular and biochemical processes.

It is also contemplated herein that invention CARD-containing polypeptides can associate with other CARD-containing polypeptides to form invention hetero-oligomers or homo-oligomers, such as heterodimers or homodimers. In particular, the association of the CARD domain of invention polypeptides with another CARD-containing polypeptide, such as Apaf-1, CED-4, caspases-1, 2, 9, 11, cIAPs-1 and 2, CARDIAK, Raidd, Dark, CARD4, an invention CARD-containing polypeptide, and the like, including homo-oligomerization, is sufficiently specific such that the bound complex can form in vivo in a cell or in vitro under suitable conditions. Similarly therefore, an invention CARD-containing polypeptide can associate with another CARD-containing polypeptide by CARD:CARD form invention hetero-oligomers or homo-oligomers, such as heterodimers or homodimers.

In accordance with the present invention, sequences for CARD-containing polypeptides have been determined. Thus, the present invention provides CARD-containing polypeptides, including the newly identified CARD-containing polypeptides designated CARD-10X (SEQ ID NO:2), CARD-11X (SEQ ID NO:8) and CARD-12X (SEQ ID NO:16), and functional fragments thereof.

CARD-10X was identified as an unannotated protein product in the NR protein sequence database (GI 10436238; SEQ ID NO:20, encoded by GI 10436237; SEQ ID NO:19). A human EST (GI 9094656; SEQ ID NO:21) and two ESTs for Gallus homologs (GI 7132200; SEQ ID NO:22 and GI 5884878; SEQ ID NO:23) from CARD-10X have also been identified.

CARD-11X was identified from the nucleotide database of High Throughput Genomic Sequences (NTGS) (GI 10198542, 9887755) and also from the NR nucleotide database, GI 9665194). Several human ESTs from CARD-11X have been identified: GI 6926669 (SEQ ID NO:24), GI 6143407 (SEQ ID NO:25), GI 2785620 (SEQ ID NO:26), GI 1838222 (SEQ ID NO:27), GI 6927709 (SEQ ID NO:28), GI 9720543 (SEQ ID NO:29), GI 9142863 (SEQ ID NO:30), GI 1761194 (SEQ ID NO:31), GI 8151878 (SEQ ID NO:32), GI 2007639 (SEQ ID NO:33), GI 8042493 (SEQ ID NO:34), GI 2079290 (SEQ ID NO:35), and GI 7044777 (SEQ ID NO:36).

CARD-12X was identified from the database of HTGS (GI 8224622). A human EST from CARD-12X has also been identified: GI 10316320 (SEQ ID NO:37).

The invention CARD-10X, -11X and -12X nucleic acid molecules do not consist of the exact sequence of the nucleotide sequences set forth in publicly available databases, such as Expressed Sequence Tags (ESTs), Sequence Tagged Sites (STSs) and genomic fragments, deposited in public databases such as the nr, dbest, dbsts, gss and htgs databases, including nucleotide sequences of the GI accession numbers set forth above. Likewise, the invention CARD-10X, -11X and -12X polypeptides do not consist of the exact sequence of the amino acid sequences set forth in publicly available databases, or of the exact amino acid sequence of a translated product of an EST set forth in the databases. Since one of skill in the art will realize that the above-recited excluded sequences may be revised at a later date, the skilled artisan will recognize that the above-recited sequences are excluded as they stand on the priority date of this application.

The CARD domains of these CARD-10X, -11X and -12X are similar to each other, sharing approximately 40-50% sequence identity, as well as similarity by fold prediction criteria. The closest homologs of the CARD domains of the disclosed CARD-containing polypeptides are found in human B-cell CLL/lymphoma 10 protein, and in the equine herpesvirus 2 hypothetical protein E10, which have about 25% sequence identity to the disclosed CARD-domains.

Apart from their CARD domains, both CARD-10X and CARD-11X contain conserved domains found in proteins that bind the cell cytoskeleton. Specifically, CARD-10X contains a domain of approximately 150 amino acids found in many intermediate filament proteins (Pfam code 00038), designated the "filament" domain (SEQ ID NO:6). Intermediate filament proteins are distinct but structurally related proteins that make up intermediate filaments, which are major components of the cytoskeleton. Many intermediate filament proteins are developmentally regulated and tissue specific, and undergo a variety of post-translational modifications, including phosphorylation.

CARD-11X contains a domain of approximately 300 amino acids similar to a domain found in members of the "Ezrin/radixin/moiesin" or "ERM" family (Pfam code 00769). The ERM domain of CARD-11X is most similar to the helical linker region of ERM, but there is also some similarity to the actin-binding region of the ERM domain. ERM domain proteins are involved in connections between cytoskeletal structures and the plasma membrane. ERM proteins mediate these connections by associating both with F-actin and with juxtamembrane proteins, including extracellular matrix and cell adhesion receptors, in a regulated fashion.

CARD-11X also contains a domain designated the "post synaptic density disc-large zo-1" or "PDZ" domain (Pfam code 00595). PDZ domains are protein interaction modules that mediate the binding of a class of submembraneous proteins to ion channels and membrane receptors, including neurotransmitter receptors.

The structural and functional properties of intermediate filament domains, ERM domains and PDZ domains, and proteins containing such domains, can be found in the Pfam database. Pfam is a publicly available large collection of multiple sequence alignments and hidden Markov models that covers many common protein domains. Version 5.5 of Pfam (September 2000) contains alignments and models for 2478 protein families, based on the Swissprot 38 and SP-TrEMBL 11 protein sequence databases.

CARD-10X and CARD-11X are the first CARD-containing polypeptides described to contain cytoskeleton binding domains. These proteins are likely to provide a link between the cell cytoskeleton and the apoptosis regulatory machinery. In particular, CARD-10X and CARD-11X are proposed to play a role in the regulation and/or execution of anoikis, an apoptotic process that occurs when cells are deprived of attachments via integrins, causing disorganization of the cytoskeleton. Specifically, a CARD domain attached to the cytoskeleton may be involved in bringing a caspase to filaments in order to facilitate cytoskeleton cleavage.

This prediction is consistent with results indicating that at early stages of apoptosis, caspases group near the cytoskeleton, and microvillar breakdown occurs. Additionally, a caspase-3-like protease has been show to play a role in the cleavage of the ERM protein moiesin during platelet activation.

Accordingly, besides the biochemical processes such as apoptosis, NF-κB induction, cytokine processing, cytokine receptor signaling, and caspase-mediated proteolysis, in which other known CARD-containing polypeptides are implicated, the CARD-containing polypeptides of the invention are also predicted to be involved in cytoskeletal integrity and anoikis.

As is readily appreciated by one of skill in the art, different isoforms of a gene can be expressed as differently spliced gene products. Thus, it is contemplated herein that the CARD-containing polypeptides of the invention can exist in a variety of isoforms. As referred to herein, an "isoform" of a CARD-containing polypeptide is a biologically active CARD-containing polypeptide that contains at least two contiguous exon sequences from among the various exon sequences known to code for the reference polypeptide.

For example, CARD-11X (SEQ ID NO:8) is encoded by 26 exons, as evidenced by comparison of SEQ ID NO:7 with the genomic sequence set forth in the NR nucleotide database as GI accession number 9665194. CARD-12X (SEQ ID NO:16) is encoded by at least 2 exons, as evidenced by comparison of SEQ ID NO:15 with the genomic sequence set forth in the HTGS nucleotide database as GI accession number 8224622. It is also contemplated herein that an isoform of a CARD-containing polypeptide can include additional amino acids not encoded by the described exon sequences.

In one embodiment, the invention provides a substantially purified CARD-containing polypeptide, comprising substantially the same amino acid sequence as the amino acid sequence of CARD-11X (SEQ ID NO:8) or CARD-12X (SEQ ID NO:16).

In another embodiment, the invention provides a substantially purified functional fragment of a CARD-containing polypeptide, comprising substantially the same amino acid sequence as the amino acid sequence of the CARD domain of CARD-10X (SEQ ID NO:4), the filament domain of CARD-10X (SEQ ID NO:6), the CARD domain of CARD-11X (SEQ ID NO:10) the ERM (ezrin) domain of CARD-11X (SEQ ID NO:12), the PDZ domain of CARD-11X (SEQ ID NO:14) and the CARD domain of CARD-12X (SEQ ID NO:16).

As employed herein, the term "substantially the same amino acid sequence" refers to amino acid sequences having at least about 70% or 75% identity with respect to the reference amino acid sequence, and retaining comparable functional and biological activity characteristic of the polypeptide defined by the reference amino acid sequence. Preferably, polypeptides having "substantially the same amino acid sequence" will have at least about 80%, 82%, 84%, 86% or 88%, more preferably 90%, 91%, 92%, 93% or 94% amino acid identity with respect to the reference amino acid sequence; with greater than about 95%, 96%, 97%, 98% or 99% amino acid sequence identity being especially preferred.

In accordance with the invention, specifically included within the definition of "substantially the same" amino acid sequence is the predominant amino acid sequence of a particular invention CARD-containing polypeptide disclosed herein. The predominant amino acid sequence refers to the most commonly expressed naturally occurring amino acid sequence in a species population. A predominant polypeptide with multiple isoforms will have the most commonly expressed amino acid sequence for each isoform. A predominant CARD-containing polypeptide of the invention refers to an amino acid sequence having sequence identity to an amino acid sequence disclosed herein that is greater than that of any other naturally occurring protein of a particular species (e.g., human).

Given the teachings herein of the nucleic acid or amino acid sequences corresponding to the invention CARD-containing polypeptides, one of skill in the art can readily confirm and, if necessary, revise the nucleic acid or amino acid sequences associated with the CARD-containing polypeptides of the invention. For example, the sequences can be confirmed by probing a cDNA library with a nucleic acid probe corresponding to a nucleic acid of the invention using PCR or other known methods. Further, an appropriate bacterial artificial chromosome containing the region of the genome encoding an invention CARD-containing polypeptide can be commercially obtained and probed using PCR, restriction mapping, sequencing, and other known methods.

A CARD-containing polypeptide or functional fragment thereof can have conservative amino acid substitutions as compared with the reference polypeptide amino acid sequence. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His).

A CARD-containing polypeptide or functional fragment can also be chemically derivatized, provided that the polypeptide retains a CARD-containing polypeptide biological activity. For example, chemical derivatization of an invention polypeptide can be alkylation, acylation, carbamoylation and iodination. Derivatized polypeptides also include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

A CARD-containing polypeptide or functional fragment can also be substituted with one or more amino acid analogs of the twenty standard amino acids, for example, 4-hydroxyproline, 5-hydroxylysine, 3-methylhistidine, homoserine, ornithine or carboxyglutamate, and can include amino acids that are not linked by peptide bonds.

A CARD-containing polypeptide or functional fragment can also contain mimetic portions that orient functional groups that provide a function of a CARD-containing polypeptide. Mimetics encompass chemicals containing chemical moieties that mimic the function of the polypeptide. For example, if a polypeptide contains two charged chemical moieties having functional activity, a mimetic places two charged chemical moieties in a spatial orientation and constrained structure so that the charged chemical function is maintained in three-dimensional space. Exemplary mimetics are peptidomimetics, peptoids, or other peptide-like polymers such as poly(β-amino acids), and also non-polymeric compounds upon which functional groups that mimic a peptide are positioned.

Another embodiment of the invention provides a CARD-containing polypeptide, or a functional fragment thereof, fused with a moiety to form a conjugate. As used herein, a "moiety" can be a physical, chemical or biological entity which contributes functionality to a CARD-containing polypeptide or a functional fragment thereof. Functionalities contributed by a moiety include therapeutic or other biological activity, or the ability to facilitate identification or recovery of a CARD-containing polypeptide. Therefore, a moiety will include molecules known in the art to be useful for detection of the conjugate by, for example, by fluorescence, magnetic imaging, detection of radioactive emission. A moiety may also be useful for recovery of the conjugate, for example a His tag or other known tags used for protein isolation and/or purification, or a physical substance such as a bead. A moiety can be a therapeutic compound, for example, a cytotoxic drug which can be useful to effect a biological change in cells to which the conjugate localizes.

The term "functional", when used herein as a modifier of invention CARD-containing polypeptides, or fragments thereof, refers to a polypeptide that exhibits biological activities similar to at least a portion of a CARD-containing polypeptide of the invention. Biological activities of a CARD-containing polypeptide of the invention include, for example, the ability to bind to a CARD-associated polypeptide (e.g. a caspase or pro-caspase), to another CARD-containing polypeptide, to a cytoskeletal component, or to another protein, thereby altering apoptosis, NF-κB induction, cytokine processing, cytokine receptor signaling, caspase-mediated proteolysis, cytoskeletal integrity or anoikis.

The ability of a CARD-containing polypeptide to bind another polypeptide such as a CARD-associated polypeptide can be assayed, for example, using methods well known in the art, such as yeast two-hybrid assays, co-immunoprecipitation, fluorescence resonance energy transfer (FRET) assays, GST fusion co-purification, and the like.

In accordance with the invention, there are also provided functional fragments of CARD-containing polypeptides which retain some, but not all, of the predominant naturally occurring CARD-containing polypeptide activities. A "functional fragment" is any truncated form, either carboxy-terminal, amino-terminal, or both, of the predominant naturally occurring protein.

For example, a functional fragment of an invention polypeptide can contain one or more of the following: a CARD domain, a filament domain, a ERM domain, and a PDZ domain. In a specific example, a functional fragment of a CARD-containing polypeptide such as CARD-10X can contain a CARD domain, but lack a functional filament domain, or vice versa. Such a fragment will retain certain CARD-10X biological activities (e.g., CARD domain functionality), but not all such activities (e.g., lack filament domain functionality).

In another example, a functional fragment of a CARD-11X polypeptide can contain one, or any two, of the CARD domain, ERM domain and PDZ domains, but lack at least one functional domain. Such a fragment will retain certain CARD-11X biological activities (e.g., CARD domain functionality, or association with cytoskeletal components, or both), but not all such activities.

In one embodiment, the activity of the functional fragment will be "dominant-negative." A dominant-negative activity will allow the fragment to reduce or inactivate the activity of one or more isoforms of a predominant naturally occurring CARD-containing polypeptide.

Another biological activity of a CARD-containing polypeptide or functional fragment thereof is the ability to act as an immunogen for the production of polyclonal and monoclonal antibodies that bind specifically to an invention CARD-containing polypeptide. Such immunologic activity may be assayed by any method known to those of skill in the art. For example, a test-polypeptide encoded by a CARD-encoding cDNA can be used to produce antibodies, which are then assayed for their ability to bind to an invention CARD-containing polypeptide. If the antibody binds to the test-polypeptide and the reference polypeptide with substantially the same affinity, then the polypeptide possesses the requisite immunologic biological activity.

Thus, the invention also provides a substantially purified functional fragment of a CARD-containing polypeptide, comprising at least 10 contiguous residues of CARD-10X (SEQ ID NO:2), CARD-11X (SEQ ID NO:8) or CARD-12X (SEQ ID NO:16), wherein the functional fragment is immunogenic.

The length of the functional fragments of the invention can range from about 10 amino acids up to the full-length sequence of an invention CARD-containing polypeptide. In certain embodiments, such as for invention immunogenic fragments, the amino acid lengths include, for example, at least about 12 amino acids, such as at least about, or not more than, 15, 20, 25, 30, 35, 40, 45, 50, 55, 60 or 65 amino acids. In other embodiments, such as for longer invention immunogenic fragments and fragments containing CARD, filament, ERM or PDZ domains, the functional fragments can contain at least about, or not more than, 70, 75, 80, 90, 100, 125, 150, 175, 200, 250, 300, 400, 500 or more amino acids in length up to the full-length CARD-containing polypeptide sequence.

As used herein, the term "substantially purified" means a polypeptide that is in a form that is relatively free from contaminating lipids, polypeptides, nucleic acids or other cellular material normally associated with a polypeptide in a cell. A substantially purified CARD-containing polypeptide can be obtained by a variety of methods well-known in the art, e.g., recombinant expression systems described herein, precipitation, gel filtration, ion-exchange, reverse-phase and affinity chromatography, and the like. Other well-known methods are described in Deutscher et al., "Guide to Protein Purification" *Methods in Enzymology* Vol. 182, (Academic Press, (1990)). The methods and conditions for biochemical purification of a polypeptide of the invention can be chosen by those skilled in the art, and purification monitored, for example, by an immunological assay, binding assay, or a functional assay.

An example of a method for preparing the invention polypeptide(s) is to express nucleic acids encoding a CARD-containing polypeptide in a suitable host cell, such as a bacterial cell, a yeast cell, an amphibian cell such as an oocyte, or a mammalian cell, using methods well known in the art, and recovering the expressed polypeptide, again using well-known purification methods. Invention polypeptides can be isolated directly from cells that have been transformed with expression vectors as known in the art. Recombinantly expressed polypeptides of the invention can also be expressed as fusion proteins with appropriate affinity tags, such as glutathione S transferase (GST) or poly His, and affinity purified. The invention polypeptide, biologically functional fragments, and functional equivalents thereof can also be produced by in vitro transcription/translation methods known in the art, such as using reticulocyte lysates, as used for example, in the TNT system (Promega). The invention polypeptide, biologically functional fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

Methods to identify additional invention polypeptides containing a functional fragment of a CARD-containing polypeptide are well known in the art. For example, genomic or cDNA libraries from any species or tissue are commercially available or can be readily prepared, and can be probed according to methods known in the art. Full-length polypeptide-encoding nucleic acids, such as full-length cDNAs can be obtained by a variety of methods well-known in the art, such as 5' and 3' RACE.

In another embodiment of the invention, chimeric polypeptides are provided comprising a CARD-containing polypeptide, or a functional fragment thereof, fused with another polypeptide or functional fragment thereof. Polypeptides with which the CARD-containing polypeptide or functional fragment thereof are fused can include, for example, glutathione-S-transferase, an antibody, or other proteins or functional fragments thereof which facilitate recovery of the chimera. Further polypeptides with which a CARD-containing polypeptide or functional fragment thereof are fused will include, for example, luciferase, a green fluorescent protein, an antibody, or other proteins or functional fragments thereof which facilitate identification of the chimera. Still further polypeptides with which a CARD-containing polypeptide or functional fragment thereof can advantageously be fused include, for example, the LexA DNA binding domain, ricin, α-sarcin, an antibody or fragment thereof, or other polypeptides which have therapeutic properties or other biological activity.

Further invention chimeric polypeptides contemplated herein are chimeric polypeptides wherein a functional fragment of a CARD-containing polypeptide is fused with a catalytic domain or a protein interaction domain from a heterologous polypeptide. One of skill in the art will appreciate that a large number of chimeric polypeptides are readily available by combining domains of 2 or more CARD-containing polypeptides of the invention. Further, chimeric polypeptides can contain a functional fragment of a CARD-containing polypeptide of the invention fused with a domain of a protein known in the art, such as CED-4, Apaf-1, caspase-1, and the like.

The invention also provides methods for administering CARD-containing polypeptides to an individual to modulate an activity associated with a CARD-containing polypeptide, including induction of apoptosis or anoikis, tumor suppression, modulation of inflammation or cell adhesion and the like. A CARD-containing polypeptide can be administered therapeutically to an individual using expression vectors containing nucleic acids encoding CARD-containing polypeptides, as described below. In addition, CARD-containing polypeptides, or a functional portion thereof, can be directly administered to an individual. Methods of administering therapeutic polypeptides in the form of a pharmaceutical composition are well known to those skilled in the art.

An exemplary method of delivering a CARD-containing polypeptide to an intracellular target is to fuse a CARD-containing polypeptide or functional fragment to an intracellular-targeting peptide that can penetrate the cell membrane or otherwise deliver a polypeptide to the intracellular environment such as via internalization, thereby causing the fused CARD-containing polypeptide to enter the cell. One example of such an intracellular-targeting peptides is a fusion to the transduction domain of HIV TAT, which allows transduction of up to 100% of cells (Schwarze et al., *Science* 285:1569-1572 (1999); Vocero-Akbani et al., *Nature Med.* 5:29-33 (1999)).

Another example of such an intracellular-targeting peptide is the Antennapeida homeoprotein internalization domain (Holinger et al., *J. Biol. Chem.* 274:13298-13304 (1999)). Still another intracellular-targeting peptide is a peptide that is specific for a cell surface receptor, which allows binding and internalization of a fusion polypeptide via receptor-mediated endocytosis (Ellerby et al., *Nature Med.* 5:1032-1038 (1999)). Such intracellular-targeting peptides that mediate specific receptor interactions can be advantageously used to target a tumor (see Ellerby et al., supra, 1999). Alternatively, a CARD-containing polypeptide of the invention can be incorporated, if desired, into liposomes, microspheres or other polymer matrices (Gregoriadis, *Liposome Technology*, Vols. I to III, 2nd ed., CRC Press, Boca Raton Fla. (1993)).

In accordance with another embodiment of the invention, there are provided isolated nucleic acid molecules encoding a CARD-containing polypeptide or functional fragment thereof. The invention isolated nucleic acids encoding CARD-containing polypeptides are selected from:

(a) a nucleic acid molecule encoding a polypeptide comprising the amino acid sequence of CARD-11X (SEQ ID NO:8) or CARD-12X (SEQ ID NO:16);

(b) a nucleic acid molecule comprising the nucleotide sequence of SEQ ID NO:7 or SEQ ID NO:15; and (c) a nucleic acid molecule that hybridizes to the nucleic acid molecule of (a) or (b) under moderately stringent hybridization conditions.

The invention also provides isolated nucleic acid molecules encoding functional fragments of a CARD-containing polypeptide selected from:

(a) a nucleic acid molecule encoding the CARD domain of CARD-10X (SEQ ID NO:4), the filament domain of CARD-10X (SEQ ID NO:6), the CARD domain of CARD-11X (SEQ ID NO:10), the ERM (ezrin) domain of CARD-11X (SEQ ID NO:12), the PDZ domain of CARD-11X (SEQ. ID NO:14) and the CARD domain of CARD-12X (SEQ ID NO:16);

(b) a nucleic acid molecule comprising the nucleotide sequence of the CARD domain of CARD-10X (SEQ ID NO:3), the filament domain of CARD-10X (SEQ ID NO:5), the CARD domain of CARD-11X (SEQ ID NO:9), the ERM (ezrin) domain of CARD-11X (SEQ ID NO:11), the PDZ domain of CARD-11X (SEQ ID NO:13) and the CARD domain of CARD-12X (SEQ ID NO:15); and (c) a nucleic acid molecule that hybridizes to the nucleic acid molecule of (a) or (b) under moderately stringent hybridization conditions.

Also provided are isolated nucleic acid molecules having substantially the same nucleotide sequence as the CARD-11X (SEQ ID NO:7) or CARD-12X (SEQ ID NO:15) coding sequence.

The nucleic acid molecules described herein are useful for producing invention polypeptides, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an invention CARD-encoding gene or mRNA transcript in a given sample. The nucleic acid molecules described herein, and fragments thereof, are also useful as primers and/or templates in a PCR reaction for amplifying genes encoding invention polypeptides described herein.

The term "nucleic acid molecule" or "polynucleotide" encompasses ribonucleic acid (RNA) or deoxyribonucleic acid (DNA), probes, oligonucleotides, and primers, and can be single stranded or double stranded. DNA can be either complementary DNA (cDNA) or genomic DNA, e.g. a CARD-encoding gene, and can represent the sense strand, the anti-sense strand, or both. Examples of nucleic acids are RNA, cDNA, and isolated genomic DNA encoding a CARD-containing polypeptide.

One means of isolating a CARD-encoding nucleic acid polypeptide is to probe a mammalian genomic or cDNA library with a natural or artificially designed DNA probe using methods well known in the art. DNA probes derived from the CARD-encoding gene are particularly useful for this purpose. DNA and cDNA molecules that encode CARD-containing polypeptides can be used to obtain complementary genomic DNA, cDNA or RNA from mammalian (e.g., human, mouse, rat, rabbit, pig, and the like), or other animal sources, or to isolate related cDNA or genomic clones by screening cDNA or genomic libraries, using methods described in more detail below.

In general, a genomic sequence of the invention includes regulatory regions such as promoters, enhancers, and introns that are outside of the exons encoding a CARD-containing polypeptide, but does not include proximal genes that do not encode a CARD-containing polypeptide.

Use of the term "isolated" as a modifier of nucleic acids or polypeptides means that the molecules so designated have been produced in such form by the hand of man, and thus are separated from their native in vivo cellular environment.

Invention nucleic acids encoding CARD-containing polypeptides and invention CARD-containing polypeptides can be obtained from any species of organism, such as prokaryotes, eukaryotes, plants, fungi, vertebrates, invertebrates, and the like. A preferred source of invention nucleic acids are mammalian species, e.g., human, rat, mouse, rabbit, monkey, baboon, bovine, porcine, ovine, canine, feline, and the like, with human particularly preferred.

As employed herein, the term "substantially the same nucleotide sequence" refers to a nucleic acid molecule having sufficient identity to the reference polynucleotide, such that it will hybridize to the reference polynucleotide under moderately or highly stringent hybridization conditions. In one embodiment, a nucleic acid molecule having substantially the same nucleotide sequence as the reference nucleotide sequence encodes substantially the same amino acid sequence as that set forth in any of SEQ ID NOS:2, 8 or 16, or its functional fragments. In another embodiment, DNA having "substantially the same nucleotide sequence" as the reference nucleotide sequence has at least 60%, such as 65%, 70%, 72%, 74%, 76%, 78%, 80%, 82%, 84%, 86% or 88%, more preferably at least 90%, 91%, 92%, 93% or 94%, yet more preferably at least 95%, 96%, 97%, 98% or 99% identity to the reference nucleotide sequence.

In accordance with the invention, specifically included within the definition of "substantially the same" nucleotide sequence is the predominant nucleotide sequence of a particular invention CARD-containing polypeptide described herein. The predominant nucleotide sequence refers to the most commonly present naturally occurring nucleotide sequence in a species population. A predominant CARD-encoding nucleic acid of the invention refers to a nucleotide sequence having sequence identity to a nucleotide sequence disclosed herein that is greater than that of any other naturally occurring nucleotide sequence of a particular species (e.g., human).

A nucleotide sequence that is substantially the same as a reference nucleotide sequence can include, for example, one or several nucleotide additions, deletions, or substitutions with respect to the reference sequence. Exemplary substitutions to a reference sequence are substitutions that do not change the encoded amino acid sequence due to the degeneracy of the genetic code, or that result in a nucleotide sequence that encodes an amino acid sequence that is "substantially the same" as a reference polypeptide, as described above. Such additions, deletions and substitutions can correspond to variations that are made deliberately, or which occur as mutations during nucleic acid replication.

A nucleotide sequence that is substantially the same as a reference CARD-encoding nucleotide sequence can be a sequence that corresponds to homologs of other species, including other mammalian species. The corresponding nucleotide sequences of non-human species can be determined by methods known in the art, such as by PCR or by screening genomic, cDNA or expression libraries. A nucleotide sequence that is substantially the same as a reference sequence can also correspond to splice variant forms of the CARD-encoding nucleotide sequence.

A nucleic acid molecule of the invention can include one or more non-native nucleotides, having, for example, modifications to the base, the sugar, or the phosphate portion, or having a modified phosphodiester linkage. Such modifications can be advantageous in increasing the stability of the nucleic acid molecule.

Furthermore, a nucleic acid molecule of the invention can include, for example, a detectable moiety, such as a radiolabel, a fluorochrome, a ferromagnetic substance, a luminescent tag or a detectable binding agent such as biotin. Such moieties can be advantageous in applications where detection of a CARD-encoding nucleic acid molecule is desired.

As used herein, the term "hybridization" refers to the binding of complementary strands of nucleic acid (i.e., sense: antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature (Tm) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-nucleic acid to bind a complementary nucleic acid. The hybridized nucleic acids will generally have at least about 60% identity, such as at least about 75% identity, more preferably at least about 90% identity. Moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C.

The phrase "high stringency hybridization" refers to conditions that permit hybridization of only those nucleic acid sequences that form stable hybrids in 0.018M NaCl at 65° C. Thus, if a hybrid is not stable in 0.018M NaCl at 65° C., it will not be stable under high stringency conditions, as contemplated herein. High stringency conditions can be provided, for example, by hybridization in 50% formamide, 5×Denhart's solution, 5×SSPE, 0.2% SDS at 42° C., followed by washing in 0.1X SSPE, and 0.1% SDS at 65° C.

Other suitable moderate stringency and high stringency hybridization buffers and conditions are well known to those of skill in the art and are described, for example, in Sambrook et al., Molecular Cloning—A Laboratory Manual, Cold Spring Harbor Laboratory, Cold Spring Harbor, N.Y., (1989), and Current Protocols in Molecular Biology, F. M. Ausubel et al., eds., (Current Protocols, a joint venture between Greene Publishing Associates, Inc. and John Wiley & Sons, Inc., (most recent Supplement).

Identity of any two nucleic acid or amino acid sequences can be determined by those skilled in the art based, for example, on a BLAST 2.0 computer alignment, using default parameters. BLAST 2.0 computer searching and sequence alignments are known in the art (e.g. Tatusova et al., *FEMS Microbiol Lett.* 174:247-250 (1999) and Altschul et al., *Nucleic Acids Res.*, 25:3389-3402 (1997)), and are publicly available.

One means of isolating a nucleic acid encoding a CARD-containing polypeptide is to probe a cDNA library or genomic library with a natural or artificially designed nucleic acid probe using methods well known in the art. Nucleic acid probes derived from a CARD-encoding gene are particularly useful for this purpose. DNA and cDNA molecules that encode CARD-containing polypeptides can be used to obtain complementary genomic DNA, cDNA or RNA from mammals, for example, human, mouse, rat, rabbit, pig, and the like, or other animal sources, or to isolate related cDNA or genomic clones by the screening of cDNA or genomic libraries, by methods well known in the art.

The invention further provides oligonucleotides that function as single stranded nucleic acid primers for amplification of a CARD-encoding nucleic acid, or as probes for identification of a CARD-encoding nucleic acid.

The invention oligonucleotides comprise at least 15 contiguous nucleotides of SEQ ID NOS:1, 7 or 15, or its complement. The invention oligonucleotides can include at least, or not more than, 16, 17, 18, 19, 20, 25, 30, 40, 50, 60, 70, 80, 90, 100, 125, 150, 175, 200, 225, 250, 275, 300, 325, 350 or more contiguous nucleotides from the reference nucleotide sequence or its complement.

The oligonucleotides of the invention are able to hybridize to the reference nucleic acid molecules of the invention under moderately stringent, or highly stringent, hybridization conditions and thus can be advantageously used, for example, as probes to detect CARD-encoding DNA or RNA in a sample, and to detect splice variants thereof; as sequencing or PCR primers; as antisense reagents to block transcription of CARD-encoding RNA in cells; or in other applications known to those skilled in the art in which hybridization to a CARD-encoding nucleic acid molecule is desirable.

In accordance with another embodiment of the invention, a method is provided for identifying nucleic acids encoding a CARD-containing polypeptide. The method includes the steps of contacting a sample containing nucleic acids with an invention oligonucleotide, wherein the contacting is effected under high stringency hybridization conditions, and identifying a nucleic acid that hybridizes thereto.

The invention additionally provides a method of detecting a CARD-encoding nucleic acid molecule in a sample by contacting the sample with two or more invention oligonucleotides, amplifying a nucleic acid molecule, and detecting the amplification. The amplification can be performed, for example, using PCR.

The isolated nucleic acid molecules an oligonucleotides of the invention can be used in a variety of diagnostic and therapeutic applications. For example, the isolated nucleic acid molecules of the invention can be used as probes, as described above; as templates for the recombinant expression of CARD-containing polypeptides; or in screening assays such as two-hybrid assays to identify cellular molecules that bind CARD-containing polypeptides.

The isolated nucleic acid molecules of the invention can be prepared by methods known in the art. The method chosen will depend on factors such as the type and size of nucleic acid molecule one intends to isolate; whether or not it encodes a biologically active polypeptide (e.g. having a CARD-containing polypeptide biological or immunogenic activity); and the source of the nucleic acid molecule.

An exemplary method for preparing an isolated nucleic acid molecule involves amplification of the nucleic acid molecule using invention oligonucleotide primers and the polymerase chain reaction (PCR) and, optionally, purification of the resulting product by gel electrophoresis. Using PCR, a CARD-encoding nucleic acid molecule having any desired boundaries can be amplified exponentially starting from only a few DNA or RNA molecules, such as from a single cell. Desired modifications to the nucleic acid sequence can also be introduced by choosing an appropriate oligonucleotide primer with one or more additions, deletions or substitutions. PCR methods, including methods of isolating homologs of a given nucleic acid molecule in another species using degenerate primers, are well known in the art.

Alternatively, an isolated CARD-encoding nucleic acid molecule can be prepared by screening a library, such as a genomic library, cDNA library or expression library, with a detectable CARD-encoding nucleic acid molecule or anti-CARD antibody. Human libraries, and libraries from a large variety of mammalian species, are commercially available or can be produced from species or cells of interest. The library clones identified as containing CARD-encoding nucleic acid molecules can be isolated, subcloned or sequenced by routine methods.

Furthermore, an isolated CARD-encoding nucleic acid molecule or oligonucleotide can be prepared by direct synthetic methods. For example, a single stranded nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as probes and primers, and also for producing nucleic acid molecules containing modified nucleotides or linkages.

The invention also provides methods for detecting a CARD-encoding nucleic acid in a sample. The methods of detecting a CARD-encoding nucleic acid in a sample can be either qualitative or quantitative, as desired. For example, the presence, abundance, integrity or structure of a CARD-encoding nucleic acid can be determined, as desired, depending on the assay format and the probe used for hybridization or primer pair chosen for application.

Useful assays for detecting a CARD-containing nucleic acid based on specific hybridization with an isolated invention oligonucleotide are well known in the art and include, for example, in situ hybridization, which can be used to detect altered chromosomal location of the nucleic acid molecule, altered gene copy number, and RNA abundance, depending on the assay format used. Other hybridization assays include, for example, Northern blots and RNase protection assays, which can be used to determine the abundance and integrity of different RNA splice variants, and Southern blots, which can be used to determine the copy number and integrity of DNA. A hybridization probe can be labeled with any suitable detectable moiety, such as a radioisotope, fluorochrome, chemiluminescent marker, biotin, or other detectable moiety known in the art that is detectable by analytical methods.

Useful assays for detecting a CARD-encoding nucleic acid in a sample based on amplifying a CARD-encoding nucleic acid with two or more invention oligonucleotides are also well known in the art, and include, for example, qualitative or quantitative polymerase chain reaction (PCR); reverse-transcription PCR (RT-PCR); single strand conformational polymorphism (SSCP) analysis, which can readily identify a single point mutation in DNA based on differences in the secondary structure of single-strand DNA that produce an altered electrophoretic mobility upon non-denaturing gel electrophoresis; and coupled PCR, transcription and translation assays, such as a protein truncation test, in which a mutation in DNA is determined by an altered protein product on an electrophoresis gel. Additionally, the amplified CARD-encoding nucleic acid can be sequenced to detect mutations and mutational hot-spots, and specific assays for large-scale screening of samples to identify such mutations can be developed.

Also provided are antisense-nucleic acids having a sequence capable of binding specifically with full-length or any portion of an mRNA that encodes CARD-containing polypeptides so as to prevent translation of the mRNA. The antisense-nucleic acid can have a sequence capable of binding specifically with any portion of the sequence of the cDNA encoding CARD-containing polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense-nucleic acid is an antisense-nucleic acid comprising chemical analogs of nucleotides.

The present invention provides means to alter levels of expression of CARD-containing polypeptides by recombinantly expressing CARD-containing anti-sense nucleic acids or employing synthetic anti-sense nucleic acid compositions (hereinafter SANC) that inhibit translation of mRNA encoding these polypeptides. Synthetic oligonucleotides, or other antisense-nucleic acid chemical structures designed to recognize and selectively bind to mRNA are constructed to be complementary to full-length or portions of a CARD-encoding strand, including nucleotide sequences substantially the same as SEQ ID NOS:1, 7 or 15.

The SANC is designed to be stable in the blood stream for administration to a subject by injection, or in laboratory cell culture conditions. The SANC is designed to be capable of passing through the cell membrane in order to enter the cytoplasm of the cell by virtue of physical and chemical properties of the SANC, which render it capable of passing through cell membranes, for example, by designing small, hydrophobic SANC chemical structures, or by virtue of specific transport systems in the cell which recognize and transport the SANC into the cell. In addition, the SANC can be designed for administration only to certain selected cell populations by targeting the SANC to be recognized by specific cellular uptake mechanisms which bind and take up the SANC only within select cell populations. In a particular embodiment the SANC is an antisense oligonucleotide.

For example, the SANC may be designed to bind to a receptor found only in a certain cell type, as discussed above. The SANC is also designed to recognize and selectively bind to target mRNA sequence, which can correspond to a sequence contained within the sequences set forth as SEQ ID NOS:1, 7 or 15.

The SANC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SANCs have been shown to be capable of such properties when directed against mRNA targets (see Cohen et al., *TIPS*, 10:435 (1989) and Weintraub, *Sci. American*, January (1990), pp. 40).

The invention further provides a method of altering the level of a biochemical process modulated by a CARD-containing polypeptide by introducing an antisense nucleotide sequence into the cell, wherein the antisense nucleotide sequence specifically hybridizes to a CARD-encoding nucleic acid molecule, wherein the hybridization reduces or inhibits the expression of the CARD-containing polypeptide in the cell. The use of anti-sense nucleic acids, including recombinant anti-sense nucleic acids or SANCs, can be advantageously used to inhibit cell death.

Compositions comprising an amount of the antisense-nucleic acid of the invention, effective to reduce expression of CARD-containing polypeptides by entering a cell and binding specifically to CARD-encoding mRNA so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. For example, the structure can be part of a protein known to bind to a cell-type specific receptor such as a tumor.

Antisense-nucleic acid compositions are useful to inhibit translation of mRNA encoding invention polypeptides. Synthetic oligonucleotides, or other antisense chemical structures are designed to bind to CARD-encoding mRNA and inhibit translation of mRNA and are useful as compositions to inhibit expression of CARD-encoding genes or CARD-associated polypeptide genes in a tissue sample or in a subject.

The above-described nucleotide sequences can be incorporated into vectors for further manipulation. As used herein, vector refers to a recombinant DNA or RNA plasmid or virus containing discrete elements that are used to introduce heterologous DNA into cells for either expression or replication thereof.

The invention also provides vectors containing the CARD-encoding nucleic acids of the invention. Suitable expression vectors are well-known in the art and include vectors capable of expressing nucleic acid operatively linked to a regulatory sequence or element such as a promoter region or enhancer region that is capable of regulating expression of such nucleic acid. Appropriate expression vectors include those that are replicable in eukaryotic cells and/or prokaryotic cells and those that remain episomal or those which integrate into the host cell genome.

Promoters or enhancers, depending upon the nature of the regulation, can be constitutive or regulated. The regulatory sequences or regulatory elements are operatively linked to a nucleic acid of the invention such that the physical and functional relationship between the nucleic acid and the regulatory sequence allows transcription of the nucleic acid.

Suitable vectors for expression in prokaryotic or eukaryotic cells are well known to those skilled in the art (see, for example, Ausubel et al., supra, 2000). Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. The vectors of the invention are useful for subcloning and amplifying a CARD-encoding nucleic acid molecule and for recombinantly expressing a CARD-containing polypeptide. A vector of the invention can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art. One skilled in the art will know or can readily determine an appropriate promoter for expression in a particular host cell.

The invention additionally provides recombinant cells containing CARD-encoding nucleic acids of the invention. The recombinant cells are generated by introducing into a host cell a vector containing a CARD-encoding nucleic acid molecule. The recombinant cells are transduced, transfected or otherwise genetically modified. Exemplary host cells that can be used to express recombinant CARD molecules include mammalian primary cells; established mammalian cell lines, such as COS, CHO, HeLa, NIH3T3, HEK 293 and PC12 cells; amphibian cells, such as *Xenopus* embryos and oocytes and other vertebrate cells. Exemplary host cells also include insect cells such as *Drosophila*, yeast cells such as *Saccharomyces cerevisiae, Saccharomyces pombe*, or *Pichia pastoris*, and prokaryotic cells such as *Escherichia coli*. Additional host cells can be obtained, for example, from ATCC (Manassas, Va.).

The invention also provides a method for expression of a CARD-containing polypeptide by culturing cells containing a CARD-encoding nucleic acid under conditions suitable for expression of a CARD-containing polypeptide. Suitable culturing conditions for expression of an encoded nucleic acid molecule are well known in the art, and described, for example, in Ausubel et al., supra, 2000.

CARD-encoding nucleic acids can also be delivered into mammalian cells, either in vivo or in vitro, to modulate an activity associated with a CARD-containing polypeptide, including induction of apoptosis or anoikis, tumor suppression, modulation of inflammation or cell adhesion and the like. Suitable vectors for delivering a CARD-encoding nucleic acid molecule of the invention to a mammalian cell include viral vectors such as retroviral vectors, adenovirus, adeno-associated virus, lentivirus, herpesvirus, as well as non-viral vectors such as plasmid vectors. Such vectors are useful for providing therapeutic amounts of a CARD-containing polypeptide (see, for example, U.S. Pat. No. 5,399,346, issued Mar. 21, 1995). Delivery of CARD nucleic acids therapeutically can be particularly useful when targeted to a tumor cell, thereby inducing apoptosis in tumor cells. In addition, where it is desirable to limit or reduce the in vivo expression of a CARD-containing polypeptide, the introduction of a vector expressing the antisense strand of the invention nucleic acid molecule is contemplated.

Viral based systems provide the advantage of being able to introduce relatively high levels of the heterologous nucleic acid into a variety of cells. Suitable viral vectors for introducing an invention CARD-encoding nucleic acid into mammalian cells are well known in the art. These viral vectors include, for example, Herpes simplex virus vectors (Geller et al., *Science*, 241:1667-1669 (1988)); vaccinia virus vectors (Piccini et al., *Meth. Enzymology*, 153:545-563 (1987)); cytomegalovirus vectors (Mocarski et al., in *Viral Vectors*, Y. Gluzman and S. H. Hughes, Eds., Cold Spring Harbor Laboratory, Cold Spring Harbor, N.Y., 1988, pp. 78-84)); Moloney murine leukemia virus vectors (Danos et al., *Proc. Natl. Acad. Sci. USA*, 85:6460-6464 (1988); Blaese et al., *Science*, 270: 475-479 (1995); Onodera et al., *J. Virol.*, 72:1769-1774 (1998)); adenovirus vectors (Berkner, *Biotechniques*, 6:616-626 (1988); Cotten et al., *Proc. Natl. Acad. Sci. USA*, 89:6094-6098 (1992); Graham et al., *Meth. Mol. Biol.*, 7:109-127 (1991); Li et al., *Human Gene Therapy*, 4:403-409 (1993); Zabner et al., *Nature Genetics*, 6:75-83 (1994)); adeno-associated virus vectors (Goldman et al., *Human Gene Therapy*, 10:2261-2268 (1997); Greelish et al., *Nature Med.*, 5:439-443 (1999); Wang et. al., *Proc. Natl. Acad. Sci. USA*, 96:3906-3910 (1999); Snyder et al., *Nature Med.*, 5:64-70 (1999); Herzog et al., *Nature Med.*, 5:56-63 (1999)); retrovirus vectors (Donahue et al., *Nature Med.*, 4:181-186 (1998); Shackleford et al., *Proc. Natl. Acad. Sci. USA*, 85:9655-9659 (1988); U.S. Pat. Nos. 4,405,712, 4,650,764 and 5,252,479, and WIPO publications WO 92/07573, WO 90/06997, WO 89/05345, WO 92/05266 and WO 92/14829; and lentivirus vectors (Kafri et al., *Nature Genetics*, 17:314-317 (1997)).

For example, in one embodiment of the present invention, adenovirus-transferrin/polylysine-DNA (TfAdpl-DNA) vector complexes (Wagner et al., *Proc. Natl. Acad. Sci. USA*, 89:6099-6103 (1992); Curiel et al., *Hum. Gene Ther.*, 3:147-154 (1992); Gao et al., *Hum. Gene Ther.*, 4:14-24 (1993)) are employed to transduce mammalian cells with heterologous CARD-encoding nucleic acid. Any of the plasmid expression vectors described herein may be employed in a TfAdpl-DNA complex.

Vectors useful for therapeutic administration of a CARD-encoding nucleic acid can contain a regulatory element that provides tissue specific or inducible expression of an operatively linked nucleic acid. One skilled in the art can readily determine an appropriate tissue-specific promoter or enhancer that allows expression of a CARD polypeptide or nucleic acid in a desired tissue. Any of a variety of inducible promoters or enhancers can also be included in the vector for regulatable expression of a CARD polypeptide or nucleic acid. Such inducible systems, include, for example, tetracycline inducible system (Gossen & Bizard, *Proc. Natl. Acad. Sci. USA*, 89:5547-5551 (1992); Gossen et al., *Science*, 268: 1766-1769 (1995); Clontech, Palo Alto, Calif.); metallothionein promoter induced by heavy metals; insect steroid hormone responsive to ecdysone or related steroids such as muristerone (No et al., *Proc. Natl. Acad. Sci. USA*, 93:3346-3351 (1996); Yao et al., *Nature*, 366:476-479 (1993); Invitrogen, Carlsbad, Calif.); mouse mammary tumor virus (MMTV) induced by steroids such as glucocorticoid and estrogen (Lee et al., *Nature*, 294:228-232 (1981); and heat shock promoters inducible by temperature changes.

An inducible system particularly useful for therapeutic administration utilizes an inducible promoter that can be regulated to deliver a level of therapeutic product in response to a given level of drug administered to an individual and to have little or no expression of the therapeutic product in the absence of the drug. One such system utilizes a Gal4 fusion that is inducible by an antiprogestin such as mifepristone in a modified adenovirus vector (Burien et al., *Proc. Natl. Acad. Sci. USA*, 96:355-360 (1999). Another such inducible system utilizes the drug rapamycin to induce reconstitution of a transcriptional activator containing rapamycin binding domains of FKBP12 and FRAP in an adeno-associated virus vector (Ye et al., *Science*, 283:88-91 (1999)). It is understood that any combination of an inducible system can be combined in any suitable vector, including those disclosed herein. Such a regulatable inducible system is advantageous because the level of expression of the therapeutic product can be controlled by the amount of drug administered to the individual or, if desired, expression of the therapeutic product can be terminated by stopping administration of the drug.

The specificity of viral vectors for particular cell types can be utilized to target predetermined cell types. Thus, the selection of a viral vector will depend, in part, on the cell type to be targeted. For example, if a neurodegenerative disease is to be treated by increasing the level of a CARD-containing polypeptide in neuronal cells affected by the disease, then a viral vector that targets neuronal cells can be used. A vector derived from a herpes simplex virus is an example of a viral vector that targets neuronal cells (Battleman et al., *J. Neurosci.* 13:941-951 (1993), which is incorporated herein by reference). Similarly, if a disease or pathological condition of the hematopoietic system is to be treated, then a viral vector that is specific for a particular blood cell or its precursor cell can be used. A vector based on a human immunodeficiency virus is an example of such a viral vector (Carroll et al., *J. Cell. Biochem.* 17E:241 (1993), which is incorporated herein by reference). In addition, a viral vector or other vector can be constructed to express a CARD-encoding nucleic acid in a tissue specific manner by incorporating a tissue-specific promoter or enhancer into the vector (Dai et al., *Proc. Natl. Acad. Sci. USA* 89:10892-10895 (1992), which is incorporated herein by reference).

For gene therapy, a vector containing a CARD-encoding nucleic acid or an antisense nucleotide sequence can be administered to a subject by various methods. For example, if viral vectors are used, administration can take advantage of the target specificity of the vectors. In such cases, there in no need to administer the vector locally at the diseased site. However, local administration can be a particularly effective method of administering a CARD-encoding nucleic acid. In addition, administration can be via intravenous or subcutaneous injection into the subject. Following injection, the viral vectors will circulate until they recognize host cells with the appropriate target specificity for infection. Injection of viral vectors into the spinal fluid also can be an effective mode of administration, for example, in treating a neurodegenerative disease.

Receptor-mediated DNA delivery approaches also can be used to deliver a CARD-encoding nucleic acid molecule into cells in a tissue-specific manner using a tissue-specific ligand or an antibody that is non-covalently complexed with the nucleic acid molecule via a bridging molecule (Curiel et al., *Hum. Gene Ther.* 3:147-154 (1992); Wu and Wu, *J. Biol. Chem.* 262:4429-4432 (1987), each of which is incorporated herein by reference). Direct injection of a naked or a nucleic acid molecule encapsulated, for example, in cationic liposomes also can be used for stable gene transfer into non-dividing or dividing cells in vivo (Ulmer et al., *Science* 259: 1745-1748 (1993), which is incorporated herein by reference). In addition, a CARD-encoding nucleic acid molecule can be transferred into a variety of tissues using the particle bombardment method (Williams et al., *Proc. Natl. Acad. Sci. USA* 88:2726-2730 (1991), which is incorporated herein by reference). Such nucleic acid molecules can be linked to the appropriate nucleotide sequences required for transcription and translation.

A particularly useful mode of administration of a CARD-encoding nucleic acid is by direct inoculation locally at the site of the disease or pathological condition. Local administration can be advantageous because there is no dilution effect and, therefore, the likelihood that a majority of the targeted cells will be contacted with the nucleic acid molecule is increased. Thus, local inoculation can alleviate the targeting requirement necessary with other forms of administration and, if desired, a vector that infects all cell types in the inoculated area can be used. If expression is desired in only a specific subset of cells within the inoculated area, then a promoter, an enhancer or other expression element specific for the desired subset of cells can be linked to the nucleic acid molecule. Vectors containing such nucleic acid molecules and regulatory elements can be viral vectors, viral genomes, plasmids, phagemids and the like. Transfection vehicles such as liposomes also can be used to introduce a non-viral vector into recipient cells. Such vehicles are well known in the art.

The invention additionally provides an isolated anti-CARD antibody having specific reactivity with a invention CARD-containing polypeptide. The anti-CARD antibody can be a monoclonal antibody or a polyclonal antibody. The invention further provides cell lines producing monoclonal antibodies having specific reactivity with an invention CARD-containing protein.

The invention thus provides antibodies that specifically bind a CARD-containing polypeptide. CARD-specific antibodies be used, for example, for the immunoaffinity or affinity chromatography purification of an invention CARD-containing polypeptide, as well as for diagnostic and in vivo imaging procedures.

As used herein, the term "antibody" is used in its broadest sense to include polyclonal and monoclonal antibodies, as well as antigen binding fragments of such antibodies. With regard to an anti-CARD antibody of the invention, the term "antigen" means a native or synthesized CARD-containing polypeptide or fragment thereof. An anti-CARD antibody, or antigen binding fragment of such an antibody, is characterized by having specific binding activity for a CARD polypeptide or a peptide portion thereof of at least about $1\times10^5$ $M^{-1}$. Thus, Fab, $F(ab')_2$, Fd and Fv fragments of an anti-CARD antibody, which retain specific binding activity for a CARD-containing polypeptide, are included within the definition of an antibody. Specific binding activity of a CARD-containing polypeptide can be readily determined by one skilled in the art, for example, by comparing the binding activity of an anti-CARD antibody to a CARD-containing polypeptide versus a reference polypeptide that is not a CARD-containing polypeptide. Methods of preparing polyclonal or monoclonal antibodies are well known to those skilled in the art (see, for example, Harlow and Lane, *Antibodies: A Laboratory Manual*, Cold Spring Harbor Laboratory Press (1988)).

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275-1281 (1989)). These and other methods of making, for example, chimeric, humanized, CDR-grafted, single chain, and bifunctional antibodies are well known to those skilled in the art (Winter and Harris, *Immunol. Today* 14:243-246 (1993); Ward et al., *Nature* 341:544-546 (1989); Harlow and Lane, supra, 1988); Hilyard et al., *Protein Engineering: A practical approach* (IRL Press 1992); Borrabeck, *Antibody Engineering*, 2d ed. (Oxford University Press 1995)).

Anti-CARD antibodies can be raised using a CARD immunogen such as an isolated CARD-containing polypeptide having substantially the same amino acid sequence as SEQ ID NOS:2, 8 or 15, or an immunogenic fragment thereof, which can be prepared from natural sources or produced recombinantly, or a peptide portion of the CARD-containing polypeptide. A non-immunogenic or weakly immunogenic CARD-containing polypeptide or portion thereof can be made immunogenic by coupling the hapten to a carrier molecule such as bovine serum albumin (BSA) or keyhole limpet hemocyanin (KLH). Various other carrier molecules and methods for coupling a hapten to a carrier molecule are well known in the art (see, for example, Harlow and Lane, supra, 1988). An immunogenic CARD-containing polypeptide fragment can also be generated by expressing the peptide as a fusion protein, for example, to glutathione S transferase (GST), polyHis or the like. Methods for expressing peptide fusions are well known to those skilled in the art (Ausubel et al., supra, (2000)).

The invention further provides a method for detecting the presence of a human CARD-containing polypeptide in a sample by contacting a sample with a CARD-specific antibody, and detecting the presence of specific binding of the antibody to the sample, thereby detecting the presence of a human CARD-containing polypeptide in the sample. CARD-specific antibodies can be used in diagnostic methods and systems to detect the level of CARD-containing polypeptide present in a sample. With respect to the detection of such polypeptides, the antibodies can be used for in vitro diagnostic or in vivo imaging methods.

As used herein, the term "sample" is intended to mean any biological fluid, cell, tissue, organ or portion thereof, that includes or potentially includes CARD nucleic acids or polypeptides. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid or polypeptide preparation.

Immunological procedures useful for in vitro detection of target CARD-containing polypeptides in a sample include immunoassays that employ a detectable antibody. Such immunoassays include, for example, immunohistochemistry, immunofluorescence, ELISA assays, radioimmunoassay, FACS analysis, immunoprecipitation, immunoblot analysis, Pandex microfluorimetric assay, agglutination assays, flow cytometry and serum diagnostic assays, which are well known in the art (Harlow and Lane, supra, 1988; Harlow and Lane, *Using Antibodies: A Laboratory Manual*, Cold Spring Harbor Press (1999)).

An antibody can be made detectable by various means well known in the art. For example, a detectable marker can be directly attached to the antibody or indirectly attached using, for example, a secondary agent that recognizes the CARD specific antibody. Useful markers include, for example, radionucleotides, enzymes, binding proteins such as biotin, fluorogens, chromogens and chemiluminescent labels.

An antibody can also be detectable by, for example, a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189-231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., *Meth. Enzymol.*, 73:3-46 (1981). Conventional means of protein conjugation or coupling by activated functional groups are particularly applicable. See, for example, Aurameas et al., *Scand. J. Immunol.*, Vol. 8, Suppl. 7:7-23 (1978), Rodwell et al., *Biotech.*, 3:889-894 (1984), and U.S. Pat. No. 4,493,795.

In addition to detecting the presence of a CARD-containing polypeptide, invention anti-CARD antibodies are contemplated for use herein to alter the activity of the CARD-containing polypeptide in living animals, in humans, or in biological tissues or fluids isolated therefrom. Accordingly, compositions comprising a carrier and an amount of an antibody having specificity for CARD-containing polypeptides effective to block naturally occurring ligands or other CARD-associated polypeptides from binding to invention CARD-containing polypeptides are contemplated herein.

The present invention further provides transgenic non-human mammals that are capable of expressing exogenous nucleic acids encoding CARD-containing polypeptides. As employed herein, the phrase "exogenous nucleic acid" refers to nucleic acid sequence which is not native to the host, or which is present in the host in other than its native environment, for example, as part of a genetically engineered DNA construct. In addition to naturally occurring CARD-containing polypeptide levels, a CARD-containing polypeptide of the invention can either be overexpressed or underexpressed in transgenic mammals, for example, underexpressed in a knock-out animal.

Also provided are transgenic non-human mammals capable of expressing CARD-encoding nucleic acids so mutated as to be incapable of normal activity. Therefore, the transgenic non-human mammals do not express native CARD-containing polypeptide or have reduced expression of native CARD-containing polypeptide. The present invention also provides transgenic non-human mammals having a genome comprising antisense nucleic acids complementary to CARD-encoding nucleic acids, placed so as to be transcribed into antisense mRNA complementary to CARD-encoding mRNA, which hybridizes to the mRNA and, thereby, reduces the translation thereof. The nucleic acid can additionally comprise an inducible promoter and/or tissue specific regulatory elements, so that expression can be induced, or restricted to specific cell types.

Animal model systems useful for elucidating the physiological and behavioral roles of CARD-containing polypeptides are also provided, and are produced by creating transgenic animals in which the expression of the CARD-containing polypeptide is altered using a variety of techniques. Examples of such techniques include the insertion of normal or mutant versions of nucleic acids encoding a CARD-containing polypeptide by microinjection, retroviral infection or other means well known to those skilled in the art, into appropriate fertilized embryos to produce a transgenic animal, see, for example, Hogan et al., *Manipulating the Mouse Embryo: A Laboratory Manual* (Cold Spring Harbor Laboratory, (1986)). Transgenic animal model systems are useful for in vivo screening of compounds for identification of specific ligands, such as agonists or antagonists, which activate or inhibit a biological activity.

Also contemplated herein, is the use of homologous recombination of mutant or normal versions of CARD-encoding genes with the native gene locus in transgenic animals, to alter the regulation of expression or the structure of CARD-containing polypeptides by replacing the endogeneous gene with a recombinant or mutated CARD-encoding gene. Methods for producing a transgenic non-human mammal including a gene knock-out non-human mammal, are well known to those skilled in the art (see, Capecchi et al., *Science* 244:1288 (1989); Zimmer et al., *Nature* 338:150 (1989); Shastry, *Experentia*, 51:1028-1039 (1995); Shastry, *Mol. Cell. Biochem.*, 181:163-179 (1998); and U.S. Pat. No. 5,616,491, issued Apr. 1, 1997, No. 5,750,826, issued May 12, 1998, and No. 5,981,830, issued Nov. 9, 1999).

In addition to homologous recombination, additional methods such as microinjection can be used which add genes to the host genome without removing host genes. Microinjection can produce a transgenic animal that is capable of expressing both endogenous and exogenous CARD-containing polypeptides. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists which activate or inhibit CARD-containing polypeptide responses.

In accordance with another embodiment of the invention, a method is provided for identifying a CARD-associated polypeptide (CAP). The method is carried out by contacting an invention CARD-containing polypeptide with a candidate CAP and detecting association of the CARD-containing polypeptide with the CAP.

As used herein, the term "CARD-associated polypeptide" or "CAP" means a polypeptide that can specifically bind to the CARD-containing polypeptides of the invention, or to any functional fragment of a CARD-containing polypeptide of the invention. Because CARD-containing polypeptides of the invention contain domains which can self-associate, other CARD-containing polypeptides are exemplary CAPs. Other exemplary CAPs are proteins and fragments thereof that can bind a CARD, ERM, PDZ or filament domain of an invention CARD-containing polypeptide. For example, cytoskeletal components that bind the filament domain of CARD-10X or the ERM domain of CARD-11X are exemplary CAPs.

A CAP can be identified and its binding with a CARD-containing polypeptide of the invention further characterized, for example, using in vitro protein binding assays similar to those described in, for example, Ausubel et al., supra, 2000, including co-immunoprecipitation assays, sedimentation assays, affinity chromatography, gel-overlay assays, radiolabeled ligand binding assays, surface plasmon resonance (SPR) on BIAcore, nuclear magnetic resonance (NMR) spectroscopy, circular dichroism (CD) spectroscopy, and mass spectroscopy. A CAP can also be identified and characterized in vivo using protein-interaction assays and methods known in the art, including yeast two-hybrid assays and FRET-based binding assays.

Normal association of CARD-containing polypeptide and a CAP polypeptide in a cell can be altered due, for example, to the expression in the cell of a variant CAP or CARD-containing polypeptide, respectively, either of which can compete with the normal binding function of a CARD-containing polypeptide and, therefore, can decrease the association of CAP and CARD-containing polypeptides in a cell. The term "variant" is used generally herein to mean a polypeptide that is different from the CAP or CARD-containing polypeptide that normally is found in a particular cell type. Thus, a variant can include a mutated protein or a naturally occurring protein, such as an isoform, that is not normally found in a particular cell type.

As used herein, a "candidate CAP" refers to a polypeptide containing a sequence known or suspected of binding one or more CARD-containing polypeptides of the invention. Thus, a CAP can represent a full-length protein or a CARD-associating fragment thereof. Likewise, a CAP-encoding nucleic acid need not encode the full-length protein, but only the CARD-associating fragment of the CAP.

Since CARD-containing polypeptides can be involved in apoptosis and anoikis, the association of a CAP with a CARD-containing polypeptide can affect the sensitivity or resistance of a cell to apoptosis or can induce or block apoptosis induced by external or internal stimuli. The identification of various CAPs by use of known methods can be used to determine the function of these CAPs in cell death or signal transduction pathways controlled by CARD-containing polypeptides, allowing for the development of assays that are useful for identifying agents that effectively alter the association of a CAP with a CARD-containing polypeptide. Such agents can be useful for providing effective therapy for conditions caused, at least in part, by insufficient apoptosis, such as a cancer, autoimmune disease or certain viral infections. Such agents can also be useful for providing an effective therapy for diseases where excessive apoptosis is known to occur, such as stroke, heart failure, or AIDS.

A further embodiment of the invention provides a method to identify agents that can effectively alter CARD-containing polypeptide activity, for example the ability of CARD-containing polypeptides to associate with one or more CAPs. Thus, the present invention provides a screening assay useful for identifying an effective agent, which can alter the association of a CARD-containing polypeptide with a CARD-associated polypeptide (CAP), such as a heterologous CARD-containing polypeptide. Since CARD-containing polypeptides are involved in biochemical processes such as apoptosis, the identification of such effective agents can be useful for altering the level of a biochemical process such as apoptosis in a cell, for example in a cell of a subject having a pathology characterized by an increased or decreased level of apoptosis.

Further, effective agents can be useful for alteration of other biochemical process modulated by a CARD-containing polypeptide of the invention, including, for example, NF-κB induction, cytokine processing, cytokine receptor signaling, caspase-mediated proteolysis, cytoskeletal integrity, inflammation and cell adhesion.

As used herein, the term "agent" means a chemical or biological molecule such as a simple or complex organic molecule, a peptide, a peptido-mimetic, a polypeptide, a protein or an oligonucleotide that has the potential for altering the association of a CARD-containing polypeptide with a heterologous protein or altering the ability of a CARD-containing polypeptide to self-associate or altering the ligand binding or catalytic activity of a CARD-containing polypeptide. An exemplary ligand binding activity is nucleotide binding activity, such as ADP or ATP binding activity; and exemplary catalytic activities are nucleotide hydrolytic activity and proteolytic activity. In addition, the term "effective agent" is used herein to mean an agent that is confirmed as capable of altering the association of a CARD-containing polypeptide with a heterologous protein or altering the ability of a CARD-containing polypeptide to self-associate or altering the ligand binding or catalytic activity of a CARD-containing polypeptide. For example, an effective agent may be an anti-CARD antibody, a CARD-associated polypeptide, a caspase inhibitor, and the like.

As used herein, the term "alter the association" means that the association between two specifically interacting polypeptides either is increased or decreased due to the presence of an effective agent. As a result of an altered association of CARD-containing polypeptide with another polypeptide in a cell, the activity of the CARD-containing polypeptide or the CAP can be increased or decreased, thereby altering a biochemical process, for example, the level of apoptosis in the cell. As used herein, the term "alter the activity" means that the agent can increase or decrease the activity of a CARD-containing polypeptide in a cell, thereby modulating a biochemical process in a cell, for example, the level of apoptosis in the cell. Similarly, the term "alter the level" of a biological process modulated by a CARD-containing polypeptide refers to an increase or decrease a biochemical process which occurs upon altering the activity of a CARD-containing polypeptide. For example, an effective agent can increase or decrease the CARD:CARD-associating activity of a CARD-containing polypeptide, which can result in decreased apoptosis. An effective agent can also increase or decrease the association between the ERM domain, filament domain or PDZ domain of a polypeptide of the invention and a cellular component, thereby altering cytoskeletal organization.

An effective agent can act by interfering with the ability of a CARD-containing polypeptide to associate with another polypeptide, or can act by causing the dissociation of a CARD-containing polypeptide from a complex with a CARD-associated polypeptide, wherein the ratio of bound CARD-containing polypeptide to free CARD-containing polypeptide is related to the level of a biochemical process, such as, apoptosis, in a cell. For example, binding of a ligand to a CAP can allow the CAP, in turn, to bind a specific CARD-containing polypeptide such that all of the specific CARD-containing polypeptide is bound to a CAP, and can result in decreased apoptosis. The association, for example, of a CARD-containing polypeptide and a CARD-containing polypeptide can result in activation or inhibition of the NB-ARC:NB-ARC-associating activity of a CARD-containing polypeptide. In the presence of an effective agent, the association of a CARD-containing polypeptide and a CAP can be altered, which can, for example, alter the activation of caspases in the cell. As a result of the altered caspase activation, the level of apoptosis in a cell can be increased or decreased. Thus, the identification of an effective agent that alters the association of a CARD-containing polypeptide with another polypeptide can allow for the use of the effective agent to increase or decrease the level of a biological process such as apoptosis.

An effective agent can be useful, for example, to increase the level of apoptosis in a cell such as a cancer cell, which is characterized by having a decreased level of apoptosis as compared to its normal cell counterpart. An effective agent also can be useful, for example, to decrease the level of apoptosis in a cell such as a T lymphocyte in a subject having a viral disease such as acquired immunodeficiency syndrome, which is characterized by an increased level of apoptosis in an infected T cell as compared to a normal T cell. Thus, an effective agent can be useful as a medicament for altering the level of apoptosis in a subject having a pathology characterized by increased or decreased apoptosis. In addition, an effective agent can be used, for example, to decrease the level of apoptosis and, therefore, increase the survival time of a cell such as a hybridoma cell in culture. The use of an effective agent to prolong the survival of a cell in vitro can significantly improve bioproduction yields in industrial tissue culture applications.

It will be appreciated that a functional fragment or peptide of a CARD-containing polypeptide or a CAP can be an effective agent, so long as it alters the association between a CARD-containing polypeptide and a CAP. Such peptides, which can be as small as about five amino acids, can be identified, for example, by screening a peptide library (see, for example, Ladner et al., U.S. Pat. No. 5,223,409, which is incorporated herein by reference) to identify peptides that can bind a CARD-containing polypeptide or a CARD-associated polypeptide.

Such peptide effective agents can act by decreasing the association of a CARD-containing polypeptide with a CAP in a cell by competing for binding to the CARD-containing polypeptide. A non-naturally occurring peptido-mimetic also can be useful as an effective agent. Such a peptido-mimetic can include, for example, a peptoid, which is peptide-like sequence containing N-substituted glycines, or an oligocarbamate. A peptido-mimetic can be particularly useful as an effective agent due, for example, to having an increased stability to enzymatic degradation in vivo.

In accordance with another embodiment of the present invention, there is provided a method of identifying an effective agent that alters the association of an invention CARD-containing polypeptide with a CARD-associated polypeptide (CAP), by the steps of:

(a) contacting the CARD-containing polypeptide and CAP polypeptide under conditions that allow the polypeptides to associate, with an agent suspected of being able to alter the association of the CARD-containing polypeptide and CAP polypeptides; and (b) determining association of the CARD-containing polypeptide and the CAP polypeptide, where an agent that alters the association is identified as an effective agent.

Methods are well-known in the art for detecting the altered association of the CARD-containing polypeptide and CAP polypeptides, for example, measuring protein:protein binding, protein degradation or apoptotic activity can be employed in bioassays described herein to identify agents as agonists or antagonists of CARD-containing polypeptides. As described herein, CARD-containing polypeptides have the ability to self-associate. Thus, methods for identifying effective agents that alter the association of a CARD-containing polypeptide with a CAP are useful for identifying effective agents that alter the ability of a CARD-containing polypeptide to self-associate.

As used herein, "conditions that allow a CARD-containing polypeptide and a CAP polypeptide to associate" refers to environmental conditions in which a CARD-containing polypeptide and CAP specifically associate. Such conditions will typically be aqueous conditions, with a pH between 3.0 and 11.0, and temperature below 100° C. Preferably, the conditions will be aqueous conditions with salt concentrations below the equivalent of 1 M NaCl, and pH between 5.0 and 9.0, and temperatures between 0° C. and 50° C. Most preferably, the conditions will range from physiological conditions of normal yeast or mammalian cells, or conditions favorable for carrying out in vitro assays such as immunoprecipitation and GST protein:protein association assays, and the like.

The present invention also provides in vitro screening assays. Such screening assays are particularly useful in that they can be automated, which allows for high through-put screening, for example, of randomly or rationally designed agents such as drugs, peptidomimetics or peptides in order to identify those agents that effectively alter the association of a CARD-containing polypeptide and a CAP or the catalytic or ligand binding activity of a CARD-containing polypeptide and, thereby, alter a biochemical process modulated by a CARD-containing polypeptide such as apoptosis. An in vitro screening assay can utilize, for example, a CARD-containing polypeptide including a CARD-containing fusion protein such as a CARD-glutathione-S-transferase fusion protein. For use in the in vitro screening assay, the CARD-containing polypeptide should have an affinity for a solid substrate as well as the ability to associate with a CARD-associated polypeptide. For example, when a CARD-containing polypeptide is used in the assay, the solid substrate can contain a covalently attached anti-CARD antibody. Alternatively, a GST/CARD fusion protein can be used in the assay and the solid substrate can contain covalently attached glutathione, which is bound by the GST component of the GST/CARD fusion protein. Similarly, a CARD-associated polypeptide can be used in such screening assays.

An in vitro screening assay can be performed, for example, by allowing a CARD-containing polypeptide to bind to the solid support, then adding a CARD-associated polypeptide and an agent to be tested. Reference reactions, which do not contain an agent, can be performed in parallel. Following incubation under suitable conditions, which include, for example, an appropriate buffer concentration and pH and time and temperature that permit binding of the particular CARD-containing polypeptide and CARD-associated polypeptide, the amount of protein that has associated in the absence of an agent and in the presence of an agent can be determined. The association of a CARD-associated polypeptide with a CARD-containing polypeptide can be detected, for example, by attaching a detectable moiety such as a radionuclide or a fluorescent label to a CARD-associated polypeptide and measuring the amount of label that is associated with the solid support, wherein the amount of label detected indicates the amount of association of the CARD-associated polypeptide with a CARD-containing polypeptide. An effective agent is determined by comparing the amount of specific binding in the presence of an agent as compared to a reference level of binding, wherein an effective agent alters the association of CARD-containing polypeptide with the CARD-associated polypeptide. Such an assay is particularly useful for screening a panel of agents such as a peptide library in order to detect an effective agent.

Various binding assays to identify cellular proteins that interact with protein binding domains are known in the art and include, for example, yeast two-hybrid screening assays (see, for example, U.S. Pat. Nos. 5,283,173, 5,468,614 and 5,667,973; Ausubel et al., supra, 2000; Luban et al., *Curr. Opin. Biotechnol.* 6:59-64 (1995)) and affinity column chromatography methods using cellular extracts. By synthesizing or expressing polypeptide fragments containing various CARD-associating sequences or deletions, the CARD binding interface can be readily identified.

Another assay for screening of agents that alter the activity of a CARD-containing polypeptide is based on altering the phenotype of yeast by expressing a CARD-containing polypeptide. In one embodiment, expression of a CARD-containing polypeptide can be inducible (Tao et al., *J. Biol. Chem.* 273:23704-23708 (1998), and the compounds can be screened when CARD-containing polypeptide expression is induced. CARD-containing polypeptides of the invention can also be co-expressed in yeast with CAP polypeptides used to screen for compounds that antagonize the activity of the CARD-containing polypeptide.

Also provided by the present invention are assays to identify agents that alter CARD-containing polypeptide expression. Methods to determine CARD-containing polypeptide expression can involve detecting a change in CARD-containing polypeptide abundance in response to contacting the cell with an agent that modulates CARD-containing polypeptide expression. Assays for detecting changes in polypeptide expression include, for example, immunoassays with CARD-specific antibodies, such as immunoblotting, immunofluorescence, immunohistochemistry and immunoprecipitation assays, as described herein.

As understood by those of skill in the art, assay methods for identifying agents that alter. CARD-containing polypeptide activity generally require comparison to a reference. One type of a "reference" is a cell or culture that is treated substantially the same as the test cell or test culture exposed to the agent, with the distinction that the "reference" cell or culture is not exposed to the agent. Another type of "reference" cell or culture can be a cell or culture that is identical to the test cells, with the exception that the "reference" cells or culture do not express a CARD-containing polypeptide. Accordingly, the response of the transfected cell to an agent is compared to the response, or lack thereof, of the "reference" cell or culture to the same agent under the same reaction conditions.

Methods for producing pluralities of agents to use in screening for compounds that alter the activity of a CARD-containing polypeptide, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.*, 2:363-371 (1998); Sofia, *Mol. Divers.* 3:75-94 (1998); Eichler et al., *Med. Res. Rev.* 15:481-496 (1995); and the like. Libraries containing large numbers of natural and synthetic agents also can be obtained from commercial sources. Combinatorial libraries of molecules can be prepared using well known combinatorial chemistry methods (Gordon et al., *J. Med. Chem.* 37: 1233-1251 (1994); Gordon et al., *J. Med. Chem.* 37: 1385-1401 (1994); Gordon et al., *Acc. Chem. Res.* 29:144-154 (1996); Wilson and Czarnik, eds., *Combinatorial Chemistry: Synthesis and Application*, John Wiley & Sons, New York (1997)).

The invention further provides a method of diagnosing or predicting clinical prognosis of a pathology characterized by an increased or decreased level of a CARD-containing polypeptide in a subject. The method includes the steps of (a) obtaining a test sample from the subject; (b) contacting the sample with an agent that can bind a CARD-containing polypeptide or nucleic acid molecule of the invention under suitable conditions, wherein the conditions allow specific binding of the agent to the CARD-containing polypeptide; and (c) comparing the amount of the specific binding in the test sample with the amount of specific binding in a reference sample, wherein an increased or decreased amount of the specific binding in the test sample as compared to the reference sample is diagnostic of, or predictive of the clinical prognosis of, a pathology. The agent can be, for example, an anti-CARD antibody, a CARD-associated-polypeptide (CAP), or a CARD-encoding nucleic acid.

Exemplary pathologies for diagnosis or the prediction of clinical prognosis include any of the pathologies described herein, such as neoplastic pathologies (e.g. cancer), autoimmune diseases, and other pathologies related to abnormal cell proliferation or abnormal cell death (e.g. apoptosis), as disclosed herein.

The invention also provides a method of diagnosing cancer or monitoring cancer therapy by contacting a test sample from a patient with a CARD-specific antibody. The invention additionally provides a method of assessing prognosis (e.g., predicting the clinical prognosis) of patients with cancer comprising contacting a test sample from a patient with a CARD-specific antibody.

The invention additionally provides a method of diagnosing cancer or monitoring cancer therapy by contacting a test sample from a patient with a oligonucleotide that selectively hybridizes to a CARD-encoding nucleic acid molecule. The invention further provides a method of assessing prognosis (e.g., predicting the clinical prognosis) of patients with cancer by contacting a test sample from a patient with a oligonucleotide that selectively hybridizes to a CARD-encoding nucleic acid molecule.

The methods of the invention for diagnosing cancer or monitoring cancer therapy using a CARD-specific antibody or oligonucleotide or nucleic acid that selectively hybridizes to a CARD-encoding nucleic acid molecule can be used, for example, to segregate patients into a high risk group or a low risk group for diagnosing cancer or predicting risk of metastasis or risk of failure to respond to therapy. Therefore, the methods of the invention can be advantageously used to determine, for example, the risk of metastasis in a cancer patient, or the risk of an autoimmune disease of a patient, or as a prognostic indicator of survival or disease progression in a cancer patient or patient with an autoimmune disease. One of ordinary skill in the art would appreciate that the prognostic indicators of survival for cancer patients suffering from stage I cancer can be different from those for cancer patients suffering from stage IV cancer. For example, prognosis for stage I cancer patients can be oriented toward the likelihood of continued growth and/or metastasis of the cancer, whereas prognosis for stage IV cancer patients can be oriented toward the likely effectiveness of therapeutic methods for treating the cancer. Accordingly, the methods of the invention directed to measuring the level of or determining the presence of a CARD-containing polypeptide or CARD-encoding nucleic acid can be used advantageously as a prognostic indicator for the presence or progression of a cancer or response to therapy.

The present invention also provides therapeutic compositions useful for practicing the therapeutic methods described herein. Therapeutic compositions of the present invention, such as pharmaceutical compositions, contain a physiologically compatible carrier together with an invention CARD-containing polypeptide (or functional fragment thereof), an invention CARD-encoding nucleic acid, an agent that alters CARD activity or expression identified by the methods described herein, or an anti-CARD antibody, as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically compatible" and grammatical variations thereof, as they refer to compositions, carriers, diluents and reagents, are used interchangeably and represent that the materials are capable of administration to a mammal without the production of undesirable physiological effects such as nausea, dizziness, gastric upset, and the like.

The preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient in amounts suitable for use in the therapeutic methods described herein. Suitable excipients are, for example, water, saline, dextrose, glycerol, ethanol, or the like, as well as combinations of any two or more thereof. In addition, if desired, the composition can contain minor amounts of auxiliary substances such as wetting or emulsifying agents, pH buffering agents, and the like, which enhance the effectiveness of the active ingredient.

The therapeutic composition of the present invention can include pharmaceutically acceptable salts of the components therein. Pharmaceutically acceptable nontoxic salts include the acid addition salts (formed with the free amino groups of the polypeptide) that are formed with inorganic acids such as, for example, hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Salts formed with the free carboxyl groups can also be derived from inorganic bases such as, for example, sodium hydroxide, ammonium hydroxide, potassium hydroxide, and the like; and organic bases such as mono-, di-, and tri-alkyl and -aryl amines (e.g., triethylamine, diisopropyl amine, methyl amine, dimethyl amine, and the like) and optionally substituted ethanolamines (e.g., ethanolamine, diethanolamine, and the like).

Physiologically tolerable carriers are well known in the art. Exemplary liquid carriers are sterile aqueous solutions that contain no materials in addition to the active ingredients and water, or contain a buffer such as sodium phosphate at physiological pH, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary additional liquid phases include glycerin, vegetable oils such as cottonseed oil, and water-oil emulsions.

As described herein, an "effective amount" is a predetermined amount calculated to achieve the desired therapeutic effect, i.e., to alter the protein binding activity of a CARD-containing polypeptide or other biological activity, resulting in altered biochemical process modulated by a CARD-containing polypeptide. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such agents in depot or long-lasting form as discussed herein. A therapeutically effective amount is typically an amount of an agent identified herein that, when administered in a physiologically acceptable composition, is sufficient to achieve a plasma concentration of from about 0.1 µg/ml to about 100 µg/ml, preferably from about 1.0 µg/ml to about 50 µg/ml, more preferably at least about 2 µg/ml and usually 5 to 10 µg/ml. Therapeutic invention anti-CARD antibodies can be administered in proportionately appropriate amounts in accordance with known practices in this art.

Also provided herein are methods of treating pathologies characterized by abnormal cell proliferation, abnormal cell death, or inflammation said method comprising administering an effective amount of an invention therapeutic composition. Such compositions are typically administered in a physiologically compatible composition.

Exemplary abnormal cell proliferation diseases associated with CARD-containing polypeptides contemplated herein for treatment according to the present invention include cancer pathologies, keratinocyte hyperplasia, neoplasia, keloid, benign prostatic hypertrophy, inflammatory hyperplasia, fibrosis, smooth muscle cell proliferation in arteries following balloon angioplasty (restenosis), and the like. Exemplary cancer pathologies contemplated herein for treatment include, gliomas, carcinomas, adenocarcinomas, sarcomas, melanomas, hamartomas, leukemias, lymphomas, and the like. Further diseases associated with CARD-containing polypeptides contemplated herein for treatment according to the present invention include inflammatory diseases and diseases of cell loss. Such diseases include allergies, inflammatory diseases including arthritis, lupus, Schrogen's syndrome, Crohn's disease, ulcerative colitis, as well as allograft rejection, such as graft-versus-host disease, and the like. CARD-containing polypeptides can also be useful in design of strategies for preventing diseases related to abnormal cell death in conditions such as stroke, myocardial infarction, heart failure, neurodegenerative diseases such as Parkinson's and Alzheimer's diseases, and for immunodeficiency associated diseases such as HIV infection, HIV-related disease, and the like.

Methods of treating pathologies can include methods of modulating the activity of one or more oncogenic proteins, wherein the oncogenic proteins specifically interact with a CARD-containing polypeptide of the invention. Methods of modulating the activity of such oncogenic proteins will include contacting the oncogenic protein with a substantially pure CARD-containing polypeptide or an active fragment (i.e., oncogenic protein-binding fragment) thereof. This contacting will alter the activity of the oncogenic protein, thereby providing a method of treating a pathology caused by the oncogenic protein. Further methods of modulating the activity of oncogenic proteins will include contacting the oncogenic protein with an agent, wherein the agent alters interaction between a CARD-containing polypeptide and an oncogenic protein.

Also contemplated herein, are therapeutic methods using invention pharmaceutical compositions for the treatment of pathological disorders in which there is too little cell division, such as, for example, bone marrow aplasias, immunodeficiencies due to a decreased number of lymphocytes, and the like. Methods of treating a variety of inflammatory diseases with invention therapeutic compositions are also contemplated herein, such as treatment of sepsis, fibrosis (e.g., scarring), arthritis, graft versus host disease, and the like.

The present invention also provides methods for diagnosing a pathology that is characterized by an increased or decreased level of a biochemical process to determine whether the increased or decreased level of the biochemical process is due, for example, to increased or decreased expression of a CARD-containing polypeptide or to expression of a variant CARD-containing polypeptide. As disclosed herein, such biochemical processes include apoptosis, NF-κB induction, cytokine processing, caspase-mediated proteolysis, transcription, inflammation, cell adhesion, cytoskeletal integrity and the like.

The identification of such a pathology can allow for intervention therapy using an effective agent, nucleic acid molecule, antisense oligonucleotide or polypeptide as described herein. In general, a test sample can be obtained from a subject having a pathology characterized by having or suspected of having increased or decreased apoptosis and can be compared to a reference sample from a normal subject to determine whether a cell in the test sample has, for example, increased or decreased expression of a CARD-encoding gene. The level of a CARD-containing polypeptide in a cell can be determined by contacting a sample with a reagent such as an anti-CARD antibody or a CARD-associated polypeptide, either of which can specifically bind a CARD-containing polypeptide. For example, the level of a CARD-containing polypeptide in a cell can determined by well known immunoassay or immunohistochemical methods using an anti-CARD antibody (see, for example, Reed et al., *Anal. Biochem.* 205:70-76 (1992); see, also, Harlow and Lane, supra, (1988)).

As used herein, the term "reagent" means a chemical or biological molecule that can specifically bind to a CARD-containing polypeptide or to a bound CARD/CARD-associated polypeptide complex. For example, either an anti-CARD antibody or a CARD-associated polypeptide can be a reagent for a CARD-containing polypeptide, whereas either an anti-CARD antibody or an anti-CARD-associated polypeptide antibody can be a reagent for a CARD/CARD-associated polypeptide complex.

Increased or decreased expression of a CARD-encoding gene in a cell in a test sample can be determined, for example, by comparison to an expected normal level of CARD-containing polypeptide or CARD-encoding mRNA in a particular cell type. A normal range of CARD-containing polypeptide or CARD-encoding mRNA levels in various cell types can be determined by sampling a statistically significant number of normal subjects. In addition, a reference sample can be evaluated in parallel with a test sample in order to determine whether a pathology characterized by increased or decreased apoptosis is due to increased or decreased expression of a CARD-encoding gene. The test sample can be examined using, for example, immunohistochemical methods as described above or the sample can be further processed and examined. For example, an extract of a test sample can be prepared and examined to determine whether a CARD-containing polypeptide in the sample can associate with a CARD-associated polypeptide in the same manner as a CARD-containing polypeptide from a reference cell or whether, instead, a variant CARD-containing polypeptide is expressed in the cell.

In accordance with another embodiment of the present invention, there are provided diagnostic systems, preferably in kit form, comprising at least one invention CARD-encoding nucleic acid, CARD-containing polypeptide, and/or anti-CARD antibody described herein, in a suitable packaging material. In one embodiment, for example, the diagnostic nucleic acids are derived from any of SEQ ID NOS:1, 7 or 15. Invention diagnostic systems are useful for assaying for the presence or absence of CARD-encoding nucleic acid in either genomic DNA or in transcribed CARD-encoding nucleic acid, such as mRNA or cDNA.

A suitable diagnostic system includes at least one invention CARD-encoding nucleic acid, CARD-containing polypeptide, and/or anti-CARD antibody, preferably two or more invention nucleic acids, proteins and/or antibodies, as a separately packaged chemical reagent(s) in an amount sufficient for at least one assay. Instructions for use of the packaged reagent are also typically included. Those of skill in the art can readily incorporate invention nucleic acid probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular CARD-encoding sequence including the nucleotide sequences set forth in SEQ ID NOS: 1, 7 or 15 or mutations or deletions therein, thereby diagnosing the presence of, or a predisposition for a pathology such as cancer or an autoimmune disease. In addition, the packaging material contains instructions indicating how the materials within the kit are employed both to detect a particular sequence and diagnose the presence of, or a predisposition for a pathology such as cancer or an autoimmune disease.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

A diagnostic assay should include a simple method for detecting the amount of a CARD-containing polypeptide or CARD-encoding nucleic acid in a sample that is bound to the reagent. Detection can be performed by labeling the reagent and detecting the presence of the label using well known methods (see, for example, Harlow and Lane, supra, 1988; chap. 9, for labeling an antibody). A reagent can be labeled with various detectable moieties including a radiolabel, an enzyme, biotin or a fluorochrome. Materials for labeling the reagent can be included in the diagnostic kit or can be purchased separately from a commercial source. Following contact of a labeled reagent with a test sample and, if desired, a control sample, specifically bound reagent can be identified by detecting the particular moiety.

A labeled antibody that can specifically bind the reagent also can be used to identify specific binding of an unlabeled reagent. For example, if the reagent is an anti-CARD antibody, a second antibody can be used to detect specific binding of the anti-CARD antibody. A second antibody generally will be specific for the particular class of the first antibody. For example, if an anti-CARD antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, then the sample is contacted with the labeled second antibody, which specifically binds to the first antibody and results in a labeled sample.

In accordance with another embodiment of the invention, there are provided methods for determining a prognosis of disease free or overall survival in a patient suffering from cancer. For example, it is contemplated herein that abnormal levels of CARD-containing polypeptides (either higher or lower) in primary tumor tissue show a high correlation with either increased or decreased tumor recurrence or spread, and therefore indicates the likelihood of disease free or overall survival. Thus, the present invention advantageously provides a significant advancement in cancer management because early identification of patients at risk for tumor recurrence or spread will permit aggressive early treatment with significantly enhanced potential for survival. Also provided are methods for predicting the risk of tumor recurrence or spread in an individual having a cancer tumor; methods for screening a cancer patient to determine the risk of tumor metastasis; and methods for determining the proper course of treatment for a patient suffering from cancer. These methods are carried out by collecting a sample from a patient and comparing the level of CARD-encoding gene expression in the patient to the level of expression in a control or to a reference level of CARD-encoding gene expression as defined by patient population sampling, tissue culture analysis, or any other method known for determining reference levels for determination of disease prognosis. The level of CARD-encoding gene expression in the patient is then classified as higher than the reference level or lower than the reference level, wherein the prognosis of survival or tumor recurrence is different for patients with higher levels than the prognosis for patients with lower levels.

The following examples are intended to illustrate but not limit the present invention.

EXAMPLE I

Identification of CARD-Containing Polypeptides

CARD-10X, -11X and -12X proteins were identified using Saturated Blast searches (Li et al., "Saturated BLAST: An automated multiple intermediate sequence search used to detect distant homology," *Bioinformatics* (2000), in press). A representative set of CARD domains was used as queries and a cascade of TBLASTN and PSI-BLAST searches was performed on nucleotide databases at NCBI (htgs, gss, dbest) and the NR protein database.

The new candidate CARD-domains were confirmed by:

1) Determining whether the identified nucleotide sequence falls within an exon as predicted by the GENSCAN program.

2) Identifying EST sequences corresponding to the novel CARD domain.

3) Performing a FFAS fold prediction calculation against a database of proteins of known structures (PDB) enriched in apoptotic domains (Rychlewski et al., *Protein Science* 9:232-241 (2000)).

4) Performing a PSI-BLAST search against the NR protein database.

The novelty of the discovered CARD domain was assessed by:

1) Performing a PSI-BLAST search against the NR protein database at NCBI.

2) Performing a PSI-BLAST search against a database of known CARD domains.

3) Performing a BLASTN search (using the nucleotide sequences of CARD-10X, 11X, 12X) against the NR nucleotide database at NCBI.

Additional domains in CARD-10X, 11X, 12X (e.g. PDZ, domain, filament domain) were identified by performing an exon prediction (GENSCAN) analysis for full genomic contigs in which the CARD domains were found.

The protein sequences obtained in this way were used as queries for FFAS searches against the PDB, PFAM and COG databases, as well as for HMM searches in the PFAM database (Bateman et al., *Nucleic Acids Res.* 27:260-262 (1999)).

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

SEQUENCE LISTING

<160> NUMBER OF SEQ ID NOS: 37

<210> SEQ ID NO 1
<211> LENGTH: 1101
<212> TYPE: DNA
<213> ORGANISM: Homo sapiens
<220> FEATURE:
<221> NAME/KEY: CDS
<222> LOCATION: (1)...(1101)

<400> SEQUENCE: 1

```
atg tcg gac tac gag aac gat gac gag tgc tgg aac gtc ctg gag ggc        48
Met Ser Asp Tyr Glu Asn Asp Asp Glu Cys Trp Asn Val Leu Glu Gly
 1               5                  10                  15 ttc cgg gtg acg ctc acc tcg gtc atc gac ccc tca cgc atc aca cct        96
Phe Arg Val Thr Leu Thr Ser Val Ile Asp Pro Ser Arg Ile Thr Pro
                20                  25                  30 tac ctg cgg cag tgc aag gtc ctg aac cct gat gat gag gag cag gtg       144
Tyr Leu Arg Gln Cys Lys Val Leu Asn Pro Asp Asp Glu Glu Gln Val
            35                  40                  45 ctc agc gac ccc aac ctg gtc atc cgc aaa cgg aaa gtg ggt gtg ctc       192
Leu Ser Asp Pro Asn Leu Val Ile Arg Lys Arg Lys Val Gly Val Leu
 50                  55                  60 ctg gac atc ctg cag cgg acc ggc cac aag ggc tac gtg gcc ttc ctc       240
Leu Asp Ile Leu Gln Arg Thr Gly His Lys Gly Tyr Val Ala Phe Leu
 65                  70                  75                  80 gag agc ctg gag ctc tac tac ccg cag ctg tac aag aag gtc aca ggc       288
Glu Ser Leu Glu Leu Tyr Tyr Pro Gln Leu Tyr Lys Lys Val Thr Gly
                85                  90                  95 aag gag ccg gcc cgc gtc ttc tcc atg atc atc gac gcg tcc ggg gag       336
Lys Glu Pro Ala Arg Val Phe Ser Met Ile Ile Asp Ala Ser Gly Glu
            100                 105                 110 tca ggc ctg act cag ctg ctg atg act gag gtc atg aag ctg cag aag       384
Ser Gly Leu Thr Gln Leu Leu Met Thr Glu Val Met Lys Leu Gln Lys
        115                 120                 125 aag gtg cag gac ctg acc gcg ctg ctg agc tcc aaa gat gac ttc atc       432
Lys Val Gln Asp Leu Thr Ala Leu Leu Ser Ser Lys Asp Asp Phe Ile
    130                 135                 140 aag gag ctg cgg gtg aag gac agc ctg ctg cgc aag cac cag gag cgt       480
Lys Glu Leu Arg Val Lys Asp Ser Leu Leu Arg Lys His Gln Glu Arg
145                 150                 155                 160 gtg cag agg ctc aag gag gag tgc gag gcc ggc agc cgc gag ctc aag       528
Val Gln Arg Leu Lys Glu Glu Cys Glu Ala Gly Ser Arg Glu Leu Lys
                165                 170                 175 cgc tgc aag gag gag aac tac gac ctg gcc atg cgc ctg gcg cac cag       576
Arg Cys Lys Glu Glu Asn Tyr Asp Leu Ala Met Arg Leu Ala His Gln
            180                 185                 190 agt gag gag aag ggc gcc gcg ctc atg cgg aac cgt gac ctg cag ctg       624
Ser Glu Glu Lys Gly Ala Ala Leu Met Arg Asn Arg Asp Leu Gln Leu
        195                 200                 205 gag att gac cag ctc aag cac agc ctc atg aag gcc gag gac gac tgc       672
Glu Ile Asp Gln Leu Lys His Ser Leu Met Lys Ala Glu Asp Asp Cys
    210                 215                 220 aag gtg gag cgc aag cac acg ctg aag ctc agg cac gcc atg gag cag       720
Lys Val Glu Arg Lys His Thr Leu Lys Leu Arg His Ala Met Glu Gln
225                 230                 235                 240 cgg ccc agc cag gag ctg ctg tgg gag ctg cag cag gag aag gcc ctg       768
Arg Pro Ser Gln Glu Leu Leu Trp Glu Leu Gln Gln Glu Lys Ala Leu
                245                 250                 255
```

```
ctc cag gcc cgg gtg cag gag ctg gag gcc tcc gtc cag gag ggg aag      816
Leu Gln Ala Arg Val Gln Glu Leu Glu Ala Ser Val Gln Glu Gly Lys
        260                 265                 270 ctg gac agg agc agc ccc tac atc cag gta ctg gag gag gac tgg cgg      864
Leu Asp Arg Ser Ser Pro Tyr Ile Gln Val Leu Glu Glu Asp Trp Arg
275                 280                 285 cag gcg ctg cgg gac cac cag gag cag gcc aac acc atc ttc tcc ctg      912
Gln Ala Leu Arg Asp His Gln Glu Gln Ala Asn Thr Ile Phe Ser Leu
            290                 295                 300 cgc aag gac ctc cgc cag ggc gag gcc cga cgc ctc cgg tgc atg gag      960
Arg Lys Asp Leu Arg Gln Gly Glu Ala Arg Arg Leu Arg Cys Met Glu
305                 310                 315                 320 gag aag gag atg ttc gag ctg cag tgc ctg gca cta cgt aag gac tcc     1008
Glu Lys Glu Met Phe Glu Leu Gln Cys Leu Ala Leu Arg Lys Asp Ser
                325                 330                 335 aag atg tac aag gac cgc atc gag gcc atc ctg ctg cag atg gag gag     1056
Lys Met Tyr Lys Asp Arg Ile Glu Ala Ile Leu Leu Gln Met Glu Glu
            340                 345                 350 gtc gcc att gag cgg gac cag agc aca caa atg gag ggg ctg tga         1101
Val Ala Ile Glu Arg Asp Gln Ser Thr Gln Met Glu Gly Leu *
                355                 360                 365

<210> SEQ ID NO 2
<211> LENGTH: 366
<212> TYPE: PRT
<213> ORGANISM: Homo sapiens

<400> SEQUENCE: 2

Met Ser Asp Tyr Glu Asn Asp Asp Glu Cys Trp Asn Val Leu Glu Gly
1               5                   10                  15

Phe Arg Val Thr Leu Thr Ser Val Ile Asp Pro Ser Arg Ile Thr Pro
            20                  25                  30

Tyr Leu Arg Gln Cys Lys Val Leu Asn Pro Asp Asp Glu Glu Gln Val
        35                  40                  45

Leu Ser Asp Pro Asn Leu Val Ile Arg Lys Arg Lys Val Gly Val Leu
    50                  55                  60

Leu Asp Ile Leu Gln Arg Thr Gly His Lys Gly Tyr Val Ala Phe Leu
65                  70                  75                  80

Glu Ser Leu Glu Leu Tyr Tyr Pro Gln Leu Tyr Lys Lys Val Thr Gly
                85                  90                  95

Lys Glu Pro Ala Arg Val Phe Ser Met Ile Ile Asp Ala Ser Gly Glu
            100                 105                 110

Ser Gly Leu Thr Gln Leu Leu Met Thr Glu Val Met Lys Leu Gln Lys
        115                 120                 125

Lys Val Gln Asp Leu Thr Ala Leu Leu Ser Ser Lys Asp Asp Phe Ile
    130                 135                 140

Lys Glu Leu Arg Val Lys Asp Ser Leu Leu Arg Lys His Gln Glu Arg
145                 150                 155                 160

Val Gln Arg Leu Lys Glu Glu Cys Glu Ala Gly Ser Arg Glu Leu Lys
                165                 170                 175

Arg Cys Lys Glu Glu Asn Tyr Asp Leu Ala Met Arg Leu Ala His Gln
            180                 185                 190

Ser Glu Glu Lys Gly Ala Ala Leu Met Arg Asn Arg Asp Leu Gln Leu
        195                 200                 205

Glu Ile Asp Gln Leu Lys His Ser Leu Met Lys Ala Glu Asp Asp Cys
    210                 215                 220

Lys Val Glu Arg Lys His Thr Leu Lys Leu Arg His Ala Met Glu Gln
```

```
                225                 230                 235                 240
Arg Pro Ser Gln Glu Leu Leu Trp Glu Leu Gln Gln Glu Lys Ala Leu
                    245                 250                 255
Leu Gln Ala Arg Val Gln Glu Leu Glu Ala Ser Val Gln Glu Gly Lys
                260                 265                 270
Leu Asp Arg Ser Ser Pro Tyr Ile Gln Val Leu Glu Glu Asp Trp Arg
            275                 280                 285
Gln Ala Leu Arg Asp His Gln Glu Gln Ala Asn Thr Ile Phe Ser Leu
        290                 295                 300
Arg Lys Asp Leu Arg Gln Gly Glu Ala Arg Arg Leu Arg Cys Met Glu
305                 310                 315                 320
Glu Lys Glu Met Phe Glu Leu Gln Cys Leu Ala Leu Arg Lys Asp Ser
                325                 330                 335
Lys Met Tyr Lys Asp Arg Ile Glu Ala Ile Leu Leu Gln Met Glu Glu
                340                 345                 350
Val Ala Ile Glu Arg Asp Gln Ser Thr Gln Met Glu Gly Leu
                355                 360                 365

<210> SEQ ID NO 3
<211> LENGTH: 216
<212> TYPE: DNA
<213> ORGANISM: Homo sapiens
<220> FEATURE:
<221> NAME/KEY: CDS
<222> LOCATION: (1)...(216)

<400> SEQUENCE: 3 aac gtc ctg gag ggc ttc cgg gtg acg ctc acc tcg gtc atc gac ccc      48
Asn Val Leu Glu Gly Phe Arg Val Thr Leu Thr Ser Val Ile Asp Pro
  1               5                  10                  15 tca cgc atc aca cct tac ctg cgg cag tgc aag gtc ctg aac cct gat      96
Ser Arg Ile Thr Pro Tyr Leu Arg Gln Cys Lys Val Leu Asn Pro Asp
                 20                  25                  30 gat gag gag cag gtg ctc agc gac ccc aac ctg gtc atc cgc aaa cgg     144
Asp Glu Glu Gln Val Leu Ser Asp Pro Asn Leu Val Ile Arg Lys Arg
             35                  40                  45 aaa gtg ggt gtg ctc ctg gac atc ctg cag cgg acc ggc cac aag ggc     192
Lys Val Gly Val Leu Leu Asp Ile Leu Gln Arg Thr Gly His Lys Gly
         50                  55                  60 tac gtg gcc ttc ctc gag agc ctg                                     216
Tyr Val Ala Phe Leu Glu Ser Leu
 65              70

<210> SEQ ID NO 4
<211> LENGTH: 72
<212> TYPE: PRT
<213> ORGANISM: Homo sapiens

<400> SEQUENCE: 4

Asn Val Leu Glu Gly Phe Arg Val Thr Leu Thr Ser Val Ile Asp Pro
  1               5                  10                  15

Ser Arg Ile Thr Pro Tyr Leu Arg Gln Cys Lys Val Leu Asn Pro Asp
                 20                  25                  30

Asp Glu Glu Gln Val Leu Ser Asp Pro Asn Leu Val Ile Arg Lys Arg
             35                  40                  45

Lys Val Gly Val Leu Leu Asp Ile Leu Gln Arg Thr Gly His Lys Gly
         50                  55                  60

Tyr Val Ala Phe Leu Glu Ser Leu
 65                  70
```

```
<210> SEQ ID NO 5
<211> LENGTH: 432
<212> TYPE: DNA
<213> ORGANISM: Homo sapiens
<220> FEATURE:
<221> NAME/KEY: CDS
<222> LOCATION: (1)...(432)

<400> SEQUENCE: 5 ctg cgc aag cac cag gag cgt gtg cag agg ctc aag gag gag tgc gag        48
Leu Arg Lys His Gln Glu Arg Val Gln Arg Leu Lys Glu Glu Cys Glu
 1               5                  10                  15 gcc ggc agc cgc gag ctc aag cgc tgc aag gag gag aac tac gac ctg        96
Ala Gly Ser Arg Glu Leu Lys Arg Cys Lys Glu Glu Asn Tyr Asp Leu
            20                  25                  30 gcc atg cgc ctg gcg cac cag agt gag gag aag ggc gcc gcg ctc atg       144
Ala Met Arg Leu Ala His Gln Ser Glu Glu Lys Gly Ala Ala Leu Met
        35                  40                  45 cgg aac cgt gac ctg cag ctg gag att gac cag ctc aag cac agc ctc       192
Arg Asn Arg Asp Leu Gln Leu Glu Ile Asp Gln Leu Lys His Ser Leu
    50                  55                  60 atg aag gcc gag gac gac tgc aag gtg gag cgc aag cac acg ctg aag       240
Met Lys Ala Glu Asp Asp Cys Lys Val Glu Arg Lys His Thr Leu Lys
65                  70                  75                  80 ctc agg cac gcc atg gag cag cgg ccc agc cag gag ctg ctg tgg gag       288
Leu Arg His Ala Met Glu Gln Arg Pro Ser Gln Glu Leu Leu Trp Glu
                85                  90                  95 ctg cag cag gag aag gcc ctg ctc cag gcc cgg gtg cag gag ctg gag       336
Leu Gln Gln Glu Lys Ala Leu Leu Gln Ala Arg Val Gln Glu Leu Glu
            100                 105                 110 gcc tcc gtc cag gag ggg aag ctg gac agg agc agc ccc tac atc cag       384
Ala Ser Val Gln Glu Gly Lys Leu Asp Arg Ser Ser Pro Tyr Ile Gln
        115                 120                 125 gta ctg gag gag gac tgg cgg cag gcg ctg cgg gac cac cag gag cag       432
Val Leu Glu Glu Asp Trp Arg Gln Ala Leu Arg Asp His Gln Glu Gln
    130                 135                 140

<210> SEQ ID NO 6
<211> LENGTH: 144
<212> TYPE: PRT
<213> ORGANISM: Homo sapiens

<400> SEQUENCE: 6

Leu Arg Lys His Gln Glu Arg Val Gln Arg Leu Lys Glu Glu Cys Glu
 1               5                  10                  15

Ala Gly Ser Arg Glu Leu Lys Arg Cys Lys Glu Glu Asn Tyr Asp Leu
            20                  25                  30

Ala Met Arg Leu Ala His Gln Ser Glu Glu Lys Gly Ala Ala Leu Met
        35                  40                  45

Arg Asn Arg Asp Leu Gln Leu Glu Ile Asp Gln Leu Lys His Ser Leu
    50                  55                  60

Met Lys Ala Glu Asp Asp Cys Lys Val Glu Arg Lys His Thr Leu Lys
65                  70                  75                  80

Leu Arg His Ala Met Glu Gln Arg Pro Ser Gln Glu Leu Leu Trp Glu
                85                  90                  95

Leu Gln Gln Glu Lys Ala Leu Leu Gln Ala Arg Val Gln Glu Leu Glu
            100                 105                 110

Ala Ser Val Gln Glu Gly Lys Leu Asp Arg Ser Ser Pro Tyr Ile Gln
        115                 120                 125
```

```
Val Leu Glu Glu Asp Trp Arg Gln Ala Leu Arg Asp His Gln Glu Gln
    130                 135                 140
```

```
<210> SEQ ID NO 7
<211> LENGTH: 3744
<212> TYPE: DNA
<213> ORGANISM: Homo sapiens
<220> FEATURE:
<221> NAME/KEY: CDS
<222> LOCATION: (1)...(3744)

<400> SEQUENCE: 7
```

```
atg gat gac tac atg gag acg ctg aag gat gaa gag gac gcc ttg tgg      48
Met Asp Asp Tyr Met Glu Thr Leu Lys Asp Glu Glu Asp Ala Leu Trp
  1               5                  10                  15 gag aat gtg gag tgt aac cgg cac atg ctc agc cgc tat atc aac cct      96
Glu Asn Val Glu Cys Asn Arg His Met Leu Ser Arg Tyr Ile Asn Pro
             20                  25                  30 gcc aag ctc acg ccc tac ctg cgt cag tgt aag gtc att gat gag cag     144
Ala Lys Leu Thr Pro Tyr Leu Arg Gln Cys Lys Val Ile Asp Glu Gln
         35                  40                  45 gat gaa gat gaa gtg ctt aat gcc cct atg ctg cca tcc aag atc aac     192
Asp Glu Asp Glu Val Leu Asn Ala Pro Met Leu Pro Ser Lys Ile Asn
 50                  55                  60 cga gca ggc cgg ctg ttg gac att cta cat acc aag ggg caa agg ggc     240
Arg Ala Gly Arg Leu Leu Asp Ile Leu His Thr Lys Gly Gln Arg Gly
 65                  70                  75                  80 tat gtg gtc ttc ttg gag agc cta gaa ttt tat tac cca gaa ctg tac     288
Tyr Val Val Phe Leu Glu Ser Leu Glu Phe Tyr Tyr Pro Glu Leu Tyr
                 85                  90                  95 aaa ctg gtg act ggg aaa gag ccc act cgg aga ttc tcc acc att gtg     336
Lys Leu Val Thr Gly Lys Glu Pro Thr Arg Arg Phe Ser Thr Ile Val
            100                 105                 110 gtg gag gaa ggc cac gag ggc ctc acg cac ttc ctg atg aac gag gtc     384
Val Glu Glu Gly His Glu Gly Leu Thr His Phe Leu Met Asn Glu Val
        115                 120                 125 atc aag ctg cag cag cag atg aag gcc aag gac ctg caa cgc tgc gag     432
Ile Lys Leu Gln Gln Gln Met Lys Ala Lys Asp Leu Gln Arg Cys Glu
    130                 135                 140 ctg ctg gcc agg ttg cgg cag ctg gag gat gag aag aag cag atg acg     480
Leu Leu Ala Arg Leu Arg Gln Leu Glu Asp Glu Lys Lys Gln Met Thr
145                 150                 155                 160 ctg acg cgc gtg gag ctg cta acc ttc cag gag cgg tac tac aag atg     528
Leu Thr Arg Val Glu Leu Leu Thr Phe Gln Glu Arg Tyr Tyr Lys Met
                165                 170                 175 aag gaa gag cgg gac agc tac aat gac gag ctg gtc aag gtg aag gac     576
Lys Glu Glu Arg Asp Ser Tyr Asn Asp Glu Leu Val Lys Val Lys Asp
            180                 185                 190 gac aac tac aac tta gcc atg cgc tac gca cag ctc agt gag gag aag     624
Asp Asn Tyr Asn Leu Ala Met Arg Tyr Ala Gln Leu Ser Glu Glu Lys
        195                 200                 205 aac atg gcg gtc atg agg agc cga gac ctc caa ctc gag atc gat cag     672
Asn Met Ala Val Met Arg Ser Arg Asp Leu Gln Leu Glu Ile Asp Gln
    210                 215                 220 cta aag cac cgg ttg aat aag atg gag gag gaa tgt aag ctg gag aga     720
Leu Lys His Arg Leu Asn Lys Met Glu Glu Glu Cys Lys Leu Glu Arg
225                 230                 235                 240 aat cag tct cta aaa ctg aag aat gac att gaa aat cgg ccc aag aag     768
Asn Gln Ser Leu Lys Leu Lys Asn Asp Ile Glu Asn Arg Pro Lys Lys
                245                 250                 255
```

-continued

| | |
|---|---|
| gag cag gtt ctg gaa ctg gag cgg gag aat gaa atg ctg aag acc aaa<br>Glu Gln Val Leu Glu Leu Glu Arg Glu Asn Glu Met Leu Lys Thr Lys<br>260                      265                      270 | 816 |
| aac cag gag ctg cag tcc atc atc cag gcc ggg aag cgc agc ctg cca<br>Asn Gln Glu Leu Gln Ser Ile Ile Gln Ala Gly Lys Arg Ser Leu Pro<br>275                      280                      285 | 864 |
| gac tca gac aag gcc atc ctg gac atc ttg gaa cac gac cgc aag gag<br>Asp Ser Asp Lys Ala Ile Leu Asp Ile Leu Glu His Asp Arg Lys Glu<br>290                      295                      300 | 912 |
| gcc ctg gag gac agg cag gag ctg gtc aac agg atc tac aac ctg cag<br>Ala Leu Glu Asp Arg Gln Glu Leu Val Asn Arg Ile Tyr Asn Leu Gln<br>305                      310                      315                      320 | 960 |
| gag gag gcc cgc cag gca gag gag ctg cga gac aag tac ctg gag gag<br>Glu Glu Ala Arg Gln Ala Glu Glu Leu Arg Asp Lys Tyr Leu Glu Glu<br>325                      330                      335 | 1008 |
| aag gag gac ctg gag ctc aag tgc tcg acc ctg gga aag gac tgt gaa<br>Lys Glu Asp Leu Glu Leu Lys Cys Ser Thr Leu Gly Lys Asp Cys Glu<br>340                      345                      350 | 1056 |
| atg tac aag cac cgc atg aac acg gtc atg ctg cag ctg gag gag gtg<br>Met Tyr Lys His Arg Met Asn Thr Val Met Leu Gln Leu Glu Glu Val<br>355                      360                      365 | 1104 |
| gag cgg gag cgg gac cag gga cag gct gtg gcc ttc cag gga cac tgc<br>Glu Arg Glu Arg Asp Gln Gly Gln Ala Val Ala Phe Gln Gly His Cys<br>370                      375                      380 | 1152 |
| atc aaa gct ctc aac aca gag cct gcc act agc aag ggt cgg acc atc<br>Ile Lys Ala Leu Asn Thr Glu Pro Ala Thr Ser Lys Gly Arg Thr Ile<br>385                      390                      395                      400 | 1200 |
| ggc tct gtg atc gcg tta atg aag aag gcc ttc cac tcc cga gat gaa<br>Gly Ser Val Ile Ala Leu Met Lys Lys Ala Phe His Ser Arg Asp Glu<br>405                      410                      415 | 1248 |
| gct cag aca cag tac tcg cag tgc tta atc gaa aag gac aag tac agg<br>Ala Gln Thr Gln Tyr Ser Gln Cys Leu Ile Glu Lys Asp Lys Tyr Arg<br>420                      425                      430 | 1296 |
| aag cag atc cgc gag ctg gag gag aag aac gac gag atg agg atc gag<br>Lys Gln Ile Arg Glu Leu Glu Glu Lys Asn Asp Glu Met Arg Ile Glu<br>435                      440                      445 | 1344 |
| atg gtg cgg cgg gag gcc tgc atc gtc aac ctg gag agc aag ctg cgg<br>Met Val Arg Arg Glu Ala Cys Ile Val Asn Leu Glu Ser Lys Leu Arg<br>450                      455                      460 | 1392 |
| cgc ctc tcc aag gac agc aac aac ctg gac cag agt ctg ccc agg aac<br>Arg Leu Ser Lys Asp Ser Asn Asn Leu Asp Gln Ser Leu Pro Arg Asn<br>465                      470                      475                      480 | 1440 |
| ctg cca gta acc atc atc tct cag gac ttt ggg gat gcc agc ccc agg<br>Leu Pro Val Thr Ile Ile Ser Gln Asp Phe Gly Asp Ala Ser Pro Arg<br>485                      490                      495 | 1488 |
| acc aat ggt caa gaa gct gac gat tct tcc acc tcg gag gag tca cct<br>Thr Asn Gly Gln Glu Ala Asp Asp Ser Ser Thr Ser Glu Glu Ser Pro<br>500                      505                      510 | 1536 |
| gaa gac agc aag tac ttc ctg ccc tac cat ccg ccc cag cgc agg atg<br>Glu Asp Ser Lys Tyr Phe Leu Pro Tyr His Pro Pro Gln Arg Arg Met<br>515                      520                      525 | 1584 |
| aac ctg aag ggc atc cag ctg cag aga gcc aaa tcc ccc atc agc ctg<br>Asn Leu Lys Gly Ile Gln Leu Gln Arg Ala Lys Ser Pro Ile Ser Leu<br>530                      535                      540 | 1632 |
| aag cga aca tca gat ttt caa gcc aag ggg cac gag gaa gaa ggc acg<br>Lys Arg Thr Ser Asp Phe Gln Ala Lys Gly His Glu Glu Glu Gly Thr<br>545                      550                      555                      560 | 1680 |
| gac gcc agc cct agc tcc tgc gga tct ctg ccc atc acc aac tcc ttc<br>Asp Ala Ser Pro Ser Ser Cys Gly Ser Leu Pro Ile Thr Asn Ser Phe<br>565                      570                      575 | 1728 |

```
acc aag atg ccc ccc cgg agc cgc agc agc atc atg tca atc acc gcc    1776
Thr Lys Met Pro Pro Arg Ser Arg Ser Ser Ile Met Ser Ile Thr Ala
            580                 585                 590 gag ccc ccg gga aac gac tcc atc gtc aga cgc tac aag gag gac gcg    1824
Glu Pro Pro Gly Asn Asp Ser Ile Val Arg Arg Tyr Lys Glu Asp Ala
        595                 600                 605 ccc cat cgc agc aca gtc gaa gaa gac aat gac agc ggc ggg ttt gac    1872
Pro His Arg Ser Thr Val Glu Glu Asp Asn Asp Ser Gly Gly Phe Asp
    610                 615                 620 gcc tta gat ctg gat gag ctg gca gca ggg gag act gtg gct cag agt    1920
Ala Leu Asp Leu Asp Glu Leu Ala Ala Gly Glu Thr Val Ala Gln Ser
625                 630                 635                 640 cct cca ggt gtg ccc tgc cag ccc cct ctc ttc cag ggc tcc ccc agc    1968
Pro Pro Gly Val Pro Cys Gln Pro Pro Leu Phe Gln Gly Ser Pro Ser
                645                 650                 655 ctt tgc cag cta agg ctg cca acc gat gaa acg aaa gat gag tgg tcc    2016
Leu Cys Gln Leu Arg Leu Pro Thr Asp Glu Thr Lys Asp Glu Trp Ser
            660                 665                 670 tcc tta atg ggg aag cat cag cgc tac caa gtg tta aag aga gat gac    2064
Ser Leu Met Gly Lys His Gln Arg Tyr Gln Val Leu Lys Arg Asp Asp
        675                 680                 685 agt cac gaa cgc tac tcc ttc gga ccc tcc tcc atc cac tcc tcc tcc    2112
Ser His Glu Arg Tyr Ser Phe Gly Pro Ser Ser Ile His Ser Ser Ser
    690                 695                 700 tcc tcc cac caa tcc gag ggc ctg gat gcc tac gac ctg gag cag gtc    2160
Ser Ser His Gln Ser Glu Gly Leu Asp Ala Tyr Asp Leu Glu Gln Val
705                 710                 715                 720 aac ctc atg ttc agg aag ttc tct ctg gaa aga ccc ttc cgg cct tcg    2208
Asn Leu Met Phe Arg Lys Phe Ser Leu Glu Arg Pro Phe Arg Pro Ser
                725                 730                 735 gtc acc tct gtg ggg cac gtg cgg ggc cca ggg ccc tcg gtg cag cac    2256
Val Thr Ser Val Gly His Val Arg Gly Pro Gly Pro Ser Val Gln His
            740                 745                 750 acg acg ctg aat ggc gac agc ctc acc tcc cag ctc acc ctg ctg ggg    2304
Thr Thr Leu Asn Gly Asp Ser Leu Thr Ser Gln Leu Thr Leu Leu Gly
        755                 760                 765 ggc aac gcg cga ggg agc ttc gtg cac tcg gtc aag cct ggc tct ctg    2352
Gly Asn Ala Arg Gly Ser Phe Val His Ser Val Lys Pro Gly Ser Leu
    770                 775                 780 gcc gag aaa gcc ggc ctc cgt gag ggc cac cag ctg ctg cta gaa        2400
Ala Glu Lys Ala Gly Leu Arg Glu Gly His Gln Leu Leu Leu Leu Glu
785                 790                 795                 800 ggc tgc atc cga ggc gag agg cag agt gtc ccg ttg gac aca tgc acc    2448
Gly Cys Ile Arg Gly Glu Arg Gln Ser Val Pro Leu Asp Thr Cys Thr
                805                 810                 815 aaa gag gaa gcc cac tgg acc atc cag agg tgc agc ggc ccc gtc acg    2496
Lys Glu Glu Ala His Trp Thr Ile Gln Arg Cys Ser Gly Pro Val Thr
            820                 825                 830 ctg cac tac aag gtc aac cac gaa gcc cag cag aaa atc cgt ggg cct    2544
Leu His Tyr Lys Val Asn His Glu Ala Gln Gln Lys Ile Arg Gly Pro
        835                 840                 845 gca gaa tat gat gtg ggc agc acc tcc aaa gcc cgg agc tgc gca gca    2592
Ala Glu Tyr Asp Val Gly Ser Thr Ser Lys Ala Arg Ser Cys Ala Ala
    850                 855                 860 gca cag ccc tgc aag tct gga att cca ggg aaa gaa agt tca ttc cgg    2640
Ala Gln Pro Cys Lys Ser Gly Ile Pro Gly Lys Glu Ser Ser Phe Arg
865                 870                 875                 880 cag ggg tac cgg aag ctg gtg aag gac atg gag gac ggc ctg atc aca    2688
Gln Gly Tyr Arg Lys Leu Val Lys Asp Met Glu Asp Gly Leu Ile Thr
```

-continued

|  |  |  |
|---|---|---|
| 885 | 890 | 895 |

| | |
|---|---|
| tcg ggg gac tcg ttc tac atc cgg ctg aac ctg aac atc tcc agc cag<br>Ser Gly Asp Ser Phe Tyr Ile Arg Leu Asn Leu Asn Ile Ser Ser Gln<br>900                        905                      910 | 2736 |
| ctg gac gcc tgc acc atg tcc ctg aag tgt gac gat gtt gtg cac gtc<br>Leu Asp Ala Cys Thr Met Ser Leu Lys Cys Asp Asp Val Val His Val<br>        915                      920                      925 | 2784 |
| cgt gac acc atg tac cag gac agg cac gag tgg ctg tgc gcg cgg gtc<br>Arg Asp Thr Met Tyr Gln Asp Arg His Glu Trp Leu Cys Ala Arg Val<br>930                        935                      940 | 2832 |
| gac cct ttc aca gac cat gac ctg gat atg ggc acc ata ccc agc tac<br>Asp Pro Phe Thr Asp His Asp Leu Asp Met Gly Thr Ile Pro Ser Tyr<br>945                        950                      955                      960 | 2880 |
| agc cga gcc cag cag ctc ctc ctg gtg aaa ctg cag cgc ctg atg cac<br>Ser Arg Ala Gln Gln Leu Leu Leu Val Lys Leu Gln Arg Leu Met His<br>        965                      970                      975 | 2928 |
| cga ggc agc cgg gag gag gta gac ggc acc cac cac acc ctg cgg gca<br>Arg Gly Ser Arg Glu Glu Val Asp Gly Thr His His Thr Leu Arg Ala<br>980                        985                      990 | 2976 |
| ctc cgg ttc gtc agc agg tcc gag aac aag tat aag cgg atg aac agc<br>Leu Arg Phe Val Ser Arg Ser Glu Asn Lys Tyr Lys Arg Met Asn Ser<br>995                        1000                    1005 | 3024 |
| aat gag cgg gtc cgc atc atc tcg ggg agt ccg cta ggg agc ctg gcc<br>Asn Glu Arg Val Arg Ile Ile Ser Gly Ser Pro Leu Gly Ser Leu Ala<br>        1010                      1015                    1020 | 3072 |
| cgg tcc tcg ctg gac gcc acc aag ctc ttg act gag aag cag gaa gag<br>Arg Ser Ser Leu Asp Ala Thr Lys Leu Leu Thr Glu Lys Gln Glu Glu<br>1025                      1030                    1035                    1040 | 3120 |
| ctg gac cct gag agc gag ctg ggc aag aac ctc agc ctc atc ccc tac<br>Leu Asp Pro Glu Ser Glu Leu Gly Lys Asn Leu Ser Leu Ile Pro Tyr<br>        1045                      1050                    1055 | 3168 |
| agc ctg gta cgc gcc ttc tac tgc gag cgc cgc cgg ccc gtg ctc ttc<br>Ser Leu Val Arg Ala Phe Tyr Cys Glu Arg Arg Arg Pro Val Leu Phe<br>1060                      1065                    1070 | 3216 |
| aca ccc acc gtg ctg gcc aag acg ctg gtg cag agg ctg ctc aac tcg<br>Thr Pro Thr Val Leu Ala Lys Thr Leu Val Gln Arg Leu Leu Asn Ser<br>        1075                      1080                    1085 | 3264 |
| gga ggt gcc atg gag ttc acc atc tgc aag tca gat atc gtc aca aga<br>Gly Gly Ala Met Glu Phe Thr Ile Cys Lys Ser Asp Ile Val Thr Arg<br>1090                      1095                    1100 | 3312 |
| gat gag ttc ctc aga agg cag aag acg gag acc atc atc tac tcc cga<br>Asp Glu Phe Leu Arg Arg Gln Lys Thr Glu Thr Ile Ile Tyr Ser Arg<br>1105                      1110                    1115                    1120 | 3360 |
| gag aag aac ccc aac gcg ttc gaa tgc atc gcc cct gcc aac att gaa<br>Glu Lys Asn Pro Asn Ala Phe Glu Cys Ile Ala Pro Ala Asn Ile Glu<br>        1125                      1130                    1135 | 3408 |
| gct gtg gcc gcc aag aac aag cac tgc ctg ctg gag gct ggg atc ggc<br>Ala Val Ala Ala Lys Asn Lys His Cys Leu Leu Glu Ala Gly Ile Gly<br>1140                      1145                    1150 | 3456 |
| tgc aca aga gac ttg atc aag tcc aac atc tac ccc atc gtg ctc ttc<br>Cys Thr Arg Asp Leu Ile Lys Ser Asn Ile Tyr Pro Ile Val Leu Phe<br>        1155                      1160                    1165 | 3504 |
| atc cgg gtg tgt gag aag aac atc aag agg ttc aga aag ctg ctg ccc<br>Ile Arg Val Cys Glu Lys Asn Ile Lys Arg Phe Arg Lys Leu Leu Pro<br>1170                      1175                    1180 | 3552 |
| cgg cct gag acg gag gag gag ttc ctg cgc gtg tgc cgg ctg aag gag<br>Arg Pro Glu Thr Glu Glu Glu Phe Leu Arg Val Cys Arg Leu Lys Glu<br>1185                      1190                    1195                    1200 | 3600 |
| aag gag ctg gag gcc ctg ccg tgc ctg tac gcc acg gtg gaa cct gac<br>Lys Glu Leu Glu Ala Leu Pro Cys Leu Tyr Ala Thr Val Glu Pro Asp | 3648 |

-continued

```
Lys Glu Leu Glu Ala Leu Pro Cys Leu Tyr Ala Thr Val Glu Pro Asp
            1205                1210                1215 atg tgg ggc agc gta gag gag ctg ctc cgc gtt gtc aag gac aag atc      3696
Met Trp Gly Ser Val Glu Glu Leu Leu Arg Val Val Lys Asp Lys Ile
        1220                1225                1230 ggc gag gag cag cgc aag acc atc tgg gtg gac gag gac cag ctg tga      3744
Gly Glu Glu Gln Arg Lys Thr Ile Trp Val Asp Glu Asp Gln Leu *
            1235                1240                1245

<210> SEQ ID NO 8
<211> LENGTH: 1247
<212> TYPE: PRT
<213> ORGANISM: Homo sapiens

<400> SEQUENCE: 8

Met Asp Asp Tyr Met Glu Thr Leu Lys Asp Glu Asp Ala Leu Trp
  1               5                  10                  15

Glu Asn Val Glu Cys Asn Arg His Met Leu Ser Arg Tyr Ile Asn Pro
             20                  25                  30

Ala Lys Leu Thr Pro Tyr Leu Arg Gln Cys Lys Val Ile Asp Glu Gln
         35                  40                  45

Asp Glu Asp Glu Val Leu Asn Ala Pro Met Leu Pro Ser Lys Ile Asn
     50                  55                  60

Arg Ala Gly Arg Leu Leu Asp Ile Leu His Thr Lys Gly Gln Arg Gly
 65                  70                  75                  80

Tyr Val Val Phe Leu Glu Ser Leu Glu Phe Tyr Tyr Pro Glu Leu Tyr
                 85                  90                  95

Lys Leu Val Thr Gly Lys Glu Pro Thr Arg Arg Phe Ser Thr Ile Val
            100                 105                 110

Val Glu Glu Gly His Glu Gly Leu Thr His Phe Leu Met Asn Glu Val
        115                 120                 125

Ile Lys Leu Gln Gln Met Lys Ala Lys Asp Leu Gln Arg Cys Glu
    130                 135                 140

Leu Leu Ala Arg Leu Arg Gln Leu Glu Asp Glu Lys Lys Gln Met Thr
145                 150                 155                 160

Leu Thr Arg Val Glu Leu Leu Thr Phe Gln Glu Arg Tyr Tyr Lys Met
                165                 170                 175

Lys Glu Glu Arg Asp Ser Tyr Asn Asp Glu Leu Val Lys Val Lys Asp
            180                 185                 190

Asp Asn Tyr Asn Leu Ala Met Arg Tyr Ala Gln Leu Ser Glu Glu Lys
        195                 200                 205

Asn Met Ala Val Met Arg Ser Arg Asp Leu Gln Leu Glu Ile Asp Gln
    210                 215                 220

Leu Lys His Arg Leu Asn Lys Met Glu Glu Glu Cys Lys Leu Glu Arg
225                 230                 235                 240

Asn Gln Ser Leu Lys Leu Lys Asn Asp Ile Glu Asn Arg Pro Lys Lys
                245                 250                 255

Glu Gln Val Leu Glu Leu Glu Arg Glu Asn Glu Met Leu Lys Thr Lys
            260                 265                 270

Asn Gln Glu Leu Gln Ser Ile Ile Gln Ala Gly Lys Arg Ser Leu Pro
        275                 280                 285

Asp Ser Asp Lys Ala Ile Leu Asp Ile Leu Glu His Asp Arg Lys Glu
    290                 295                 300

Ala Leu Glu Asp Arg Gln Glu Leu Val Asn Arg Ile Tyr Asn Leu Gln
305                 310                 315                 320
```

-continued

```
Glu Glu Ala Arg Gln Ala Glu Leu Arg Asp Lys Tyr Leu Glu Glu
                325                 330                 335

Lys Glu Asp Leu Glu Leu Lys Cys Ser Thr Leu Gly Lys Asp Cys Glu
                340                 345                 350

Met Tyr Lys His Arg Met Asn Thr Val Met Leu Gln Leu Glu Glu Val
                355                 360                 365

Glu Arg Glu Arg Asp Gln Gly Gln Ala Val Ala Phe Gln Gly His Cys
            370                 375                 380

Ile Lys Ala Leu Asn Thr Glu Pro Ala Thr Ser Lys Gly Arg Thr Ile
385                 390                 395                 400

Gly Ser Val Ile Ala Leu Met Lys Lys Ala Phe His Ser Arg Asp Glu
                405                 410                 415

Ala Gln Thr Gln Tyr Ser Gln Cys Leu Ile Glu Lys Asp Lys Tyr Arg
            420                 425                 430

Lys Gln Ile Arg Glu Leu Glu Glu Lys Asn Asp Glu Met Arg Ile Glu
                435                 440                 445

Met Val Arg Arg Glu Ala Cys Ile Val Asn Leu Glu Ser Lys Leu Arg
    450                 455                 460

Arg Leu Ser Lys Asp Ser Asn Asn Leu Asp Gln Ser Leu Pro Arg Asn
465                 470                 475                 480

Leu Pro Val Thr Ile Ile Ser Gln Asp Phe Gly Asp Ala Ser Pro Arg
                485                 490                 495

Thr Asn Gly Gln Glu Ala Asp Asp Ser Ser Thr Ser Glu Glu Ser Pro
            500                 505                 510

Glu Asp Ser Lys Tyr Phe Leu Pro Tyr His Pro Pro Gln Arg Arg Met
            515                 520                 525

Asn Leu Lys Gly Ile Gln Leu Gln Arg Ala Lys Ser Pro Ile Ser Leu
    530                 535                 540

Lys Arg Thr Ser Asp Phe Gln Ala Lys Gly His Glu Glu Glu Gly Thr
545                 550                 555                 560

Asp Ala Ser Pro Ser Ser Cys Gly Ser Leu Pro Ile Thr Asn Ser Phe
                565                 570                 575

Thr Lys Met Pro Pro Arg Ser Arg Ser Ser Ile Met Ser Ile Thr Ala
            580                 585                 590

Glu Pro Pro Gly Asn Asp Ser Ile Val Arg Arg Tyr Lys Glu Asp Ala
            595                 600                 605

Pro His Arg Ser Thr Val Glu Glu Asp Asn Asp Ser Gly Gly Phe Asp
    610                 615                 620

Ala Leu Asp Leu Asp Glu Leu Ala Ala Gly Glu Thr Val Ala Gln Ser
625                 630                 635                 640

Pro Pro Gly Val Pro Cys Gln Pro Pro Leu Phe Gln Gly Ser Pro Ser
                645                 650                 655

Leu Cys Gln Leu Arg Leu Pro Thr Asp Glu Thr Lys Asp Glu Trp Ser
            660                 665                 670

Ser Leu Met Gly Lys His Gln Arg Tyr Gln Val Leu Lys Arg Asp Asp
            675                 680                 685

Ser His Glu Arg Tyr Ser Phe Gly Pro Ser Ser His Ser Ser Ser Ser
    690                 695                 700

Ser Ser His Gln Ser Glu Gly Leu Asp Ala Tyr Asp Leu Glu Gln Val
705                 710                 715                 720

Asn Leu Met Phe Arg Lys Phe Ser Leu Glu Arg Pro Phe Arg Pro Ser
                725                 730                 735

Val Thr Ser Val Gly His Val Arg Gly Pro Gly Pro Ser Val Gln His
```

-continued

```
                740                 745                 750
Thr Thr Leu Asn Gly Asp Ser Leu Thr Ser Gln Leu Thr Leu Gly
            755                 760                 765
Gly Asn Ala Arg Gly Ser Phe Val His Ser Val Lys Pro Gly Ser Leu
        770                 775                 780
Ala Glu Lys Ala Gly Leu Arg Glu Gly His Gln Leu Leu Leu Glu
785                 790                 795                 800
Gly Cys Ile Arg Gly Glu Arg Gln Ser Val Pro Leu Asp Thr Cys Thr
                805                 810                 815
Lys Glu Glu Ala His Trp Thr Ile Gln Arg Cys Ser Gly Pro Val Thr
            820                 825                 830
Leu His Tyr Lys Val Asn His Glu Ala Gln Gln Lys Ile Arg Gly Pro
        835                 840                 845
Ala Glu Tyr Asp Val Gly Ser Thr Ser Lys Ala Arg Ser Cys Ala Ala
        850                 855                 860
Ala Gln Pro Cys Lys Ser Gly Ile Pro Gly Lys Glu Ser Ser Phe Arg
865                 870                 875                 880
Gln Gly Tyr Arg Lys Leu Val Lys Asp Met Glu Asp Gly Leu Ile Thr
                885                 890                 895
Ser Gly Asp Ser Phe Tyr Ile Arg Leu Asn Leu Asn Ile Ser Ser Gln
            900                 905                 910
Leu Asp Ala Cys Thr Met Ser Leu Lys Cys Asp Asp Val Val His Val
        915                 920                 925
Arg Asp Thr Met Tyr Gln Asp Arg His Glu Trp Leu Cys Ala Arg Val
    930                 935                 940
Asp Pro Phe Thr Asp His Asp Leu Asp Met Gly Thr Ile Pro Ser Tyr
945                 950                 955                 960
Ser Arg Ala Gln Gln Leu Leu Leu Val Lys Leu Gln Arg Leu Met His
                965                 970                 975
Arg Gly Ser Arg Glu Glu Val Asp Gly Thr His His Thr Leu Arg Ala
            980                 985                 990
Leu Arg Phe Val Ser Arg Ser Glu Asn Lys Tyr Lys Arg Met Asn Ser
        995                 1000                1005
Asn Glu Arg Val Arg Ile Ile Ser Gly Ser Pro Leu Gly Ser Leu Ala
    1010                1015                1020
Arg Ser Ser Leu Asp Ala Thr Lys Leu Leu Thr Glu Lys Gln Glu Glu
1025                1030                1035                1040
Leu Asp Pro Glu Ser Glu Leu Gly Lys Asn Leu Ser Leu Ile Pro Tyr
                1045                1050                1055
Ser Leu Val Arg Ala Phe Tyr Cys Glu Arg Arg Arg Pro Val Leu Phe
            1060                1065                1070
Thr Pro Thr Val Leu Ala Lys Thr Leu Val Gln Arg Leu Leu Asn Ser
        1075                1080                1085
Gly Gly Ala Met Glu Phe Thr Ile Cys Lys Ser Asp Ile Val Thr Arg
    1090                1095                1100
Asp Glu Phe Leu Arg Arg Gln Lys Thr Glu Thr Ile Ile Tyr Ser Arg
1105                1110                1115                1120
Glu Lys Asn Pro Asn Ala Phe Glu Cys Ile Ala Pro Ala Asn Ile Glu
                1125                1130                1135
Ala Val Ala Ala Lys Asn Lys His Cys Leu Leu Glu Ala Gly Ile Gly
            1140                1145                1150
Cys Thr Arg Asp Leu Ile Lys Ser Asn Ile Tyr Pro Ile Val Leu Phe
        1155                1160                1165
```

```
Ile Arg Val Cys Glu Lys Asn Ile Lys Arg Phe Arg Lys Leu Leu Pro
    1170                1175                1180

Arg Pro Glu Thr Glu Glu Phe Leu Arg Val Cys Arg Leu Lys Glu
1185                1190                1195                1200

Lys Glu Leu Glu Ala Leu Pro Cys Leu Tyr Ala Thr Val Glu Pro Asp
            1205                1210                1215

Met Trp Gly Ser Val Glu Leu Leu Arg Val Val Lys Asp Lys Ile
        1220                1225                1230

Gly Glu Glu Gln Arg Lys Thr Ile Trp Val Asp Glu Asp Gln Leu
    1235                1240                1245

<210> SEQ ID NO 9
<211> LENGTH: 276
<212> TYPE: DNA
<213> ORGANISM: Homo sapiens
<220> FEATURE:
<221> NAME/KEY: CDS
<222> LOCATION: (1)...(276)

<400> SEQUENCE: 9 gag gac gcc ttg tgg gag aat gtg gag tgt aac cgg cac atg ctc agc       48
Glu Asp Ala Leu Trp Glu Asn Val Glu Cys Asn Arg His Met Leu Ser
 1               5                  10                  15 cgc tat atc aac cct gcc aag ctc acg ccc tac ctg cgt cag tgt aag       96
Arg Tyr Ile Asn Pro Ala Lys Leu Thr Pro Tyr Leu Arg Gln Cys Lys
            20                  25                  30 gtc att gat gag cag gat gaa gat gaa gtg ctt aat gcc cct atg ctg      144
Val Ile Asp Glu Gln Asp Glu Asp Glu Val Leu Asn Ala Pro Met Leu
        35                  40                  45 cca tcc aag atc aac cga gca ggc cgg ctg ttg gac att cta cat acc      192
Pro Ser Lys Ile Asn Arg Ala Gly Arg Leu Leu Asp Ile Leu His Thr
    50                  55                  60 aag ggg caa agg ggc tat gtg gtc ttc ttg gag agc cta gaa ttt tat      240
Lys Gly Gln Arg Gly Tyr Val Val Phe Leu Glu Ser Leu Glu Phe Tyr
 65                 70                  75                  80 tac cca gaa ctg tac aaa ctg gtg act ggg aaa gag                      276
Tyr Pro Glu Leu Tyr Lys Leu Val Thr Gly Lys Glu
                85                  90

<210> SEQ ID NO 10
<211> LENGTH: 92
<212> TYPE: PRT
<213> ORGANISM: Homo sapiens

<400> SEQUENCE: 10

Glu Asp Ala Leu Trp Glu Asn Val Glu Cys Asn Arg His Met Leu Ser
 1               5                  10                  15

Arg Tyr Ile Asn Pro Ala Lys Leu Thr Pro Tyr Leu Arg Gln Cys Lys
            20                  25                  30

Val Ile Asp Glu Gln Asp Glu Asp Glu Val Leu Asn Ala Pro Met Leu
        35                  40                  45

Pro Ser Lys Ile Asn Arg Ala Gly Arg Leu Leu Asp Ile Leu His Thr
    50                  55                  60

Lys Gly Gln Arg Gly Tyr Val Val Phe Leu Glu Ser Leu Glu Phe Tyr
 65                 70                  75                  80

Tyr Pro Glu Leu Tyr Lys Leu Val Thr Gly Lys Glu
                85                  90

<210> SEQ ID NO 11
```

<211> LENGTH: 957
<212> TYPE: DNA
<213> ORGANISM: Homo sapiens
<220> FEATURE:
<221> NAME/KEY: CDS
<222> LOCATION: (1)...(957)

<400> SEQUENCE: 11

| | | | | | | | | | | | | | | | | |
|---|---|---|---|---|---|---|---|---|---|---|---|---|---|---|---|---|
| aag | ctg | cag | cag | cag | atg | aag | gcc | aag | gac | ctg | caa | cgc | tgc | gag | ctg | 48 |
| Lys | Leu | Gln | Gln | Gln | Met | Lys | Ala | Lys | Asp | Leu | Gln | Arg | Cys | Glu | Leu | |
| 1 | | | | 5 | | | | | 10 | | | | | 15 | | |
| ctg | gcc | agg | ttg | cgg | cag | ctg | gag | gat | gag | aag | aag | cag | atg | acg | ctg | 96 |
| Leu | Ala | Arg | Leu | Arg | Gln | Leu | Glu | Asp | Glu | Lys | Lys | Gln | Met | Thr | Leu | |
| | | | 20 | | | | | 25 | | | | | 30 | | | |
| acg | cgc | gtg | gag | ctg | cta | acc | ttc | cag | gag | cgg | tac | tac | aag | atg | aag | 144 |
| Thr | Arg | Val | Glu | Leu | Leu | Thr | Phe | Gln | Glu | Arg | Tyr | Tyr | Lys | Met | Lys | |
| | | | 35 | | | | | 40 | | | | | 45 | | | |
| gaa | gag | cgg | gac | agc | tac | aat | gac | gag | ctg | gtc | aag | gtg | aag | gac | gac | 192 |
| Glu | Glu | Arg | Asp | Ser | Tyr | Asn | Asp | Glu | Leu | Val | Lys | Val | Lys | Asp | Asp | |
| | | 50 | | | | | 55 | | | | | 60 | | | | |
| aac | tac | aac | tta | gcc | atg | cgc | tac | gca | cag | ctc | agt | gag | gag | aag | aac | 240 |
| Asn | Tyr | Asn | Leu | Ala | Met | Arg | Tyr | Ala | Gln | Leu | Ser | Glu | Glu | Lys | Asn | |
| 65 | | | | | 70 | | | | | 75 | | | | | 80 | |
| atg | gcg | gtc | atg | agg | agc | cga | gac | ctc | caa | ctc | gag | atc | gat | cag | cta | 288 |
| Met | Ala | Val | Met | Arg | Ser | Arg | Asp | Leu | Gln | Leu | Glu | Ile | Asp | Gln | Leu | |
| | | | | 85 | | | | | 90 | | | | | 95 | | |
| aag | cac | cgg | ttg | aat | aag | atg | gag | gag | gaa | tgt | aag | ctg | gag | aga | aat | 336 |
| Lys | His | Arg | Leu | Asn | Lys | Met | Glu | Glu | Glu | Cys | Lys | Leu | Glu | Arg | Asn | |
| | | | 100 | | | | | 105 | | | | | 110 | | | |
| cag | tct | cta | aaa | ctg | aag | aat | gac | att | gaa | aat | cgg | ccc | aag | aag | gag | 384 |
| Gln | Ser | Leu | Lys | Leu | Lys | Asn | Asp | Ile | Glu | Asn | Arg | Pro | Lys | Lys | Glu | |
| | | | 115 | | | | | 120 | | | | | 125 | | | |
| cag | gtt | ctg | gaa | ctg | gag | cgg | gag | aat | gaa | atg | ctg | aag | acc | aaa | aac | 432 |
| Gln | Val | Leu | Glu | Leu | Glu | Arg | Glu | Asn | Glu | Met | Leu | Lys | Thr | Lys | Asn | |
| | | 130 | | | | | 135 | | | | | 140 | | | | |
| cag | gag | ctg | cag | tcc | atc | atc | cag | gcc | ggg | aag | cgc | agc | ctg | cca | gac | 480 |
| Gln | Glu | Leu | Gln | Ser | Ile | Ile | Gln | Ala | Gly | Lys | Arg | Ser | Leu | Pro | Asp | |
| 145 | | | | | 150 | | | | | 155 | | | | | 160 | |
| tca | gac | aag | gcc | atc | ctg | gac | atc | ttg | gaa | cac | gac | cgc | aag | gag | gcc | 528 |
| Ser | Asp | Lys | Ala | Ile | Leu | Asp | Ile | Leu | Glu | His | Asp | Arg | Lys | Glu | Ala | |
| | | | | 165 | | | | | 170 | | | | | 175 | | |
| ctg | gag | gac | agg | cag | gag | ctg | gtc | aac | agg | atc | tac | aac | ctg | cag | gag | 576 |
| Leu | Glu | Asp | Arg | Gln | Glu | Leu | Val | Asn | Arg | Ile | Tyr | Asn | Leu | Gln | Glu | |
| | | | 180 | | | | | 185 | | | | | 190 | | | |
| gag | gcc | cgc | cag | gca | gag | gag | ctg | cga | gac | aag | tac | ctg | gag | gag | aag | 624 |
| Glu | Ala | Arg | Gln | Ala | Glu | Glu | Leu | Arg | Asp | Lys | Tyr | Leu | Glu | Glu | Lys | |
| | | | 195 | | | | | 200 | | | | | 205 | | | |
| gag | gac | ctg | gag | ctc | aag | tgc | tcg | acc | ctg | gga | aag | gac | tgt | gaa | atg | 672 |
| Glu | Asp | Leu | Glu | Leu | Lys | Cys | Ser | Thr | Leu | Gly | Lys | Asp | Cys | Glu | Met | |
| | | 210 | | | | | 215 | | | | | 220 | | | | |
| tac | aag | cac | cgc | atg | aac | acg | gtc | atg | ctg | cag | ctg | gag | gag | gtg | gag | 720 |
| Tyr | Lys | His | Arg | Met | Asn | Thr | Val | Met | Leu | Gln | Leu | Glu | Glu | Val | Glu | |
| 225 | | | | | 230 | | | | | 235 | | | | | 240 | |
| cgg | gag | cgg | gac | cag | gga | cag | gct | gtg | gcc | ttc | cag | gga | cac | tgc | atc | 768 |
| Arg | Glu | Arg | Asp | Gln | Gly | Gln | Ala | Val | Ala | Phe | Gln | Gly | His | Cys | Ile | |
| | | | | 245 | | | | | 250 | | | | | 255 | | |
| aaa | gct | ctc | aac | aca | gag | cct | gcc | act | agc | aag | ggt | cgg | acc | atc | ggc | 816 |
| Lys | Ala | Leu | Asn | Thr | Glu | Pro | Ala | Thr | Ser | Lys | Gly | Arg | Thr | Ile | Gly | |
| | | | 260 | | | | | 265 | | | | | 270 | | | |
| tct | gtg | atc | gcg | tta | atg | aag | aag | gcc | ttc | cac | tcc | cga | gat | gaa | gct | 864 |
| Ser | Val | Ile | Ala | Leu | Met | Lys | Lys | Ala | Phe | His | Ser | Arg | Asp | Glu | Ala | |

```
                275                 280                 285
cag aca cag tac tcg cag tgc tta atc gaa aag gac aag tac agg aag    912
Gln Thr Gln Tyr Ser Gln Cys Leu Ile Glu Lys Asp Lys Tyr Arg Lys
    290                 295                 300 cag atc cgc gag ctg gag gag aag aac gac gag atg agg atc gag        957
Gln Ile Arg Glu Leu Glu Glu Lys Asn Asp Glu Met Arg Ile Glu
305                 310                 315
```

<210> SEQ ID NO 12
<211> LENGTH: 319
<212> TYPE: PRT
<213> ORGANISM: Homo sapiens

<400> SEQUENCE: 12

```
Lys Leu Gln Gln Gln Met Lys Ala Lys Asp Leu Gln Arg Cys Glu Leu
 1               5                  10                  15

Leu Ala Arg Leu Arg Gln Leu Glu Asp Glu Lys Lys Gln Met Thr Leu
            20                  25                  30

Thr Arg Val Glu Leu Leu Thr Phe Gln Glu Arg Tyr Tyr Lys Met Lys
        35                  40                  45

Glu Glu Arg Asp Ser Tyr Asn Asp Glu Leu Val Lys Val Lys Asp Asp
    50                  55                  60

Asn Tyr Asn Leu Ala Met Arg Tyr Ala Gln Leu Ser Glu Glu Lys Asn
65                  70                  75                  80

Met Ala Val Met Arg Ser Arg Asp Leu Gln Leu Glu Ile Asp Gln Leu
                85                  90                  95

Lys His Arg Leu Asn Lys Met Glu Glu Glu Cys Lys Leu Glu Arg Asn
            100                 105                 110

Gln Ser Leu Lys Leu Lys Asn Asp Ile Glu Asn Arg Pro Lys Lys Glu
        115                 120                 125

Gln Val Leu Glu Leu Glu Arg Glu Asn Glu Met Leu Lys Thr Lys Asn
    130                 135                 140

Gln Glu Leu Gln Ser Ile Ile Gln Ala Gly Lys Arg Ser Leu Pro Asp
145                 150                 155                 160

Ser Asp Lys Ala Ile Leu Asp Ile Leu Glu His Asp Arg Lys Glu Ala
                165                 170                 175

Leu Glu Asp Arg Gln Glu Leu Val Asn Arg Ile Tyr Asn Leu Gln Glu
            180                 185                 190

Glu Ala Arg Gln Ala Glu Glu Leu Arg Asp Lys Tyr Leu Glu Glu Lys
        195                 200                 205

Glu Asp Leu Glu Leu Lys Cys Ser Thr Leu Gly Lys Asp Cys Glu Met
    210                 215                 220

Tyr Lys His Arg Met Asn Thr Val Met Leu Gln Leu Glu Glu Val Glu
225                 230                 235                 240

Arg Glu Arg Asp Gln Gly Gln Ala Val Ala Phe Gln Gly His Cys Ile
                245                 250                 255

Lys Ala Leu Asn Thr Glu Pro Ala Thr Ser Lys Gly Arg Thr Ile Gly
            260                 265                 270

Ser Val Ile Ala Leu Met Lys Lys Ala Phe His Ser Arg Asp Glu Ala
        275                 280                 285

Gln Thr Gln Tyr Ser Gln Cys Leu Ile Glu Lys Asp Lys Tyr Arg Lys
    290                 295                 300

Gln Ile Arg Glu Leu Glu Glu Lys Asn Asp Glu Met Arg Ile Glu
305                 310                 315
```

<210> SEQ ID NO 13
<211> LENGTH: 339
<212> TYPE: DNA
<213> ORGANISM: Homo sapiens
<220> FEATURE:
<221> NAME/KEY: CDS
<222> LOCATION: (1)...(339)

<400> SEQUENCE: 13

```
aag ttc tct ctg gaa aga ccc ttc cgg cct tcg gtc acc tct gtg ggg       48
Lys Phe Ser Leu Glu Arg Pro Phe Arg Pro Ser Val Thr Ser Val Gly
 1               5                  10                  15 cac gtg cgg ggc cca ggg ccc tcg gtg cag cac acg acg ctg aat ggc       96
His Val Arg Gly Pro Gly Pro Ser Val Gln His Thr Thr Leu Asn Gly
             20                  25                  30 gac agc ctc acc tcc cag ctc acc ctg ctg ggg ggc aac gcg cga ggg      144
Asp Ser Leu Thr Ser Gln Leu Thr Leu Leu Gly Gly Asn Ala Arg Gly
         35                  40                  45 agc ttc gtg cac tcg gtc aag cct ggc tct ctg gcc gag aaa gcc ggc      192
Ser Phe Val His Ser Val Lys Pro Gly Ser Leu Ala Glu Lys Ala Gly
     50                  55                  60 ctc cgt gag ggc cac cag ctg ctg ctg cta gaa ggc tgc atc cga ggc      240
Leu Arg Glu Gly His Gln Leu Leu Leu Leu Glu Gly Cys Ile Arg Gly
 65                  70                  75                  80 gag agg cag agt gtc ccg ttg gac aca tgc acc aaa gag gaa gcc cac      288
Glu Arg Gln Ser Val Pro Leu Asp Thr Cys Thr Lys Glu Glu Ala His
                 85                  90                  95 tgg acc atc cag agg tgc agc ggc ccc gtc acg ctg cac tac aag gtc      336
Trp Thr Ile Gln Arg Cys Ser Gly Pro Val Thr Leu His Tyr Lys Val
            100                 105                 110 aac                                                                  339
Asn
```

<210> SEQ ID NO 14
<211> LENGTH: 113
<212> TYPE: PRT
<213> ORGANISM: Homo sapiens

<400> SEQUENCE: 14

```
Lys Phe Ser Leu Glu Arg Pro Phe Arg Pro Ser Val Thr Ser Val Gly
 1               5                  10                  15

His Val Arg Gly Pro Gly Pro Ser Val Gln His Thr Thr Leu Asn Gly
             20                  25                  30

Asp Ser Leu Thr Ser Gln Leu Thr Leu Leu Gly Gly Asn Ala Arg Gly
         35                  40                  45

Ser Phe Val His Ser Val Lys Pro Gly Ser Leu Ala Glu Lys Ala Gly
     50                  55                  60

Leu Arg Glu Gly His Gln Leu Leu Leu Leu Glu Gly Cys Ile Arg Gly
 65                  70                  75                  80

Glu Arg Gln Ser Val Pro Leu Asp Thr Cys Thr Lys Glu Glu Ala His
                 85                  90                  95

Trp Thr Ile Gln Arg Cys Ser Gly Pro Val Thr Leu His Tyr Lys Val
            100                 105                 110

Asn
```

<210> SEQ ID NO 15
<211> LENGTH: 417
<212> TYPE: DNA
<213> ORGANISM: Homo sapiens
<220> FEATURE:
<221> NAME/KEY: CDS
<220> FEATURE:
<221> NAME/KEY: misc_feature
<222> LOCATION: 416, 417
<223> OTHER INFORMATION: n = A,T,C or G

<400> SEQUENCE: 15

```
atg ggg gaa ctg tgc cgc agg gac tcc gca ctc acg gca ctg gac gag     48
Met Gly Glu Leu Cys Arg Arg Asp Ser Ala Leu Thr Ala Leu Asp Glu
 1               5                  10                  15 gag aca ctg tgg gag atg atg gag agc cac cgc cac agg atc gta cgc     96
Glu Thr Leu Trp Glu Met Met Glu Ser His Arg His Arg Ile Val Arg
             20                  25                  30 tgc atc tgc ccc agc cgc ctc acc ccc tac ctg cgc cag gcc aag gtg    144
Cys Ile Cys Pro Ser Arg Leu Thr Pro Tyr Leu Arg Gln Ala Lys Val
         35                  40                  45 ctg tgc cag ctg gac gag gag gag gtg ctg cac agc ccc cgg ctc acc    192
Leu Cys Gln Leu Asp Glu Glu Glu Val Leu His Ser Pro Arg Leu Thr
     50                  55                  60 aac agc gcc atg cgg gcc ggg cac ttg ctg gat ttg ctg aag act cga    240
Asn Ser Ala Met Arg Ala Gly His Leu Leu Asp Leu Leu Lys Thr Arg
 65                  70                  75                  80 ggg aag aac ggg gcc atc gcc ttc ctg gag agc ctg aag ttc cac aac    288
Gly Lys Asn Gly Ala Ile Ala Phe Leu Glu Ser Leu Lys Phe His Asn
                 85                  90                  95 cct gac gtc tac acc ctg gtc acc ggg ctg cag cct gat gtt gac ttc    336
Pro Asp Val Tyr Thr Leu Val Thr Gly Leu Gln Pro Asp Val Asp Phe
            100                 105                 110 agt aac ttt agc ggt gag agc tcc gac ttt gac ggt ttg gca ggc act    384
Ser Asn Phe Ser Gly Glu Ser Ser Asp Phe Asp Gly Leu Ala Gly Thr
        115                 120                 125 tct agg aac ctc agg ctc ctg gta acc cca gnn                        417
Ser Arg Asn Leu Arg Leu Leu Val Thr Pro Xaa
    130                 135
```

<210> SEQ ID NO 16
<211> LENGTH: 139
<212> TYPE: PRT
<213> ORGANISM: Homo sapiens
<220> FEATURE:
<221> NAME/KEY: VARIANT
<222> LOCATION: 139
<223> OTHER INFORMATION: Xaa = Any Amino Acid

<400> SEQUENCE: 16

```
Met Gly Glu Leu Cys Arg Arg Asp Ser Ala Leu Thr Ala Leu Asp Glu
 1               5                  10                  15

Glu Thr Leu Trp Glu Met Met Glu Ser His Arg His Arg Ile Val Arg
             20                  25                  30

Cys Ile Cys Pro Ser Arg Leu Thr Pro Tyr Leu Arg Gln Ala Lys Val
         35                  40                  45

Leu Cys Gln Leu Asp Glu Glu Glu Val Leu His Ser Pro Arg Leu Thr
     50                  55                  60

Asn Ser Ala Met Arg Ala Gly His Leu Leu Asp Leu Leu Lys Thr Arg
 65                  70                  75                  80

Gly Lys Asn Gly Ala Ile Ala Phe Leu Glu Ser Leu Lys Phe His Asn
                 85                  90                  95

Pro Asp Val Tyr Thr Leu Val Thr Gly Leu Gln Pro Asp Val Asp Phe
            100                 105                 110

Ser Asn Phe Ser Gly Glu Ser Ser Asp Phe Asp Gly Leu Ala Gly Thr
        115                 120                 125
```

Ser Arg Asn Leu Arg Leu Leu Val Thr Pro Xaa
    130                 135

<210> SEQ ID NO 17
<211> LENGTH: 276
<212> TYPE: DNA
<213> ORGANISM: Homo sapiens
<220> FEATURE:
<221> NAME/KEY: CDS
<222> LOCATION: (1)...(276)

<400> SEQUENCE: 17

```
gag gag aca ctg tgg gag atg atg gag agc cac cgc cac agg atc gta      48
Glu Glu Thr Leu Trp Glu Met Met Glu Ser His Arg His Arg Ile Val
1               5                   10                  15 cgc tgc atc tgc ccc agc cgc ctc acc ccc tac ctg cgc cag gcc aag      96
Arg Cys Ile Cys Pro Ser Arg Leu Thr Pro Tyr Leu Arg Gln Ala Lys
            20                  25                  30 gtg ctg tgc cag ctg gac gag gag gag gtg ctg cac agc ccc cgg ctc     144
Val Leu Cys Gln Leu Asp Glu Glu Glu Val Leu His Ser Pro Arg Leu
        35                  40                  45 acc aac agc gcc atg cgg gcc ggg cac ttg ctg gat ttg ctg aag act     192
Thr Asn Ser Ala Met Arg Ala Gly His Leu Leu Asp Leu Leu Lys Thr
    50                  55                  60 cga ggg aag aac ggg gcc atc gcc ttc ctg gag agc ctg aag ttc cac     240
Arg Gly Lys Asn Gly Ala Ile Ala Phe Leu Glu Ser Leu Lys Phe His
65                  70                  75                  80 aac cct gac gtc tac acc ctg gtc acc ggg ctg cag                     276
Asn Pro Asp Val Tyr Thr Leu Val Thr Gly Leu Gln
                85                  90
```

<210> SEQ ID NO 18
<211> LENGTH: 92
<212> TYPE: PRT
<213> ORGANISM: Homo sapiens

<400> SEQUENCE: 18

Glu Glu Thr Leu Trp Glu Met Met Glu Ser His Arg His Arg Ile Val
1               5                   10                  15

Arg Cys Ile Cys Pro Ser Arg Leu Thr Pro Tyr Leu Arg Gln Ala Lys
            20                  25                  30

Val Leu Cys Gln Leu Asp Glu Glu Glu Val Leu His Ser Pro Arg Leu
        35                  40                  45

Thr Asn Ser Ala Met Arg Ala Gly His Leu Leu Asp Leu Leu Lys Thr
    50                  55                  60

Arg Gly Lys Asn Gly Ala Ile Ala Phe Leu Glu Ser Leu Lys Phe His
65                  70                  75                  80

Asn Pro Asp Val Tyr Thr Leu Val Thr Gly Leu Gln
                85                  90

<210> SEQ ID NO 19
<211> LENGTH: 2176
<212> TYPE: DNA
<213> ORGANISM: Homo sapiens
<220> FEATURE:
<221> NAME/KEY: CDS
<222> LOCATION: (147)...(1247)

<400> SEQUENCE: 19
atcatcagga agtgcacagg cgtccggcgt gctcctccct ccctgcagcc ccgggcagca     60
tctcccagag gctccgcggc ccaggctcct ggtgtgtctg cagtgcaggt ggctcctgga    120

```
agaccctcag cctgcctgct gaggcc atg tcg gac tac gag aac gat gac gag        173
                             Met Ser Asp Tyr Glu Asn Asp Asp Glu
                              1               5 tgc tgg aac gtc ctg gag ggc ttc cgg gtg acg ctc acc tcg gtc atc         221
Cys Trp Asn Val Leu Glu Gly Phe Arg Val Thr Leu Thr Ser Val Ile
 10              15                  20                  25 gac ccc tca cgc atc aca cct tac ctg cgg cag tgc aag gtc ctg aac         269
Asp Pro Ser Arg Ile Thr Pro Tyr Leu Arg Gln Cys Lys Val Leu Asn
                 30                  35                  40 cct gat gat gag gag cag gtg ctc agc gac ccc aac ctg gtc atc cgc         317
Pro Asp Asp Glu Glu Gln Val Leu Ser Asp Pro Asn Leu Val Ile Arg
             45                  50                  55 aaa cgg aaa gtg ggt gtg ctc ctg gac atc ctg cag cgg acc ggc cac         365
Lys Arg Lys Val Gly Val Leu Leu Asp Ile Leu Gln Arg Thr Gly His
         60                  65                  70 aag ggc tac gtg gcc ttc ctc gag agc ctg gag ctc tac tac ccg cag         413
Lys Gly Tyr Val Ala Phe Leu Glu Ser Leu Glu Leu Tyr Tyr Pro Gln
     75                  80                  85 ctg tac aag aag gtc aca ggc aag gag ccg gcc cgc gtc ttc tcc atg         461
Leu Tyr Lys Lys Val Thr Gly Lys Glu Pro Ala Arg Val Phe Ser Met
 90                  95                 100                 105 atc atc gac gcg tcc ggg gag tca ggc ctg act cag ctg ctg atg act         509
Ile Ile Asp Ala Ser Gly Glu Ser Gly Leu Thr Gln Leu Leu Met Thr
                110                 115                 120 gag gtc atg aag ctg cag aag aag gtg cag gac ctg acc gcg ctg ctg         557
Glu Val Met Lys Leu Gln Lys Lys Val Gln Asp Leu Thr Ala Leu Leu
            125                 130                 135 agc tcc aaa gat gac ttc atc aag gag ctg cgg gtg aag gac agc ctg         605
Ser Ser Lys Asp Asp Phe Ile Lys Glu Leu Arg Val Lys Asp Ser Leu
        140                 145                 150 ctg cgc aag cac cag gag cgt gtg cag agg ctc aag gag gag tgc gag         653
Leu Arg Lys His Gln Glu Arg Val Gln Arg Leu Lys Glu Glu Cys Glu
    155                 160                 165 gcc ggc agc cgc gag ctc aag cgc tgc aag gag gag aac tac gac ctg         701
Ala Gly Ser Arg Glu Leu Lys Arg Cys Lys Glu Glu Asn Tyr Asp Leu
170                 175                 180                 185 gcc atg cgc ctg gcg cac cag agt gag gag aag ggc gcc gcg ctc atg         749
Ala Met Arg Leu Ala His Gln Ser Glu Glu Lys Gly Ala Ala Leu Met
                190                 195                 200 cgg aac cgt gac ctg cag ctg gag att gac cag ctc aag cac agc ctc         797
Arg Asn Arg Asp Leu Gln Leu Glu Ile Asp Gln Leu Lys His Ser Leu
            205                 210                 215 atg aag gcc gag gac gac tgc aag gtg gag cgc aag cac acg ctg aag         845
Met Lys Ala Glu Asp Asp Cys Lys Val Glu Arg Lys His Thr Leu Lys
        220                 225                 230 ctc agg cac gcc atg gag cag cgg ccc agc cag gag ctg ctg tgg gag         893
Leu Arg His Ala Met Glu Gln Arg Pro Ser Gln Glu Leu Leu Trp Glu
    235                 240                 245 ctg cag cag gag aag gcc ctc ctc cag gcc cgg gtg cag gag ctg gag         941
Leu Gln Gln Glu Lys Ala Leu Leu Gln Ala Arg Val Gln Glu Leu Glu
250                 255                 260                 265 gcc tcc gtc cag gag ggg aag ctg gac agg agc agc ccc tac atc cag         989
Ala Ser Val Gln Glu Gly Lys Leu Asp Arg Ser Ser Pro Tyr Ile Gln
                270                 275                 280 gta ctg gag gag gac tgg cgg cag gcg ctg cgg gac cac cag gag cag         1037
Val Leu Glu Glu Asp Trp Arg Gln Ala Leu Arg Asp His Gln Glu Gln
            285                 290                 295 gcc aac acc atc ttc tcc ctg cgc aag gac ctc cgc cag ggc gag gcc         1085
Ala Asn Thr Ile Phe Ser Leu Arg Lys Asp Leu Arg Gln Gly Glu Ala
```

```
                         300                 305                 310
cga cgc ctc cgg tgc atg gag gag aag gag atg ttc gag ctg cag tgc       1133
Arg Arg Leu Arg Cys Met Glu Glu Lys Glu Met Phe Glu Leu Gln Cys
        315                 320                 325 ctg gca cta cgt aag gac tcc aag atg tac aag gac cgc atc gag gcc       1181
Leu Ala Leu Arg Lys Asp Ser Lys Met Tyr Lys Asp Arg Ile Glu Ala
330                 335                 340                 345 atc ctg ctg cag atg gag gag gtc gcc att gag cgg gac cag agc aca       1229
Ile Leu Leu Gln Met Glu Glu Val Ala Ile Glu Arg Asp Gln Ser Thr
                350                 355                 360 caa atg gag ggg ctg tga ccagcctccg cgcccagcgg cttgacgtcc              1277
Gln Met Glu Gly Leu *
                365 tccggagcct ctgcttggag ttgggcggcc gggccgaggg cccagggcaa gcttggggcc     1337 ctcactgagg gtcggccttg tgctgtcccg tcaggccata gccacgcggg aggagctgca     1397 cgcacagcac gcccggggcc tgcaggagaa ggacgcgctg cgcaagcagg tgcgggagct     1457 gggcgagaag gcggatgagc tgcagctgca ggtgttccag tgtgaggcgc agctactggc     1517 cgtggagggc aggctcaggc ggcagcagct ggagacgctc gtcctgagct ccgacctgga     1577 agatggctca cccaggaggt cccaggagct ctcactcccc caggacctgg aggacaccca     1637 gctctcagac aaaggctgcc ttgccggcgg ggggagcccg aaacagccct ttgcagctct     1697 gcaccaggag caggttttgc ggaaccccca tgacgcaggc ctgagcagcg ggagccgcc     1757 cgagaaggag cggcggcgcc tcaaagagag ttttgagaac taccgcagga agcgcgccct     1817 caggaagatg cagaaaggat ggcggcaggg ggaggaggac cgggagaaca ccacgggcag     1877 cgacaacacc gacactgagg gctcctagcc gcagcagact tccccgagcc gtcgctgact     1937 tggcctggaa cgaggaatct ggtgccctga aaggcccagc cggactgccg ggcattgggg     1997 ccgtttgtta agcggcactc attttgcgga ggccatgcgg gtgctcacca cccccatgca     2057 cacgccatct gtgtaacttc aggatctgtt ctgtttcacc atgtaacaca aatacatgc     2117 atgcattgta ttagtgttag aaaacacagc tgcgtaaata aacagcacgg gtgacccgc     2176
```

<210> SEQ ID NO 20
<211> LENGTH: 366
<212> TYPE: PRT
<213> ORGANISM: Homo sapiens

<400> SEQUENCE: 20

```
Met Ser Asp Tyr Glu Asn Asp Asp Glu Cys Trp Asn Val Leu Glu Gly
1               5                   10                  15

Phe Arg Val Thr Leu Thr Ser Val Ile Asp Pro Ser Arg Ile Thr Pro
            20                  25                  30

Tyr Leu Arg Gln Cys Lys Val Leu Asn Pro Asp Asp Glu Glu Gln Val
        35                  40                  45

Leu Ser Asp Pro Asn Leu Val Ile Arg Lys Arg Lys Val Gly Val Leu
    50                  55                  60

Leu Asp Ile Leu Gln Arg Thr Gly His Lys Gly Tyr Val Ala Phe Leu
65                  70                  75                  80

Glu Ser Leu Glu Leu Tyr Tyr Pro Gln Leu Tyr Lys Lys Val Thr Gly
                85                  90                  95

Lys Glu Pro Ala Arg Val Phe Ser Met Ile Ile Asp Ala Ser Gly Glu
            100                 105                 110

Ser Gly Leu Thr Gln Leu Leu Met Thr Glu Val Met Lys Leu Gln Lys
        115                 120                 125
```

```
Lys Val Gln Asp Leu Thr Ala Leu Leu Ser Ser Lys Asp Asp Phe Ile
            130                 135                 140

Lys Glu Leu Arg Val Lys Asp Ser Leu Leu Arg Lys His Gln Glu Arg
145                 150                 155                 160

Val Gln Arg Leu Lys Glu Glu Cys Glu Ala Gly Ser Arg Glu Leu Lys
                165                 170                 175

Arg Cys Lys Glu Glu Asn Tyr Asp Leu Ala Met Arg Leu Ala His Gln
            180                 185                 190

Ser Glu Glu Lys Gly Ala Ala Leu Met Arg Asn Arg Asp Leu Gln Leu
        195                 200                 205

Glu Ile Asp Gln Leu Lys His Ser Leu Met Lys Ala Glu Asp Asp Cys
    210                 215                 220

Lys Val Glu Arg Lys His Thr Leu Lys Leu Arg His Ala Met Glu Gln
225                 230                 235                 240

Arg Pro Ser Gln Glu Leu Leu Trp Glu Leu Gln Gln Glu Lys Ala Leu
                245                 250                 255

Leu Gln Ala Arg Val Gln Glu Leu Glu Ala Ser Val Gln Glu Gly Lys
            260                 265                 270

Leu Asp Arg Ser Ser Pro Tyr Ile Gln Val Leu Glu Glu Asp Trp Arg
        275                 280                 285

Gln Ala Leu Arg Asp His Gln Glu Gln Ala Asn Thr Ile Phe Ser Leu
    290                 295                 300

Arg Lys Asp Leu Arg Gln Gly Glu Ala Arg Arg Leu Arg Cys Met Glu
305                 310                 315                 320

Glu Lys Glu Met Phe Glu Leu Gln Cys Leu Ala Leu Arg Lys Asp Ser
                325                 330                 335

Lys Met Tyr Lys Asp Arg Ile Glu Ala Ile Leu Leu Gln Met Glu Glu
            340                 345                 350

Val Ala Ile Glu Arg Asp Gln Ser Thr Gln Met Glu Gly Leu
        355                 360                 365

<210> SEQ ID NO 21
<211> LENGTH: 281
<212> TYPE: DNA
<213> ORGANISM: Homo sapiens

<400> SEQUENCE: 21
gagaggctcc gcggcccagg ctcctggtgt gtctgcagtg caggtggctc ctggaagacc      60
ctcagcctgc ctgctgaggc catgtttgac tacgagaacg atgacgagtg ctggagcgtc     120
ctggagggct tccgggtgac gctcacctcg gtcatcgacc cctcacgcat cacaccttac     180
ctgcggcagt gcaaggtcct gaaccccgat gatgaggagc aggtgctcag cgaccccaac     240
ctggtcatcc gcaaacggaa agtgggtgtg ctcctggaca t                         281

<210> SEQ ID NO 22
<211> LENGTH: 734
<212> TYPE: DNA
<213> ORGANISM: Gallus gallus

<400> SEQUENCE: 22
gggacagcct gctccgcaag caccaagagc gggtgcagaa gatgagggag gagagggaca      60
gtctaagcaa ggagctgcgg aagtgcaagg atgagaacta caacctggca atgagctatg     120
ccagacagag cgaggagaag agcagtgccc tcatgaagaa cagggacctg ctcctagaga     180
ttgatagctt gaagcatagc ctcatgaagg ctgaggacga ctgcaaacta gagcgtaagc     240
```

```
actcgatgaa actgaagcat gccatagaac aacgtccgag ccatgaagtg atgtgggaga      300
tccagcagga gaaggagctg cttttggcca gaatcagga gctggagaac actcttcagg      360
ttgccaggga acagaatttg gagacgagtc tctcccatga gactgtgcag aatgactgca      420
gccaggtgct ggagcgccag gacctgctga cacccctgta ccaccttcgc aaggagctgc      480
gccaagccga ggtgcttcga gacaagttcg aggagtgcag ctcagcccac gaggagctgt      540
ccgagaagga gcggaggagg atgaaggact gctttgagcg ttaccgcagg aagcgcgccc      600
tgcgcagagc gcccgcgggc ccgccgcccc gaggccgact gggagccgag cacgggcagc      660
gacaacacgg acaccgaggg cagctagggg ccggccgagc tttcgagttt gcagctggat      720
ccgtcaataa acag                                                       734

<210> SEQ ID NO 23
<211> LENGTH: 630
<212> TYPE: DNA
<213> ORGANISM: Gallus gallus

<400> SEQUENCE: 23
tgaacaccct gtaccacctt cgcaaggagc tgcgccaagc cgaggtgctc cgagacaagt       60
atgcagagga aaagaaata cttgaactac agtgcacatc tctgaggaag gactcccaga      120
tgtataaaaa acggatggaa gctgtcttag agcagatgga ggaagtggct tcggaaagag      180
accaggcact gctgaccaga gaacagttct acccacagta ctccaagaac cttgttgaga      240
gggacactta tcggaagcag attcgggagc tggggagcg atgcgatgag ctgcagctgc      300
agctcttcca aaaggagggt cagctactgg ctactgaagc caagctgaaa agactgcaac      360
tggagctgcc tgcactgact tctgacctgg atgcactcc tccagagatc ccaggtctta      420
ctctcatggt catctagacg aagatcgcac ctgactaaaa aagacgctgt taaggaaaac      480
cagcaatcag catgcaagaa acatctgacg cagatcacca cttcgaggat gcactaacca      540
caagacttcg agaagacgga gagataagga tgcttgagcg tacgagtcgg ccgatccgcg      600 cccccctcc gcgctccttc cgtggctcgt                                       630

<210> SEQ ID NO 24
<211> LENGTH: 331
<212> TYPE: DNA
<213> ORGANISM: Homo sapiens

<400> SEQUENCE: 24
cacgagggaa atgtacaagc accgcatgaa cacggtcatg ctgcacctgg aggaggtgga       60 gcggagcgg gaccaggcct tccactcccg agatgaagct cagacacagt actcgcagtg      120
cttaatcgaa aaggacaagt acaggaagca gatccgcgag ctggaggaga agaacgacga      180
gatgaggatc gagatggtgc ggcgggaggc ctgcatcgtc aacctggaga gcaagctgcg      240
gcgcctctcc aaggacagca caaacctgga ccagagtctg cccaggaacc tgccagtaac      300
catcatctct caggactttg gggatgccag c                                    331

<210> SEQ ID NO 25
<211> LENGTH: 478
<212> TYPE: DNA
<213> ORGANISM: Homo sapiens

<400> SEQUENCE: 25
tttttttttt ttttctctc ctgcctcctc tggccttcgg actcctgccc gcgccgcccg       60
```

| | |
|---|---:|
| cagcccctc ccggccctgc agccctggg cgggcggcgc ccctcggagg acggctccgg | 120 |
| gcccggggg acggagggcc tggtcgcctg gaggaagccg gaggcctgcg tggaggaggc | 180 |
| gccccgcgca gctggctggc ggagcatgag cgcccagat cccaagcact gcaagtccag | 240 |
| atgcaacggg agcctggctc aagggacgac aagatccagc cggaaagtgt agaagtcaca | 300 |
| ccccaatggc gggatagcag cccctgtgtg tgagcacccc tccatgccag gaggagggcc | 360 |
| agagatggat gactacatgg agaccctgaa ggatgaagag gacccttgt gggacaatgt | 420 |
| ggagtgtaac cggcacatgc tcaaccgcta tatcaaccct gccaagctca cgccctac | 478 |

<210> SEQ ID NO 26
<211> LENGTH: 396
<212> TYPE: DNA
<213> ORGANISM: Homo sapiens

<400> SEQUENCE: 26

| | |
|---|---:|
| gcagccccct cccggccctg cagccctgg cgtgcggcgc catcggagga cggctccggg | 60 |
| cccgggggga cggagggcct ggtcgcctgg aggaagccgg acgctgcgtg gaggaggcgc | 120 |
| ccccggtctg gtctggcgga cgatgagcgc cccagatccc aagcactgca agtccagatg | 180 |
| caacgggagc ctggctcaag gacgacaag atccagccgg aaagtgtaga agtcacaccc | 240 |
| caatggcgga tagcagcccc tgtgtgtga tcacccctcc atgccaggag gagggccaga | 300 |
| gatggatgac tacatggaga cgctgaatga tgaagaggac gccttgtggg agaatgtgga | 360 |
| gtgtaaccgg cacatgctca gccgctatat caaccc | 396 |

<210> SEQ ID NO 27
<211> LENGTH: 162
<212> TYPE: DNA
<213> ORGANISM: Homo sapiens

<400> SEQUENCE: 27

| | |
|---|---:|
| aaaaggagga gggccagaga tggatgacta catggagacg ctgaaggatg aagaggacgc | 60 |
| cttgtgggtg aatgtggagt gtaaccggca catgctcagc cgggtctcac gaattccgct | 120 |
| gagttctcac gaattccgct gaggtctcac gaattccgct ga | 162 |

<210> SEQ ID NO 28
<211> LENGTH: 418
<212> TYPE: DNA
<213> ORGANISM: Homo sapiens

<400> SEQUENCE: 28

| | |
|---|---:|
| cacgacgacg gacgccagcc ctagctcctg cggatctctg cccatcacca actccttcac | 60 |
| caagatgcag cccccccgga gccgcagcag catcatgtca atcaccgccg agcccccggg | 120 |
| aaacgactcc atcgtcagac gctacaagga ggacgcgccc catcgcagca cagtcgaaga | 180 |
| agacaatgac agcggcgggt tgacgccttt agatctggat gatgacagtc acgaacgcta | 240 |
| ctccttcgga ccctcctcca tccactcctc ctcctcctcc caccaatccg agggcctgga | 300 |
| tgcctacgac ctggagcagg tcaacctcat gttcaggaag ttctctctgg aaagaccctt | 360 |
| ccggccttcg gtcacctctg tggggcacgt tcggggccca aggccctcgg tgcagcac | 418 |

<210> SEQ ID NO 29
<211> LENGTH: 610
<212> TYPE: DNA
<213> ORGANISM: Homo sapiens

<400> SEQUENCE: 29

```
tcatccccta cagcctggta cgcgccttct actgcgagcg ccgccggccc gtgctcttca      60
cacccaccgt gctggccaag acgctggtgc agaggctgct caactcggga ggtgccatgg     120
agttcaccat ctgcaagtca gatatcgtca agagatgat gttcctcaga aggcagaaga      180
cggagaccat catctactcc cgagagaaga accccaacgc gttcgaatgc atcgcccctg     240
ccaacatcga agctgtggcc gccaagaaca agcactgcct gctggaggct gggatcggct     300
gcacaagaga cttgatcaag tccaacatct accccatcgt gctcttcatc cgggtgtgtg     360
agaagaacat caagaggttc agaaagctgc tgccccgacc tgagacggag gaggagttcc     420
tgcgcgtgtg ccggctgaag gagaaggagc tggaggccct gccgtgcctg tacgccacgg     480
tggaacctga catgtggggc agcgtagagg agctgctccg cgttgtcaag acaagatcg     540 gcgaggagca gcgcaagacc atctgggtgg acgaggacca gctgtgaggc gggcgccctg     600
ggcagagaga                                                            610
```

<210> SEQ ID NO 30
<211> LENGTH: 556
<212> TYPE: DNA
<213> ORGANISM: Homo sapiens
<220> FEATURE:
<221> NAME/KEY: misc_feature
<222> LOCATION: 470
<223> OTHER INFORMATION: n = A,T,C or G

<400> SEQUENCE: 30

```
tcatccccta cagcctggta cgcgccttct actgcgagcg ccgccggccc gtgctcttca      60
cacccaccgt gctggccaag acgctggtgc agaggctgct caactcggga ggtgccatgg     120
agttcaccat ctgcaagtca gatatcgtca agagatgat gttcctcaga aggcagaaga      180
cggagaccat catctactcc cgagagaaga accccaacgc gttcgaatgc atcgcccctg     240
ccaacatcga agctgtggcc gccaagaaca agcactgcct gctggaggct gggatcggct     300
gcacaagaga cttgatcaag tccaacatct accccatcgt gctcttcatc cgggtgtgtg     360
agaagaacat caagaggttc agaaagctgc tgccccgacc tgagacggag gaggagttcc     420
tgcgcgtgtg ccggctgaag gagaaggagc tggaggccct gccgttgccn tggtacgcca     480
cggtggaacc tgacatgtgg ggcagcgtag aggagctgct ccgcgtgtca ggacagacgg     540
cgagagcagc gcaaga                                                     556
```

<210> SEQ ID NO 31
<211> LENGTH: 390
<212> TYPE: DNA
<213> ORGANISM: Homo sapiens

<400> SEQUENCE: 31

```
gctccttcag ttcgtcagca ggtccgagaa caagtataag cggatgaaca gcaacgagcg      60
ggtccgatca tctcggggag tccgctagga gcctggcccg gtcctcgctg gacgccacca     120
agctcttgac tgagaagcag gaagagctgg accctgagag cgagctgggc aagaacctca     180
gcctcatccc ctacagcctg gtacgcgcct tctactgcga gcgccgccgg cctgtgctct     240
tcacacccac cgtgctggcc aagacgctgg tgcagaggct gctcaactcg ggaggtgcca     300
tggagttcac catctgcaag tcagatatcg tcacaagaga tgagttcctc agaaggcaga     360
agacggagac catcatctac tcccgagaga                                      390
```

<210> SEQ ID NO 32

<211> LENGTH: 620
<212> TYPE: DNA
<213> ORGANISM: Homo sapiens

<400> SEQUENCE: 32

```
agagacttga tcaagtccaa catctacccc atcgtgctct tcatccgggt gtgtgagaag    60
aacatcaaga ggttcagaaa gctgctgccc cggcctgaga cggaggagga gttcctgcgc   120
gtgtgccggc tgaaggagaa ggagctggag gccctgccgt gcctgtacgc cacggtggaa   180
cctgacatgt ggggcagcgt agaggagctg ctccgcgttg tcaaggacaa gatcggcgag   240
gagcagcgca agaccatctg ggtggacgag gaccagctgt gaggcgggcg ccctgggcag   300
agagactctg tggcgcgggg catcctatga ggcaggcacc ctgggcagag agatgtagtg   360
ggtgcggggg gatcctgtgg cccacagagc tgccccagca gacgctccgc cccacccggt   420
gatggagccc cggggggaca gtcgtgcctg ggaggagca gggtacagcc cattccccca    480
gccctggctg acctggccta gcagttttgg ccctgctggc cttagcaggg agacagggga   540
gcaaagaacg ccaagccggg aggcccaagc cagccgggct ctcgaggggg ggcccggtcc   600
ccattttgcc ctttatgagc                                               620
```

<210> SEQ ID NO 33
<211> LENGTH: 283
<212> TYPE: DNA
<213> ORGANISM: Homo sapiens
<220> FEATURE:
<221> NAME/KEY: misc_feature
<222> LOCATION: 42, 85, 109, 111, 139, 222, 244, 263
<223> OTHER INFORMATION: n = A,T,C or G

<400> SEQUENCE: 33

```
aagagacttg atcaagtcca acatctaccc catcgtgctc tntcatccgg gtgtgtgaga    60
agaacatcaa gaggttcaga aagcngctgc cccggcctga dacggaggng nagttcctgc   120
gcgtgtgccg gctgaaggng aaggagctgg aggccctgcc gtgcctgtac gcgacggtgg   180
aacctgacat gtggggcagc gtagaggagc tgctccgcgt tntataagga caagatcggt   240
gagnagcagc gcaagaccat ctnggtagac gaggaccagc ttt                     283
```

<210> SEQ ID NO 34
<211> LENGTH: 207
<212> TYPE: DNA
<213> ORGANISM: Homo sapiens

<400> SEQUENCE: 34

```
gtgtactgcc ttctgaggaa ctcatctctg tgacgatatc tgacttgcag atggtgaact    60
ccatggcacc tcccgagttg agcagcctct gcaccagcgt cttggccagc acggtgggtg   120
tgaagagcac gggccggcgg cgctcgcagt agaaggcgcg taccaggctg tagggatga    180
ggctgaggtt cttgcccagc tcgctct                                       207
```

<210> SEQ ID NO 35
<211> LENGTH: 192
<212> TYPE: DNA
<213> ORGANISM: Homo sapiens

<400> SEQUENCE: 35

```
gacttgatca agtccaacat ctaccccatc gtgctcttca tccgggtgtg tgagaagaac    60
atcaagaggt tcagaaagct gctgcccegg cctgagactg aggaggagt tcctgcgcgt   120
gtgccggctg aaggagaagg agctggaggc cctgcgatgc ctgtacgcca cggtggaacc   180
```

<210> SEQ ID NO 36
<211> LENGTH: 605
<212> TYPE: DNA
<213> ORGANISM: Homo sapiens
<220> FEATURE:
<221> NAME/KEY: misc_feature
<222> LOCATION: 213
<223> OTHER INFORMATION: n = A,T,C or G

<400> SEQUENCE: 36

```
gaaataataa tacattttaa tgcaagagaa atcatagcct ggtacacacc ccttccccga      60
tctgtcctgc ctggggatgt gtttatggtg agtgtgtccc caggactggt agtcacctgg     120
ctgtccgggt ccccgcccta ctggcggcag catgcctgtc cccagcatta cattcaactg     180
ctgctctggc tctcgagagg ccggctggcc tcnggccttc cggcttggcg ttctttgctc     240
ccctgtctcc ctgctaaggc cagcagggcc aaactgctag gccaggtcag ccagggctgg     300
gggaatgggc tgtaccctgc tcctccccag gcacgactgt ccccccgggg ctccatcacc     360
gggtggggcg gagcgtctgc tggggcagct ctgtgggcca caggatcccc ccgcacccac     420
tgcatctctc tgcccatggt gcctgcctca taggatgccc cgcgccacag agtctatatg     480
tccagggcgc ccgcctcaca gctggtcctc gtccacccag atggtcttgc gctgctcctc     540
gccgatcttg tccttgacat cgcggagcag ctcctttacg ctgccccaca tgtcaggtgc     600
ccccg                                                                605
```

<210> SEQ ID NO 37
<211> LENGTH: 1141
<212> TYPE: DNA
<213> ORGANISM: Homo sapiens

<400> SEQUENCE: 37

```
tcatgcccag ctccgtccca cccagcagcc cgcagagaaa ggaggcagct ggcaccacac      60
tgggctttgg agacactgcg gggactgtgg accccaccct gctgcacgga gctcctgcaa     120
aagcaaacct gagaaccttg ggtcctccca gcgcccagcc atgggggaac tgtgccgcag     180
ggactccgca ctcacggcac tggacgagga gacactgtgg gagatgatgg agagccaccg     240
ccacaggatc gtacgctgca tctgccccag acgacattaa ccctatact gtgacgcaca     300
gcgccagagg ctggctgctg accatggatg gaccgaggag ggaggttgct gcaccagcgc     360
ccacgagaca tcaacaacag acgcacactg cggggccggg cacatagcgt ggcctcgcgc     420
tagaaagaca tcagaggaga aagaagcggg ggcccactcg cactcaccgt gagtagacgc     480
catgcacagt accaccaaac ccatgagcgc tactacaacc catgggtcac cagggcatga     540
cagcctggat gcatagacat aacaagtaac ttctactagc caggtcctca tgcgaagacc     600
atcccaagcc tgaccgaca tgccctggac atggggccca ctacgcgcag accatgcagc     660
gagagacgca tgacaccagg caacaacgcg ggccacgaac gcgagcgttg cctgcatcga     720
cgggcacggt tggccacaga cacggaattg cagcggagcc acacgtggca gcccctgagg     780
cccgacgaca cccggtgcac cgaagggggcc atggcaacca cgacctggca ggcttgacac     840
```

-continued

| | | | | | |
|---|---|---|---|---|---|
| accaagcgcc | ataccacgcg | cgtgaaaggg | tacagaggca | ccaactaccc | agtgcaagcg | 900 |
| cagttcttgc | aaggcgatgc | caagggaacg | gcacgacatg | acgacaccgc | agtactctgt | 960 |
| gaggaaacca | tcttagcaag | atgacagcct | tgacaggaaa | caacgacacg | aagtgcctgt | 1020 |
| ctcgcaacgc | atgacagaag | acctgtcgca | tataaagtaa | atgtgatact | aatagaaagc | 1080 |
| aagaaggttg | acactgaaag | acacacatat | gagtataact | cgagtatgca | acgtgaacat | 1140 |
| g | | | | | | 1141 |

What is claimed is:

1. A substantially purified CARD-containing polypeptide consisting of the amino acid sequence of the CARD-12X polypeptide sequence SEQ ID NO:16.

2. A substantially purified polypeptide consisting of the amino acid sequence of the CARD domain amino acid sequence SEQ ID NO: 18.

\* \* \* \* \*